United States Patent
Ozawa et al.

(10) Patent No.: US 12,291,754 B2
(45) Date of Patent: May 6, 2025

(54) CULTURE-RELATED PROCESS OPTIMIZATION METHOD AND CULTURE-RELATED PROCESS OPTIMIZATION SYSTEM

(71) Applicant: EPISTRA INC., Tokyo (JP)

(72) Inventors: Yosuke Ozawa, Tokyo (JP); Taku Tsuzuki, Tokyo (JP); Tatsuki Higashi, Tokyo (JP)

(73) Assignee: EPISTRA INC., Tokyo (JP)

( * ) Notice: Subject to any disclaimer, the term of this patent is extended or adjusted under 35 U.S.C. 154(b) by 0 days.

(21) Appl. No.: 18/688,351

(22) PCT Filed: Aug. 30, 2022

(86) PCT No.: PCT/JP2022/032667
§ 371 (c)(1),
(2) Date: Feb. 29, 2024

(87) PCT Pub. No.: WO2023/033005
PCT Pub. Date: Mar. 9, 2023

(65) Prior Publication Data
US 2024/0327935 A1 Oct. 3, 2024

(30) Foreign Application Priority Data
Aug. 31, 2021 (JP) .................. 2021-141911

(51) Int. Cl.
*C12Q 3/00* (2006.01)
(52) U.S. Cl.
CPC ..................... *C12Q 3/00* (2013.01)
(58) Field of Classification Search
CPC ......... C12Q 3/00; C12M 41/26; C12M 41/12; C12M 41/32; G16C 20/70; G16C 20/10
See application file for complete search history.

(56) References Cited

U.S. PATENT DOCUMENTS

| 8,406,928 | B2 * | 3/2013 | Gupta | C08F 10/02 |
| | | | | 700/282 |
| 8,433,443 | B2 * | 4/2013 | Hagerty | C08F 10/00 |
| | | | | 526/60 |

(Continued)

FOREIGN PATENT DOCUMENTS

| JP | H06168248 A | 6/1994 |
| JP | 2006106873 A | 4/2006 |

(Continued)

OTHER PUBLICATIONS

First Office Action issued in corresponding Chinese Patent Application No. 202280057251.6, mailed Jun. 27, 2024, [with translation] (13 pages), Only the English portion.

(Continued)

*Primary Examiner* — Shogo Sasaki
(74) *Attorney, Agent, or Firm* — Osha Bergman Watanabe & Burton LLP

(57) ABSTRACT

A culture-related process optimization method includes: acquiring a starting point execution procedure, which serves as a starting point of a search and in which contents related to operations performed in the culture-related process are specified; identifying a variable parameter item for which a variable parameter value can be set in the starting point execution procedure; setting the variable parameter value for the variable parameter item on the basis of a previous execution performance result and an evaluation performance result thereof and thereby generating an execution procedure; acquiring an execution result obtained when an execution subject actually executes execution according to the execution procedure in an execution environment; acquiring an evaluation result with respect to the execution result, by an evaluation result acquisition unit; and recording the execution procedure, the variable parameter value, the (Continued)

execution result, and the evaluation result in association with each other.

14 Claims, 60 Drawing Sheets

(56) References Cited

U.S. PATENT DOCUMENTS

| | | | | |
|---|---|---|---|---|
| 8,818,562 | B2* | 8/2014 | Bluck | C12M 41/00 436/24 |
| 11,505,778 | B2* | 11/2022 | Shimodaira | C07C 227/28 |
| 12,002,549 | B2* | 6/2024 | Luan | G16B 40/20 |
| 2018/0196913 | A1 | 7/2018 | Yoshikawa et al. | |
| 2020/0199529 | A1 | 6/2020 | Yoda et al. | |
| 2020/0308529 | A1* | 10/2020 | Shimodaira | C12P 13/08 |
| 2021/0163874 | A1 | 6/2021 | Noguchi et al. | |
| 2022/0380717 | A1 | 12/2022 | Terao | |
| 2022/0404782 | A1 | 12/2022 | Ozawa et al. | |
| 2023/0305528 | A1 | 9/2023 | Ozawa et al. | |
| 2024/0038324 | A1* | 2/2024 | Luan | G16B 5/30 |

FOREIGN PATENT DOCUMENTS

| | | |
|---|---|---|
| JP | 2015230702 A | 12/2015 |
| JP | 2019101683 A | 6/2019 |
| WO | 2019031545 A1 | 2/2019 |
| WO | 2020012853 A1 | 1/2020 |
| WO | 2020039683 A1 | 2/2020 |
| WO | 2021049044 A1 | 3/2021 |
| WO | 2021166824 A1 | 8/2021 |
| WO | 2022044345 A1 | 3/2022 |

OTHER PUBLICATIONS

Rui, G. et al., "In vitro culture of osteoblasts: A bibliometric analysis based on Science Citation Index, National Institutes of Health and Derwent Innovations Index from 2008 to 2010" Chinese Journal of Tissue Engineering Research, vol. 16, No. 2. p. 191-200, 2012, with English abstract (10 pages), Only the English portion.

Notice of Reasons for Refusal issued in related Japanese Application No. 2021-141911 mailed Sep. 5, 2023 (4 pages).

Decision to Grant a Patent issued in related Japanese Application No. 2021-141911 mailed Dec. 19, 2023 (5 pages).

Sheremetyeva, S., Nirenburg, S., & Nirenburg, I. (1996). Generating patent claims from interactive input. In Eighth International Natural Language Generation Workshop (11 pages).

Sheremetyeva, S. (Jul. 2003). Natural language analysis of patent claims. In Proceedings of the ACL-2003 workshop on Patent corpus processing (pp. 66-73) (9 pages).

Shinmori, A., Okumura, M., Marukawa, Y., & Iwayama, M. (Jul. 2003). Patent claim processing for readability-structure analysis and term explanation. In Proceedings of (10 pages).

International Search Report issued in corresponding International Application No. PCT/JP2022/032667 mailed Nov. 22, 2022 (5 pages).

Written Opinion issued in corresponding International Application No. PCT/JP2022/032667 mailed Nov. 22, 2022 (4 pages).

* cited by examiner

FIG. 2

| | EXECUTION PROCEDURE SERVING AS STARTING POINT OF SEARCH |
|---|---|
| C1 | 1. CULTURE-RELATED PROCESS |
| 26a | 1-1. OPERATION: ADJUSTMENT OF DIFFERENTIATION-INDUCING CULTURE MEDIUM A |
| 26b | input: BASAL CULTURE MEDIUM, BMP4, VEGF |
| 26c | output: DIFFERENTIATION-INDUCING CULTURE MEDIUM A |
| 26d | EXECUTION PARAMETER VALUE: BASAL CULTURE MEDIUM CONCENTRATION 10 mM, BMP4 CONCENTRATION: 2 μM, VEGF CONCENTRATION: 5 μM, GLUCOSE CONCENTRATION: 4 μM |
| 26e | CONSTRAINT CONDITION: NONE |
| C2 | 1-2. OPERATION: CELL CULTURE USING DIFFERENTIATION-INDUCING CULTURE MEDIUM A (INTENDED CELL INDUCTION) |
| | input: DIFFERENTIATION-INDUCING CULTURE MEDIUM A (ADJUSTED), HUMAN iPS CELLS (HPS0003 STRAIN) |
| | output: HUMAN iPS CELLS (HPS0003 STRAIN) (BEING IN MIDDLE OF DIFFERENTIATION) |
| | EXECUTION PARAMETER VALUE: CULTURE PERIOD: 6 DAYS |
| | CONSTRAINT CONDITION: WITHIN 60 MINUTES AFTER ADJUSTMENT OF DIFFERENTIATION-INDUCING CULTURE MEDIUM A IS FINISHED |
| C3 | 1-3. OPERATION: ADJUSTMENT OF DIFFERENTIATION-INDUCING CULTURE MEDIUM B |
| | input: DIFFERENTIATION-INDUCING BASAL CULTURE MEDIUM, BMP4, VEGF, SCF |
| | output: DIFFERENTIATION-INDUCING CULTURE MEDIUM B |
| | EXECUTION PARAMETER VALUE: BASAL CULTURE MEDIUM CONCENTRATION 10 mM, BMP4 CONCENTRATION: 2 μM, VEGF CONCENTRATION: 4 μM, SCF CONCENTRATION: 10 μM |
| | CONSTRAINT CONDITION: NONE |
| C4 | 1-4. OPERATION: CELL CULTURE USING DIFFERENTIATION-INDUCING CULTURE MEDIUM B (INTENDED CELL DIFFERENTIATION) |
| | input: DIFFERENTIATION-INDUCING CULTURE MEDIUM B (ADJUSTED), HUMAN iPS CELLS (HPS0003 STRAIN) (CULTURED IN DIFFERENTIATION-INDUCING CULTURE MEDIUM A AND BEING IN MIDDLE OF DIFFERENTIATION) |
| | output: HUMAN iPS CELLS (HPS0003 STRAIN) AFTER INDUCTION OF DIFFERENTIATION |
| | EXECUTION PARAMETER VALUE: CULTURE PERIOD: 6 DAYS |
| | CONSTRAINT CONDITION: WITHIN 60 MINUTES AFTER ADJUSTMENT OF DIFFERENTIATION-INDUCING CULTURE MEDIUM B IS FINISHED |
| C5 | 2. EVALUATION PROCESS |
| | 2-1. MARKER GENE EXPRESSION EVALUATION |
| | input: HUMAN iPS CELLS (HPS0003 STRAIN) AFTER INDUCTION OF DIFFERENTIATION |
| | output: MARKER GENE EXPRESSION POSITIVE RATE (0% TO 100%) |
| | EXECUTION PARAMETER VALUE: NONE |
| | CONSTRAINT CONDITION: NONE |

FIG. 3

EXECUTION PERFORMANCE RESULT AND EVALUATION PERFORMANCE RESULT 1 ACCORDING TO PREVIOUS EXECUTION PROCEDURE

| | |
|---|---|
| C1 | 1. CULTURE-RELATED PROCESS |
| 26a | 1-1. OPERATION: ADJUSTMENT OF DIFFERENTIATION-INDUCING CULTURE MEDIUM A |
| 26b | input: BASAL CULTURE MEDIUM, BMP4, VEGF |
| 26c | output: DIFFERENTIATION-INDUCING CULTURE MEDIUM A |
| 26d | EXECUTION PARAMETER VALUE: BASAL CULTURE MEDIUM CONCENTRATION 10 mM, BMP4 CONCENTRATION: 8 μM, VEGF CONCENTRATION: 12 μM, GLUCOSE CONCENTRATION: 4 μM |
| 26e | CONSTRAINT CONDITION: NONE |
| C2 | 1-2. OPERATION: CELL CULTURE USING DIFFERENTIATION-INDUCING CULTURE MEDIUM A (INTENDED CELL INDUCTION) |
| | input: DIFFERENTIATION-INDUCING CULTURE MEDIUM A (ADJUSTED), HUMAN iPS CELLS (HPS0003 STRAIN) |
| | output: HUMAN iPS CELLS (HPS0003 STRAIN) (BEING IN MIDDLE OF DIFFERENTIATION) |
| | EXECUTION PARAMETER VALUE: CULTURE PERIOD: 6 DAYS |
| | CONSTRAINT CONDITION: WITHIN 60 MINUTES AFTER ADJUSTMENT OF DIFFERENTIATION-INDUCING CULTURE MEDIUM A IS FINISHED |
| C3 | 1-3. OPERATION: ADJUSTMENT OF DIFFERENTIATION-INDUCING CULTURE MEDIUM B |
| | input: DIFFERENTIATION-INDUCING BASAL CULTURE MEDIUM, BMP4, VEGF, SCF |
| | output: DIFFERENTIATION-INDUCING CULTURE MEDIUM B |
| | EXECUTION PARAMETER VALUE: BASAL CULTURE MEDIUM CONCENTRATION 10 mM, BMP4 CONCENTRATION: 2 μM, VEGF CONCENTRATION: 4 μM, SCF CONCENTRATION: 10 μM |
| C4 | CONSTRAINT CONDITION: NONE |
| | 1-4. OPERATION: CELL CULTURE USING DIFFERENTIATION-INDUCING CULTURE MEDIUM B (INTENDED CELL DIFFERENTIATION) |
| | input: DIFFERENTIATION-INDUCING CULTURE MEDIUM B (ADJUSTED), HUMAN iPS CELLS (HPS0003 STRAIN) (CULTURED IN DIFFERENTIATION-INDUCING CULTURE MEDIUM A AND BEING IN MIDDLE OF DIFFERENTIATION) |
| | output: HUMAN iPS CELLS (HPS0003 STRAIN) AFTER INDUCTION OF DIFFERENTIATION |
| | EXECUTION PARAMETER VALUE: CULTURE PERIOD: 6 DAYS |
| | CONSTRAINT CONDITION: WITHIN 60 MINUTES AFTER ADJUSTMENT OF DIFFERENTIATION-INDUCING CULTURE MEDIUM B IS FINISHED |
| C5 | 2. EVALUATION PROCESS |
| | 2-1. MARKER GENE EXPRESSION EVALUATION |
| | input: HUMAN iPS CELLS (HPS0003 STRAIN) AFTER INDUCTION OF DIFFERENTIATION |
| | output: MARKER GENE EXPRESSION POSITIVE RATE 75% |
| | EXECUTION PARAMETER VALUE: NONE |
| | CONSTRAINT CONDITION: NONE |

FIG. 4

EXECUTION PERFORMANCE RESULT AND EVALUATION PERFORMANCE RESULT 2 ACCORDING TO PREVIOUS EXECUTION PROCEDURE

| | |
|---|---|
| C1 | 1. CULTURE-RELATED PROCESS |
| 26a | 1-1. OPERATION: ADJUSTMENT OF DIFFERENTIATION-INDUCING CULTURE MEDIUM A |
| 26b | input: BASAL CULTURE MEDIUM, BMP4, VEGF |
| 26c | output: DIFFERENTIATION-INDUCING CULTURE MEDIUM A |
| 26d | EXECUTION PARAMETER VALUE: BASAL CULTURE MEDIUM CONCENTRATION 10 mM, BMP4 CONCENTRATION: 2 μM, VEGF CONCENTRATION: 5 μM, GLUCOSE CONCENTRATION: 11 μM |
| 26e | CONSTRAINT CONDITION: NONE |
| C2 | 1-2. OPERATION: CELL CULTURE USING DIFFERENTIATION-INDUCING CULTURE MEDIUM A (INTENDED CELL INDUCTION) |
| | input: DIFFERENTIATION-INDUCING CULTURE MEDIUM A (ADJUSTED), HUMAN iPS CELLS (HPS0003 STRAIN) |
| | output: HUMAN iPS CELLS (HPS0003 STRAIN) (BEING IN MIDDLE OF DIFFERENTIATION) |
| | EXECUTION PARAMETER VALUE: CULTURE PERIOD: 6 DAYS |
| | CONSTRAINT CONDITION: WITHIN 60 MINUTES AFTER ADJUSTMENT OF DIFFERENTIATION-INDUCING CULTURE MEDIUM A IS FINISHED |
| C3 | 1-3. OPERATION: ADJUSTMENT OF DIFFERENTIATION-INDUCING CULTURE MEDIUM B |
| | input: DIFFERENTIATION-INDUCING BASAL CULTURE MEDIUM, BMP4, VEGF, SCF |
| | output: DIFFERENTIATION-INDUCING CULTURE MEDIUM B |
| | EXECUTION PARAMETER VALUE: BASAL CULTURE MEDIUM CONCENTRATION 10 mM, BMP4 CONCENTRATION: 2 μM, VEGF CONCENTRATION: 4 μM, SCF CONCENTRATION: 10 μM |
| C4 | CONSTRAINT CONDITION: NONE |
| | 1-4. OPERATION: CELL CULTURE USING DIFFERENTIATION-INDUCING CULTURE MEDIUM B (INTENDED CELL DIFFERENTIATION) |
| | input: DIFFERENTIATION-INDUCING CULTURE MEDIUM B (ADJUSTED), HUMAN iPS CELLS (HPS0003 STRAIN) (CULTURED IN DIFFERENTIATION-INDUCING CULTURE MEDIUM A AND BEING IN MIDDLE OF DIFFERENTIATION) |
| | output: HUMAN iPS CELLS (HPS0003 STRAIN) AFTER INDUCTION OF DIFFERENTIATION |
| | EXECUTION PARAMETER VALUE: CULTURE PERIOD: 6 DAYS |
| | CONSTRAINT CONDITION: WITHIN 60 MINUTES AFTER ADJUSTMENT OF DIFFERENTIATION-INDUCING CULTURE MEDIUM B IS FINISHED |
| C5 | 2. EVALUATION PROCESS |
| | 2-1. MARKER GENE EXPRESSION EVALUATION |
| | input: HUMAN iPS CELLS (HPS0003 STRAIN) AFTER INDUCTION OF DIFFERENTIATION |
| | output: MARKER GENE EXPRESSION POSITIVE RATE 43% |
| | EXECUTION PARAMETER VALUE: NONE |
| | CONSTRAINT CONDITION: NONE |

FIG. 5

| TEMPLATE EXECUTION PROCEDURE |
|---|
| C1 1. CULTURE-RELATED PROCESS |
| 26a 1-1. OPERATION: ADJUSTMENT OF DIFFERENTIATION-INDUCING CULTURE MEDIUM A |
| 26b input: BASAL CULTURE MEDIUM, BMP4, VEGF |
| 26c output: DIFFERENTIATION-INDUCING CULTURE MEDIUM A |
| 26d EXECUTION PARAMETER VALUE: BASAL CULTURE MEDIUM CONCENTRATION 10 mM |
| 26g VARIABLE PARAMETER VALUE: 0 < BMP4 CONCENTRATION < 10 µM, 0 µM < VEGF CONCENTRATION < 15 µM, 3 µM < GLUCOSE CONCENTRATION < 15 µM |
| 26e CONSTRAINT CONDITION: NONE |
| C2 1-2. OPERATION: CELL CULTURE USING DIFFERENTIATION-INDUCING CULTURE MEDIUM A (INTENDED CELL INDUCTION) |
| input: DIFFERENTIATION-INDUCING CULTURE MEDIUM A (ADJUSTED), HUMAN iPS CELLS (HPS0003 STRAIN) |
| output: HUMAN iPS CELLS (HPS0003 STRAIN) (BEING IN MIDDLE OF DIFFERENTIATION) |
| EXECUTION PARAMETER VALUE: CULTURE PERIOD: 6 DAYS |
| CONSTRAINT CONDITION: WITHIN 60 MINUTES AFTER ADJUSTMENT OF DIFFERENTIATION-INDUCING CULTURE MEDIUM A IS FINISHED |
| C3 1-3. OPERATION: ADJUSTMENT OF DIFFERENTIATION-INDUCING CULTURE MEDIUM B |
| input: DIFFERENTIATION-INDUCING BASAL CULTURE MEDIUM, BMP4, VEGF, SCF |
| output: DIFFERENTIATION-INDUCING CULTURE MEDIUM B |
| EXECUTION PARAMETER VALUE: BASAL CULTURE MEDIUM CONCENTRATION 10 mM, BMP4 CONCENTRATION: 2 µM, VEGF CONCENTRATION: 4 µM, SCF CONCENTRATION: 10 µM |
| CONSTRAINT CONDITION: NONE |
| C4 1-4. OPERATION: CELL CULTURE USING DIFFERENTIATION-INDUCING CULTURE MEDIUM B (INTENDED CELL DIFFERENTIATION) |
| input: DIFFERENTIATION-INDUCING CULTURE MEDIUM B (ADJUSTED), HUMAN iPS CELLS (HPS0003 STRAIN) (CULTURED IN DIFFERENTIATION-INDUCING CULTURE MEDIUM A AND BEING IN MIDDLE OF DIFFERENTIATION) |
| output: HUMAN iPS CELLS (HPS0003 STRAIN) AFTER INDUCTION OF DIFFERENTIATION |
| EXECUTION PARAMETER VALUE: CULTURE PERIOD: 6 DAYS |
| CONSTRAINT CONDITION: WITHIN 60 MINUTES AFTER ADJUSTMENT OF DIFFERENTIATION-INDUCING CULTURE MEDIUM B IS FINISHED |
| C5 2. EVALUATION PROCESS |
| 2-1. MARKER GENE EXPRESSION EVALUATION |
| input: HUMAN iPS CELLS (HPS0003 STRAIN) AFTER INDUCTION OF DIFFERENTIATION |
| output: MARKER GENE EXPRESSION POSITIVE RATE |
| EXECUTION PARAMETER VALUE: NONE |
| CONSTRAINT CONDITION: NONE |

FIG. 6

| | EXECUTION PROCEDURE 1 |
|---|---|
| C1 | 1. CULTURE-RELATED PROCESS |
| 26a | 1-1. OPERATION: ADJUSTMENT OF DIFFERENTIATION-INDUCING CULTURE MEDIUM A |
| 26b | input: BASAL CULTURE MEDIUM, BMP4, VEGF, GLUCOSE |
| 26c | output: DIFFERENTIATION-INDUCING CULTURE MEDIUM A |
| 26d | EXECUTION PARAMETER VALUE: BASAL CULTURE MEDIUM CONCENTRATION 10 mM |
| 26g | VARIABLE PARAMETER VALUE: BMP4 CONCENTRATION = 5 µM, VEGF CONCENTRATION = 10 µM, GLUCOSE CONCENTRATION = 11 µM |
| 26e | CONSTRAINT CONDITION: NONE |
| C2 | 1-2. OPERATION: CELL CULTURE USING DIFFERENTIATION-INDUCING CULTURE MEDIUM A (INTENDED CELL INDUCTION) |
| | input: DIFFERENTIATION-INDUCING CULTURE MEDIUM A (ADJUSTED), HUMAN iPS CELLS (HPS0003 STRAIN) |
| | output: HUMAN iPS CELLS (HPS0003 STRAIN) (BEING IN MIDDLE OF DIFFERENTIATION) |
| | EXECUTION PARAMETER VALUE: CULTURE PERIOD: 6 DAYS |
| | CONSTRAINT CONDITION: WITHIN 60 MINUTES AFTER ADJUSTMENT OF DIFFERENTIATION-INDUCING CULTURE MEDIUM A IS FINISHED |
| C3 | 1-3. OPERATION: ADJUSTMENT OF DIFFERENTIATION-INDUCING CULTURE MEDIUM B |
| | input: DIFFERENTIATION-INDUCING BASAL CULTURE MEDIUM, BMP4, VEGF, SCF |
| | output: DIFFERENTIATION-INDUCING CULTURE MEDIUM B |
| | EXECUTION PARAMETER VALUE: BASAL CULTURE MEDIUM CONCENTRATION 10 mM, BMP4 CONCENTRATION: 8 µM, VEGF CONCENTRATION: 8 µM, SCF CONCENTRATION: 12 µM |
| C4 | CONSTRAINT CONDITION: NONE |
| | 1-4. OPERATION: CELL CULTURE USING DIFFERENTIATION-INDUCING CULTURE MEDIUM B (INTENDED CELL DIFFERENTIATION) |
| | input: DIFFERENTIATION-INDUCING CULTURE MEDIUM B (ADJUSTED), HUMAN iPS CELLS (HPS0003 STRAIN) (CULTURED IN DIFFERENTIATION-INDUCING CULTURE MEDIUM A AND BEING IN MIDDLE OF DIFFERENTIATION) |
| | output: HUMAN iPS CELLS (HPS0003 STRAIN) AFTER INDUCTION OF DIFFERENTIATION |
| | EXECUTION PARAMETER VALUE: CULTURE PERIOD: 6 DAYS |
| | CONSTRAINT CONDITION: WITHIN 60 MINUTES AFTER ADJUSTMENT OF DIFFERENTIATION-INDUCING CULTURE MEDIUM B IS FINISHED |
| C5 | 2. EVALUATION PROCESS |
| | 2-1. MARKER GENE EXPRESSION EVALUATION |
| | input: HUMAN iPS CELLS (HPS0003 STRAIN) AFTER INDUCTION OF DIFFERENTIATION |
| | output: MARKER GENE EXPRESSION POSITIVE RATE (0% TO 100%) |
| | EXECUTION PARAMETER VALUE: NONE |
| | CONSTRAINT CONDITION: NONE |

FIG. 7

| | EXECUTION PROCEDURE 2 |
|---|---|
| C1 | 1. CULTURE-RELATED PROCESS |
| 26a | 1-1. OPERATION: ADJUSTMENT OF DIFFERENTIATION-INDUCING CULTURE MEDIUM A |
| 26b | input: BASAL CULTURE MEDIUM, BMP4, VEGF, GLUCOSE |
| 26c | output: DIFFERENTIATION-INDUCING CULTURE MEDIUM A |
| 26d | EXECUTION PARAMETER VALUE: BASAL CULTURE MEDIUM CONCENTRATION 10 mM |
| 26g | VARIABLE PARAMETER VALUE: BMP4 CONCENTRATION = 6 μM, VEGF CONCENTRATION = 8 μM, GLUCOSE CONCENTRATION = 6 μM |
| 26e | CONSTRAINT CONDITION: NONE |
| C2 | 1-2. OPERATION: CELL CULTURE USING DIFFERENTIATION-INDUCING CULTURE MEDIUM A (INTENDED CELL INDUCTION) |
| | input: DIFFERENTIATION-INDUCING CULTURE MEDIUM A (ADJUSTED), HUMAN iPS CELLS (HPS0003 STRAIN) |
| | output: HUMAN iPS CELLS (HPS0003 STRAIN) (BEING IN MIDDLE OF DIFFERENTIATION) |
| | EXECUTION PARAMETER VALUE: CULTURE PERIOD: 6 DAYS |
| | CONSTRAINT CONDITION: WITHIN 60 MINUTES AFTER ADJUSTMENT OF DIFFERENTIATION-INDUCING CULTURE MEDIUM A IS FINISHED |
| C3 | 1-3. OPERATION: ADJUSTMENT OF DIFFERENTIATION-INDUCING CULTURE MEDIUM B |
| | input: DIFFERENTIATION-INDUCING BASAL CULTURE MEDIUM, BMP4, VEGF, SCF |
| | output: DIFFERENTIATION-INDUCING CULTURE MEDIUM B |
| | EXECUTION PARAMETER VALUE: BASAL CULTURE MEDIUM CONCENTRATION 10 mM, BMP4 CONCENTRATION: 8 μM, VEGF CONCENTRATION: 8 μM, SCF CONCENTRATION: 12 μM |
| C4 | CONSTRAINT CONDITION: NONE |
| | 1-4. OPERATION: CELL CULTURE USING DIFFERENTIATION-INDUCING CULTURE MEDIUM B (INTENDED CELL DIFFERENTIATION) |
| | input: DIFFERENTIATION-INDUCING CULTURE MEDIUM B (ADJUSTED), HUMAN iPS CELLS (HPS0003 STRAIN) (CULTURED IN DIFFERENTIATION-INDUCING CULTURE MEDIUM A AND BEING IN MIDDLE OF DIFFERENTIATION) |
| | output: HUMAN iPS CELLS (HPS0003 STRAIN) AFTER INDUCTION OF DIFFERENTIATION |
| | EXECUTION PARAMETER VALUE: CULTURE PERIOD: 6 DAYS |
| | CONSTRAINT CONDITION: WITHIN 60 MINUTES AFTER ADJUSTMENT OF DIFFERENTIATION-INDUCING CULTURE MEDIUM B IS FINISHED |
| C5 | 2. EVALUATION PROCESS |
| | 2-1. MARKER GENE EXPRESSION EVALUATION |
| | input: HUMAN iPS CELLS (HPS0003 STRAIN) AFTER INDUCTION OF DIFFERENTIATION |
| | output: MARKER GENE EXPRESSION POSITIVE RATE (0% TO 100%) |
| | EXECUTION PARAMETER VALUE: NONE |
| | CONSTRAINT CONDITION: NONE |

FIG. 10A

| EXECUTION SUBJECT | ADJUSTMENT OF DIFFERENTIATION-INDUCING CULTURE MEDIUM A | CULTURE USING DIFFERENTIATION-INDUCING CULTURE MEDIUM A | ADJUSTMENT OF DIFFERENTIATION-INDUCING CULTURE MEDIUM B | CULTURE USING DIFFERENTIATION-INDUCING CULTURE MEDIUM B | MARKER GENE EXPRESSION EVALUATION | USAGE CIRCUMSTANCES |
|---|---|---|---|---|---|---|
| CULTURE MEDIUM MIXING DEVICE | ○ 30 MINUTES | × | ○ 30 MINUTES | × | × | |
| CELL CULTURE DEVICE X | × | ○ 6 DAYS (SET CULTURE TIME) | × | ○ 6 DAYS (SET CULTURE TIME) | × | 2020/1/3 17:00 -2020/1/6 17:00 |
| CELL CULTURE DEVICE Y | × | ○ 6 DAYS (SET CULTURE TIME) | × | ○ 6 DAYS (SET CULTURE TIME) | × | 2020/1/12 17:00 -2020/1/15 17:00 |
| FLOW CYTOMETER | × | × | × | × | ○ 60 MINUTES | |

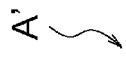

| No. | ADJUSTMENT OF DIFFERENTIATION-INDUCING CULTURE MEDIUM A | CULTURE USING DIFFERENTIATION-INDUCING CULTURE MEDIUM A | ADJUSTMENT OF DIFFERENTIATION-INDUCING CULTURE MEDIUM B | CULTURE USING DIFFERENTIATION-INDUCING CULTURE MEDIUM B | MARKER GENE EXPRESSION EVALUATION |
|---|---|---|---|---|---|
| 1 | CULTURE MEDIUM MIXING DEVICE P | CELL CULTURE DEVICE X | CULTURE MEDIUM MIXING DEVICE P | CELL CULTURE DEVICE X | FLOW CYTOMETER Q |
| 2 | CULTURE MEDIUM MIXING DEVICE P | CELL CULTURE DEVICE X | CULTURE MEDIUM MIXING DEVICE P | CELL CULTURE DEVICE Y | FLOW CYTOMETER Q |
| 3 | CULTURE MEDIUM MIXING DEVICE P | CELL CULTURE DEVICE Y | CULTURE MEDIUM MIXING DEVICE P | CELL CULTURE DEVICE X | FLOW CYTOMETER Q |
| 4 | CULTURE MEDIUM MIXING DEVICE P | CELL CULTURE DEVICE Y | CULTURE MEDIUM MIXING DEVICE P | CELL CULTURE DEVICE Y | FLOW CYTOMETER Q |

FIG. 15

| No. | ADJUSTMENT OF DIFFERENTIATION-INDUCING CULTURE MEDIUM A | CULTURE USING DIFFERENTIATION-INDUCING CULTURE MEDIUM A | ADJUSTMENT OF DIFFERENTIATION-INDUCING CULTURE MEDIUM B | CULTURE USING DIFFERENTIATION-INDUCING CULTURE MEDIUM B | MARKER GENE EXPRESSION EVALUATION |
|---|---|---|---|---|---|
| 1 | CULTURE MEDIUM MIXING DEVICE P<br>2020/1/2/8:30<br>-2020/1/2/9:00 | CELL CULTURE DEVICE X<br>2020/1/7/17:00<br>-2020/1/13/17:00 | CULTURE MEDIUM MIXING DEVICE P<br>2020/1/13/16:30<br>-2020/1/13/17:00 | CELL CULTURE DEVICE X<br>2020/1/13/17:00<br>-2020/1/19/17:00 | FLOW CYTOMETER Q<br>2020/1/19/17:00<br>-2020/1/19/18:00 |
| 2 | CULTURE MEDIUM MIXING DEVICE P<br>2020/1/2/8:30<br>-2020/1/2/9:00 | CELL CULTURE DEVICE X<br>2020/1/7/17:00<br>-2020/1/13/17:00 | CULTURE MEDIUM MIXING DEVICE P<br>2020/1/15/16:30<br>-2020/1/15/17:00 | CELL CULTURE DEVICE Y<br>2020/1/15/17:00<br>-2020/1/21/17:00 | FLOW CYTOMETER Q<br>2020/1/21/17:00<br>-2020/1/21/18:00 |
| 3 | CULTURE MEDIUM MIXING DEVICE P<br>2020/1/2/8:30<br>-2020/1/2/9:00 | CELL CULTURE DEVICE X<br>2020/1/7/17:00<br>-2020/1/13/17:00 | CULTURE MEDIUM MIXING DEVICE P<br>2020/1/13/17:00<br>-2020/1/13/17:30 | CELL CULTURE DEVICE Y<br>2020/1/15/17:00<br>-2020/1/21/17:00 | FLOW CYTOMETER Q<br>2020/1/21/17:00<br>-2020/1/21/18:00 |
| 4 | CULTURE MEDIUM MIXING DEVICE P<br>2020/1/2/8:30<br>-2020/1/2/9:00 | CELL CULTURE DEVICE Y<br>2020/1/2/9:00<br>-2020/1/8/9:00 | CULTURE MEDIUM MIXING DEVICE P<br>2020/1/8/8:30<br>-2020/1/8/9:00 | CELL CULTURE DEVICE X<br>2020/1/8/9:00<br>-2020/1/14/9:00 | FLOW CYTOMETER Q<br>2020/1/14/9:00<br>-2020/1/14/10:00 |
| 5 | CULTURE MEDIUM MIXING DEVICE P<br>2020/1/2/8:30<br>-2020/1/2/9:00 | CELL CULTURE DEVICE Y<br>2020/1/2/9:00<br>-2020/1/8/9:00 | CULTURE MEDIUM MIXING DEVICE P<br>2020/1/2/8:30<br>-2020/1/2/9:00 | CELL CULTURE DEVICE Y<br>2020/1/15/17:00<br>-2020/1/21/17:00 | FLOW CYTOMETER Q<br>2020/1/21/17:00<br>-2020/1/21/18:00 |

| No. | ADJUSTMENT OF DIFFERENTIATION-INDUCING CULTURE MEDIUM A | CULTURE USING DIFFERENTIATION-INDUCING CULTURE MEDIUM A | ADJUSTMENT OF DIFFERENTIATION-INDUCING CULTURE MEDIUM B | CULTURE USING DIFFERENTIATION-INDUCING CULTURE MEDIUM B | MARKER GENE EXPRESSION EVALUATION |
|---|---|---|---|---|---|
| 1 | CULTURE MEDIUM MIXING DEVICE P 2020/1/2/8:30 -2020/1/2/9:00 | CELL CULTURE DEVICE X 2020/1/7/17:00 -2020/1/13/17:00 | CULTURE MEDIUM MIXING DEVICE P 2020/1/13/16:30 -2020/1/13/17:00 | CELL CULTURE DEVICE X 2020/1/13/17:00 -2020/1/19/17:00 | FLOW CYTOMETER Q 2020/1/19/17:00 -2020/1/19/18:00 |
| 2 | CULTURE MEDIUM MIXING DEVICE P 2020/1/2/8:30 -2020/1/2/9:00 | CELL CULTURE DEVICE X 2020/1/7/17:00 -2020/1/13/17:00 | CULTURE MEDIUM MIXING DEVICE P 2020/1/15/16:30 -2020/1/15/17:00 | CELL CULTURE DEVICE Y 2020/1/15/17:00 -2020/1/21/17:00 | FLOW CYTOMETER Q 2020/1/21/17:00 -2020/1/21/18:00 |
| 3 | CULTURE MEDIUM MIXING DEVICE P 2020/1/2/8:30 -2020/1/2/9:00 | CELL CULTURE DEVICE X 2020/1/7/17:00 -2020/1/13/17:00 | CULTURE MEDIUM MIXING DEVICE P 2020/1/13/17:00 -2020/1/13/17:30 | CELL CULTURE DEVICE Y 2020/1/15/17:00 -2020/1/21/17:00 | FLOW CYTOMETER Q 2020/1/21/17:00 -2020/1/21/18:00 |
| 4 | CULTURE MEDIUM MIXING DEVICE P 2020/1/2/8:30 -2020/1/2/9:00 | CELL CULTURE DEVICE Y 2020/1/2/9:00 -2020/1/8/9:00 | CULTURE MEDIUM MIXING DEVICE P 2020/1/8/8:30 -2020/1/8/9:00 | CELL CULTURE DEVICE X 2020/1/8/9:00 -2020/1/14/9:00 | FLOW CYTOMETER Q 2020/1/14/9:00 -2020/1/14/10:00 |
| 5 | CULTURE MEDIUM MIXING DEVICE P 2020/1/2/8:30 -2020/1/2/9:00 | CELL CULTURE DEVICE Y 2020/1/2/9:00 -2020/1/8/9:00 | CULTURE MEDIUM MIXING DEVICE P 2020/1/8/8:30 -2020/1/8/9:00 | CELL CULTURE DEVICE Y 2020/1/15/17:00 -2020/1/21/17:00 | FLOW CYTOMETER Q 2020/1/21/17:00 -2020/1/21/18:00 |

FIG. 19

| | STARTING POINT EXECUTION PROCEDURE |
|---|---|
| C6 | 1. CULTURE-RELATED PROCESS |
| | 1-1. OPERATION: ADJUSTMENT OF DIFFERENTIATION-INDUCING CULTURE MEDIUM A |
| 26a | |
| 26b | input: BASAL CULTURE MEDIUM, BMP4, VEGF |
| 26c | output: DIFFERENTIATION-INDUCING CULTURE MEDIUM A |
| 26d | EXECUTION PARAMETER VALUE: BASAL CULTURE MEDIUM CONCENTRATION 10 mM, BMP4 CONCENTRATION: 2 µM, VEGF CONCENTRATION: 5 µM, GLUCOSE CONCENTRATION: 4 µM |
| 26e | CONSTRAINT CONDITION: NONE |
| C7 | 1-2. OPERATION: CELL CULTURE USING DIFFERENTIATION-INDUCING CULTURE MEDIUM A (INTENDED CELL INDUCTION) |
| | input: DIFFERENTIATION-INDUCING CULTURE MEDIUM A, HUMAN iPS CELLS (HPS0003 STRAIN) |
| | output: HUMAN iPS CELLS (HPS0003 STRAIN) (BEING IN MIDDLE OF DIFFERENTIATION) |
| | EXECUTION PARAMETER VALUE: CULTURE PERIOD: 6 DAYS |
| | CONSTRAINT CONDITION: WITHIN 60 MINUTES AFTER ADJUSTMENT OF DIFFERENTIATION-INDUCING CULTURE MEDIUM A IS FINISHED |
| C8 | 1-3. OPERATION: ADJUSTMENT OF DIFFERENTIATION-INDUCING CULTURE MEDIUM B |
| | input: DIFFERENTIATION-INDUCING BASAL CULTURE MEDIUM (ADJUSTED), BMP4, VEGF, SCF |
| | output: DIFFERENTIATION-INDUCING CULTURE MEDIUM B |
| | EXECUTION PARAMETER VALUE: BASAL CULTURE MEDIUM CONCENTRATION 10 mM, BMP4 CONCENTRATION: 2 µM, VEGF CONCENTRATION: 4 µM, SCF CONCENTRATION: 10 µM |
| | CONSTRAINT CONDITION: NONE |
| C9 | 1-4. OPERATION: CELL CULTURE USING DIFFERENTIATION-INDUCING CULTURE MEDIUM B (INTENDED CELL DIFFERENTIATION) |
| | input: DIFFERENTIATION-INDUCING CULTURE MEDIUM B (ADJUSTED), HUMAN iPS CELLS (HPS0009 STRAIN) (CULTURED IN DIFFERENTIATION-INDUCING CULTURE MEDIUM A AND BEING IN MIDDLE OF DIFFERENTIATION) |
| | output: HUMAN iPS CELLS (HPS0003 STRAIN) AFTER INDUCTION OF DIFFERENTIATION |
| | EXECUTION PARAMETER VALUE: CULTURE PERIOD: 6 DAYS |
| | CONSTRAINT CONDITION: WITHIN 60 MINUTES AFTER ADJUSTMENT OF DIFFERENTIATION-INDUCING CULTURE MEDIUM B IS FINISHED |
| C10 | 2. EVALUATION PROCESS |
| | 2-1. MARKER GENE EXPRESSION EVALUATION |
| | input: HUMAN iPS CELLS (HPS0003 STRAIN) AFTER INDUCTION OF DIFFERENTIATION |
| | output: MARKER GENE EXPRESSION POSITIVE RATE (0% TO 100%) |
| | EXECUTION PARAMETER VALUE: NONE |
| | CONSTRAINT CONDITION: NONE |

FIG. 20

| | |
|---|---|
| | PREVIOUS RELEVANT EXECUTION PROCEDURE: EXECUTION PROCEDURE A |
| C6 | 1. CULTURE-RELATED PROCESS |
| 26a | 1-1. OPERATION: ADJUSTMENT OF DIFFERENTIATION-INDUCING CULTURE MEDIUM A |
| 26b | input: BASAL CULTURE MEDIUM, BMP4, VEGF |
| 26c | output: DIFFERENTIATION-INDUCING CULTURE MEDIUM A |
| 26d | EXECUTION PARAMETER VALUE: BASAL CULTURE MEDIUM CONCENTRATION 10 mM, BMP4 CONCENTRATION: 2 μM, VEGF CONCENTRATION: 5 μM, GLUCOSE CONCENTRATION: 4 μM |
| 26e | CONSTRAINT CONDITION: NONE |
| C12 | 1-2. OPERATION: CELL CULTURE USING DIFFERENTIATION-INDUCING CULTURE MEDIUM A (INTENDED CELL INDUCTION) |
| | input: DIFFERENTIATION-INDUCING CULTURE MEDIUM A (ADJUSTED), HUMAN iPS CELLS (HPS0003 STRAIN) |
| | output: HUMAN iPS CELLS (HPS0003 STRAIN) (BEING IN MIDDLE OF DIFFERENTIATION) |
| | EXECUTION PARAMETER VALUE: CULTURE PERIOD: 6 DAYS |
| | CONSTRAINT CONDITION: WITHIN 60 MINUTES AFTER ADJUSTMENT OF DIFFERENTIATION-INDUCING CULTURE MEDIUM A IS FINISHED |
| C13 | 2. EVALUATION PROCESS |
| | 2-1. MARKER GENE EXPRESSION EVALUATION |
| | input: HUMAN iPS CELLS (HPS0003 STRAIN) AFTER INDUCTION OF DIFFERENTIATION |
| | output: MARKER GENE EXPRESSION POSITIVE RATE (0% TO 100%) |
| | EXECUTION PARAMETER VALUE: NONE |
| | CONSTRAINT CONDITION: NONE |

FIG. 21

| | |
|---|---|
| | PREVIOUS RELEVANT EXECUTION PROCEDURE: EXECUTION PROCEDURE B |
| C6 | 1. CULTURE-RELATED PROCESS |
| 26a | 1-1. OPERATION: ADJUSTMENT OF DIFFERENTIATION-INDUCING CULTURE MEDIUM A |
| 26b | input: BASAL CULTURE MEDIUM, BMP4, VEGF |
| 26c | output: DIFFERENTIATION-INDUCING CULTURE MEDIUM A |
| 26d | EXECUTION PARAMETER VALUE: BASAL CULTURE MEDIUM CONCENTRATION 10 mM, BMP4 CONCENTRATION: 2 µM, VEGF CONCENTRATION: 5 µM, GLUCOSE CONCENTRATION: 4 µM |
| 26e | CONSTRAINT CONDITION: NONE |
| C12 | 1-2. OPERATION: CELL CULTURE USING DIFFERENTIATION-INDUCING CULTURE MEDIUM A (INTENDED CELL INDUCTION) |
| | input: DIFFERENTIATION-INDUCING CULTURE MEDIUM A (ADJUSTED), HUMAN iPS CELLS (HPS0009 STRAIN) |
| | output: HUMAN iPS CELLS (HPS0009 STRAIN) (BEING IN MIDDLE OF DIFFERENTIATION) |
| | EXECUTION PARAMETER VALUE: CULTURE PERIOD: 6 DAYS |
| | CONSTRAINT CONDITION: WITHIN 60 MINUTES AFTER ADJUSTMENT OF DIFFERENTIATION-INDUCING CULTURE MEDIUM A IS FINISHED |
| C13 | 1-3. OPERATION: ADJUSTMENT OF DIFFERENTIATION-INDUCING CULTURE MEDIUM B |
| | input: DIFFERENTIATION-INDUCING BASAL CULTURE MEDIUM, BMP4, VEGF, SCF |
| | output: DIFFERENTIATION-INDUCING CULTURE MEDIUM B |
| | EXECUTION PARAMETER VALUE: BASAL CULTURE MEDIUM CONCENTRATION 10 mM, BMP4 CONCENTRATION: 2 µM, VEGF CONCENTRATION: 4 µM, SCF CONCENTRATION: 10 µM |
| C14 | CONSTRAINT CONDITION: NONE |
| | 1-4. OPERATION: CELL CULTURE USING DIFFERENTIATION-INDUCING CULTURE MEDIUM B (INTENDED CELL DIFFERENTIATION) |
| | input: DIFFERENTIATION-INDUCING CULTURE MEDIUM B (ADJUSTED), HUMAN iPS CELLS (HPS0009 STRAIN) (CULTURED IN DIFFERENTIATION-INDUCING CULTURE MEDIUM A AND BEING IN MIDDLE OF DIFFERENTIATION) |
| | output: HUMAN iPS CELLS (HPS0009 STRAIN) AFTER INDUCTION OF DIFFERENTIATION |
| | EXECUTION PARAMETER VALUE: CULTURE PERIOD: 6 DAYS |
| | CONSTRAINT CONDITION: WITHIN 60 MINUTES AFTER ADJUSTMENT OF DIFFERENTIATION-INDUCING CULTURE MEDIUM B IS FINISHED |
| C15 | 2. EVALUATION PROCESS |
| | 2-1. MARKER GENE EXPRESSION EVALUATION |
| | input: HUMAN iPS CELLS (HPS0009 STRAIN) AFTER INDUCTION OF DIFFERENTIATION |
| | output: MARKER GENE EXPRESSION POSITIVE RATE (0% TO 100%) |
| | EXECUTION PARAMETER VALUE: NONE |
| | CONSTRAINT CONDITION: NONE |

FIG. 22

EVALUATION PERFORMANCE RESULT OF PREVIOUS RELEVANT EXECUTION PROCEDURE

| |
|---|
| EXECUTION PROCEDURE A: MARKER GENE EXPRESSION POSITIVE RATE: 65% |
| EXECUTION PROCEDURE B: MARKER GENE EXPRESSION POSITIVE RATE: 82% |

FIG. 23

| | TEMPLATE EXECUTION PROCEDURE |
|---|---|
| C6 | 1. CULTURE-RELATED PROCESS |
| 26a | 1-1. OPERATION: ADJUSTMENT OF DIFFERENTIATION-INDUCING CULTURE MEDIUM A |
| 26b | input: BASAL CULTURE MEDIUM, BMP4, VEGF |
| 26c | output: DIFFERENTIATION-INDUCING CULTURE MEDIUM A |
| 26d | EXECUTION PARAMETER VALUE: BASAL CULTURE MEDIUM CONCENTRATION 10 mM |
| 26j | VARIABLE PARAMETER VALUE: 0 µM < BMP4 CONCENTRATION < 10 µM, 0 µM < VEGF CONCENTRATION < 15 µM, 3 µM < GLUCOSE CONCENTRATION < 15 µM |
| 26e | CONSTRAINT CONDITION: NONE |
| C7 | 1-2. OPERATION: CELL CULTURE USING DIFFERENTIATION-INDUCING CULTURE MEDIUM A (INTENDED CELL INDUCTION) |
| | input: DIFFERENTIATION-INDUCING CULTURE MEDIUM A (ADJUSTED), HUMAN iPS CELLS (HPS0003 STRAIN) |
| | output: HUMAN iPS CELLS (HPS0003 STRAIN) (BEING IN MIDDLE OF DIFFERENTIATION) |
| | EXECUTION PARAMETER VALUE: CULTURE PERIOD: 6 DAYS |
| | CONSTRAINT CONDITION: WITHIN 60 MINUTES AFTER ADJUSTMENT OF DIFFERENTIATION-INDUCING CULTURE MEDIUM A IS FINISHED |
| C8 | 1-3. OPERATION: ADJUSTMENT OF DIFFERENTIATION-INDUCING CULTURE MEDIUM B |
| | input: DIFFERENTIATION-INDUCING BASAL CULTURE MEDIUM, BMP4, VEGF, SCF |
| | output: DIFFERENTIATION-INDUCING CULTURE MEDIUM B |
| | EXECUTION PARAMETER VALUE: BASAL CULTURE MEDIUM CONCENTRATION 10 mM, BMP4 CONCENTRATION: 2 µM, VEGF CONCENTRATION: 4 µM, SCF CONCENTRATION: 10 µM |
| | CONSTRAINT CONDITION: NONE |
| C9 | 1-4. OPERATION: CELL CULTURE USING DIFFERENTIATION-INDUCING CULTURE MEDIUM B (INTENDED CELL DIFFERENTIATION) |
| | input: DIFFERENTIATION-INDUCING CULTURE MEDIUM B (ADJUSTED), HUMAN iPS CELLS (HPS0003 STRAIN) (CULTURED IN DIFFERENTIATION-INDUCING CULTURE MEDIUM A AND BEING IN MIDDLE OF DIFFERENTIATION) |
| | output: HUMAN iPS CELLS (HPS0003 STRAIN) AFTER INDUCTION OF DIFFERENTIATION |
| | EXECUTION PARAMETER VALUE: CULTURE PERIOD: 6 DAYS |
| | CONSTRAINT CONDITION: WITHIN 60 MINUTES AFTER ADJUSTMENT OF DIFFERENTIATION-INDUCING CULTURE MEDIUM B IS FINISHED |
| C10 | 2. EVALUATION PROCESS |
| | 2-1. MARKER GENE EXPRESSION EVALUATION |
| | input: HUMAN iPS CELLS (HPS0003 STRAIN) AFTER INDUCTION OF DIFFERENTIATION |
| | output: MARKER GENE EXPRESSION POSITIVE RATE |
| | EXECUTION PARAMETER VALUE: NONE |
| | CONSTRAINT CONDITION: NONE |

FIG. 24

| | |
|---|---|
| | EXECUTION PROCEDURE 1 |
| C6 | 1. CULTURE-RELATED PROCESS |
| 26a | 1-1. OPERATION: ADJUSTMENT OF DIFFERENTIATION-INDUCING CULTURE MEDIUM A |
| 26b | input: BASAL CULTURE MEDIUM, BMP4, VEGF, GLUCOSE |
| 26c | output: DIFFERENTIATION-INDUCING CULTURE MEDIUM A |
| 26d | EXECUTION PARAMETER VALUE: BASAL CULTURE MEDIUM CONCENTRATION 10 mM |
| 26j | VARIABLE PARAMETER VALUE: BMP4 CONCENTRATION = 5 μM, VEGF CONCENTRATION = 10 μM, GLUCOSE CONCENTRATION = 11 μM |
| 26e | CONSTRAINT CONDITION: NONE |
| C7 | 1-2. OPERATION: CELL CULTURE USING DIFFERENTIATION-INDUCING CULTURE MEDIUM A (INTENDED CELL INDUCTION) |
| | input: DIFFERENTIATION-INDUCING CULTURE MEDIUM A (ADJUSTED), HUMAN iPS CELLS (HPS0003 STRAIN) |
| | output: HUMAN iPS CELLS (HPS0003 STRAIN) (BEING IN MIDDLE OF DIFFERENTIATION) |
| | EXECUTION PARAMETER VALUE: CULTURE PERIOD: 6 DAYS |
| | CONSTRAINT CONDITION: WITHIN 60 MINUTES AFTER ADJUSTMENT OF DIFFERENTIATION-INDUCING CULTURE MEDIUM A IS FINISHED |
| C8 | 1-3. OPERATION: ADJUSTMENT OF DIFFERENTIATION-INDUCING CULTURE MEDIUM B |
| | input: DIFFERENTIATION-INDUCING BASAL CULTURE MEDIUM, BMP4, VEGF, SCF |
| | output: DIFFERENTIATION-INDUCING CULTURE MEDIUM B |
| | EXECUTION PARAMETER VALUE: BASAL CULTURE MEDIUM CONCENTRATION 10 mM, BMP4 CONCENTRATION: 8 μM, VEGF CONCENTRATION: 8 μM, SCF CONCENTRATION: 12 μM |
| C9 | CONSTRAINT CONDITION: NONE |
| | 1-4. OPERATION: CELL CULTURE USING DIFFERENTIATION-INDUCING CULTURE MEDIUM B (INTENDED CELL DIFFERENTIATION) |
| | input: DIFFERENTIATION-INDUCING CULTURE MEDIUM B (ADJUSTED), HUMAN iPS CELLS (HPS0003 STRAIN) (CULTURED IN DIFFERENTIATION-INDUCING CULTURE MEDIUM A AND BEING IN MIDDLE OF DIFFERENTIATION) |
| | output: HUMAN iPS CELLS (HPS0003 STRAIN) AFTER INDUCTION OF DIFFERENTIATION |
| | EXECUTION PARAMETER VALUE: CULTURE PERIOD: 6 DAYS |
| | CONSTRAINT CONDITION: WITHIN 60 MINUTES AFTER ADJUSTMENT OF DIFFERENTIATION-INDUCING CULTURE MEDIUM B IS FINISHED |
| C10 | 2. EVALUATION PROCESS |
| | 2-1. MARKER GENE EXPRESSION EVALUATION |
| | input: HUMAN iPS CELLS (HPS0003 STRAIN) AFTER INDUCTION OF DIFFERENTIATION |
| | output: MARKER GENE EXPRESSION POSITIVE RATE (0% TO 100%) |
| | EXECUTION PARAMETER VALUE: NONE |
| | CONSTRAINT CONDITION: NONE |

FIG. 25

| | |
|---|---|
| | EXECUTION PROCEDURE 2 |
| C1 | 1. CULTURE-RELATED PROCESS |
| 26a | 1-1. OPERATION: ADJUSTMENT OF DIFFERENTIATION-INDUCING CULTURE MEDIUM A |
| 26b | input: BASAL CULTURE MEDIUM, BMP4, VEGF, GLUCOSE |
| 26c | output: DIFFERENTIATION-INDUCING CULTURE MEDIUM A |
| 26d | EXECUTION PARAMETER VALUE: BASAL CULTURE MEDIUM CONCENTRATION 10 mM |
| 26j | VARIABLE PARAMETER VALUE: BMP4 CONCENTRATION = 6 µM, VEGF CONCENTRATION = 8 µM, GLUCOSE CONCENTRATION = 6 µM |
| 26e | CONSTRAINT CONDITION: NONE |
| C2 | 1-2. OPERATION: CELL CULTURE USING DIFFERENTIATION-INDUCING CULTURE MEDIUM A (INTENDED CELL INDUCTION) |
| | input: DIFFERENTIATION-INDUCING CULTURE MEDIUM A (ADJUSTED), HUMAN iPS CELLS (HPS0003 STRAIN) |
| | output: HUMAN iPS CELLS (HPS0003 STRAIN) (BEING IN MIDDLE OF DIFFERENTIATION) |
| | EXECUTION PARAMETER VALUE: CULTURE PERIOD: 6 DAYS |
| | CONSTRAINT CONDITION: WITHIN 60 MINUTES AFTER ADJUSTMENT OF DIFFERENTIATION-INDUCING CULTURE MEDIUM A IS FINISHED |
| C3 | 1-3. OPERATION: ADJUSTMENT OF DIFFERENTIATION-INDUCING CULTURE MEDIUM B |
| | input: DIFFERENTIATION-INDUCING BASAL CULTURE MEDIUM, BMP4, VEGF, SCF |
| | output: DIFFERENTIATION-INDUCING CULTURE MEDIUM B |
| | EXECUTION PARAMETER VALUE: BASAL CULTURE MEDIUM CONCENTRATION 10 mM, BMP4 CONCENTRATION: 8 µM, VEGF CONCENTRATION: 8 µM, SCF CONCENTRATION: 12 µM |
| | CONSTRAINT CONDITION: NONE |
| C4 | 1-4. OPERATION: CELL CULTURE USING DIFFERENTIATION-INDUCING CULTURE MEDIUM B (INTENDED CELL DIFFERENTIATION) |
| | input: DIFFERENTIATION-INDUCING CULTURE MEDIUM B (ADJUSTED), HUMAN iPS CELLS (HPS0003 STRAIN) (CULTURED IN DIFFERENTIATION-INDUCING CULTURE MEDIUM A AND BEING IN MIDDLE OF DIFFERENTIATION) |
| | output: HUMAN iPS CELLS (HPS0003 STRAIN) AFTER INDUCTION OF DIFFERENTIATION |
| | EXECUTION PARAMETER VALUE: CULTURE PERIOD: 6 DAYS |
| | CONSTRAINT CONDITION: WITHIN 60 MINUTES AFTER ADJUSTMENT OF DIFFERENTIATION-INDUCING CULTURE MEDIUM B IS FINISHED |
| C5 | 2. EVALUATION PROCESS |
| | 2-1. MARKER GENE EXPRESSION EVALUATION |
| | input: HUMAN iPS CELLS (HPS0003 STRAIN) AFTER INDUCTION OF DIFFERENTIATION |
| | output: MARKER GENE EXPRESSION POSITIVE RATE (0% TO 100%) |
| | EXECUTION PARAMETER VALUE: NONE |
| | CONSTRAINT CONDITION: NONE |

FIG. 52
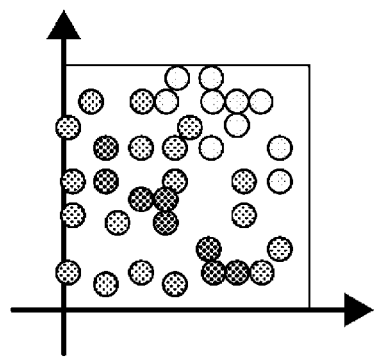
(63A)
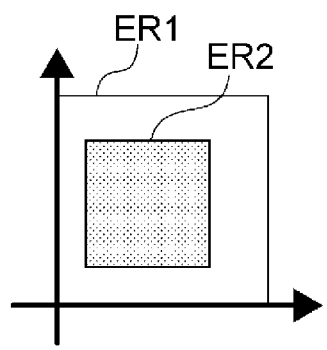
$5<x<7, 3<y<7$
(63B)
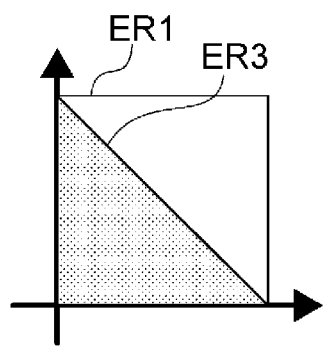
$x+y-10<0$
(63C)
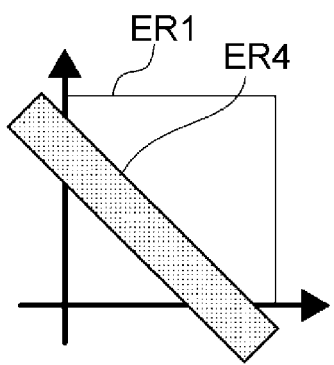
$x+y-8<0,$
$-x-y+6<0$
(63D)
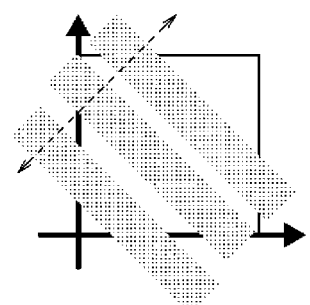
$x+y-c-2<0,$
$-x-y+c<0$
(63E)

FIG. 58

| 1. | 2. (1∧2) | 3. (1∧2∧3) | 4. (1∧2∧3∧4) |
|---|---|---|---|
| BMP4 < 3μM ∨ VEGF < 5μM ∨ 5μM ≤ SCF < 10μM ∨ [(BMP4 < 3μM) ∧ (VEGF < 5μM) ∧ (5μM ≤ SCF < 10μM)] | GLUCOSE < 5μM ∨ TREHALOSE < 5μM | SUBSTANCE K | SUBSTANCE K < 5 μM |
|  |  | 3. (1∧3) SUBSTANCE K | 4. (1∧3∧4) SUBSTANCE K < 5 μM |

CULTURE-RELATED PROCESS OPTIMIZATION METHOD AND CULTURE-RELATED PROCESS OPTIMIZATION SYSTEM

TECHNICAL FIELD

The present invention relates to a culture-related process optimization method and a culture-related process optimization system.

BACKGROUND ART

PTL 1 proposes a system that executes and manages laboratory experiments in life science.

CITATION LIST

Patent Literature

PTL 1: US2018/0196913

SUMMARY OF INVENTION

Technical Problem

Particularly, when executing cellular production in which substances (biopharmaceuticals and useful proteins) are produced by utilizing cells, and a (cell) culture-related process that utilizes cells themselves as a pharmaceutical product, such as regenerative medicine, there is a need to maximize the gain obtainable from the culture-related process; however, PTL 1 does not disclose a method of optimizing the culture-related process so as to obtain maximized gain.

Thus, the invention was made in consideration of the above-described points, and it is an object of the invention to provide a culture-related process optimization method and a culture-related process optimization system, which can optimize a culture-related process.

Solution to Problem

[1] A culture-related process optimization method according to the invention is a culture-related process optimization method for a culture-related process optimization system that optimizes a culture-related process relevant to culture of cells, the culture-related process optimization method including: an acquisition step of acquiring a starting point execution procedure, which serves as a starting point of a search and in which one or a plurality of operations performed in the culture-related process are specified and contents related to the operations are specified, by a starting point execution procedure acquisition unit; a variable parameter item identification step of identifying one or a plurality of variable parameter items for which a variable parameter value may be set in the starting point execution procedure, by a variable parameter item identification unit; an execution procedure generation step of setting the variable parameter value for the variable parameter item identified in the variable parameter item identification step on the basis of a previous execution performance result and an evaluation performance result thereof and thereby generating an execution procedure, by an execution procedure generation unit; an execution result acquisition step of acquiring an execution result obtained when an execution subject actually executes execution according to the execution procedure in an execution environment, by an execution result acquisition unit; an evaluation result acquisition step of acquiring an evaluation result with respect to the execution result, by an evaluation result acquisition unit; and a storage step of recording the execution procedure, the variable parameter value, the execution result, and the evaluation result in association with each other in a database.

[2] The culture-related process optimization method according to the above-described [1], in which the culture-related process includes at least any one of an operation related to adjustment of a culture medium and an operation related to cell culture using the culture medium, as the operation.

[3] The culture-related process optimization method according to the above-described [1], in which the culture-related process is a culture medium adjustment process of adjusting a culture medium and/or a cell culture process of culturing cells.

[4] The culture-related process optimization method according to any one of the above-described [1] to [3], in which in the variable parameter item identification step, one or a plurality of the variable parameter items for which the variable parameter value may be set in the starting point execution procedure are identified, on the basis of the execution performance result obtained when the execution subject executes execution according to a previous execution procedure that is identical or relevant to the starting point execution procedure in the execution environment.

[5] The culture-related process optimization method according to any one of the above-described [1] to [4], further including a template execution procedure generation step of generating a template execution procedure in which a search range indicating a range of the variable parameter value that may be set for the variable parameter item is set, by a template execution procedure generation unit, in which in the execution procedure generation step, the variable parameter value is selected in the search range specified by the template execution procedure, and the selected variable parameter value is set for the variable parameter item, and then the execution procedure is generated.

[6] The culture-related process optimization method according to any one of the above-described [1] to [5], in which in the execution procedure generation step, the variable parameter value is determined on the basis of the execution performance result obtained when the execution subject executes execution according to a previous execution procedure that is identical or relevant to the starting point execution procedure in the execution environment.

[7] The culture-related process optimization method according to any one of the above-described [1] to [6], in which in the execution procedure generation step, a regression model is generated on the basis of the execution performance result, and the variable parameter value to be set for the variable parameter item is determined by using the regression model.

[8] The culture-related process optimization method according to any one of the above-described [1] to [7], in which in the execution procedure generation step, the variable parameter value is set for the purpose of obtaining a desired evaluation result.

[9] The culture-related process optimization method according to any one of the above-described [1] to [8], in which the evaluation result is at least one or more kinds among cost, yield, quality, and execution time related to the execution procedure, variations in the cost, yield, quality, and execution time, and deviations from given target values of the cost, yield, quality, and execution time.

[10] The culture-related process optimization method according to any one of the above-described [1] to [9], further including an execution schedule generation step of generating an execution schedule indicating how the plurality of operations specified by the execution procedure are collaboratively executed in a time series by the respective corresponding execution subjects in the execution environment, by an execution schedule generation unit.

[11] The culture-related process optimization method according to the above-described [10], in which in the execution schedule generation step, the execution procedure is subjected to syntax analysis, a syntax tree is generated, the syntax tree being a data structure in which at least dependency between the respective operations specified by the execution procedure, processing targets of the operations, outcomes obtainable by the operations, and constraint conditions related to the operations may be analyzed, and an execution schedule is generated on the basis of the syntax tree.

[12] The culture-related process optimization method according to the above-described or [11], further including an execution environment information acquisition step of acquiring execution environment information indicating the execution subject that actually performs the operation specified by the execution procedure in the execution environment, by an execution environment information acquisition unit, in which in the execution schedule generation step, the execution schedule is generated on the basis of the execution procedure and the execution environment information.

[13] The culture-related process optimization method according to any one of the above-described to [12], in which in the execution schedule generation step, the execution schedule that takes a constraint condition set for a constraint condition item of the execution procedure into consideration, is generated.

[14] The culture-related process optimization method according to any one of the above-described [1] to [13], further including an execution instruction information generation step of generating execution instruction information that has instructed the execution subject in the execution environment to execute the operation specified by the execution procedure, by an execution instruction information generation unit.

[15] The culture-related process optimization method according to the above-described [14], in which in the execution instruction information generation step, a constraint condition set for a constraint condition item of the execution procedure is extracted to be included in the execution instruction information.

[16] The culture-related process optimization method according to any one of the above-described [1] to [15], in which in the execution procedure generation step, a constraint condition used when the execution subject performs the execution procedure in the execution environment is set for a constraint condition item of the execution procedure.

[17] The culture-related process optimization method according to the above-described [16], in which in the execution procedure generation step, a time constraint related to the operation is set for the constraint condition item, as the constraint condition.

[18] The culture-related process optimization method according to the above-described [17], in which in the execution procedure generation step, at least either of the time constraint for specifying an execution time taken for the operation by the execution subject and the time constraint for setting up a temporal constraint between the operations, is included as the time constraint.

[19] The culture-related process optimization method according to the above-described [16], in which in the execution procedure generation step, a concurrency constraint for specifying whether the plurality of operations may be performed concurrently is set for the constraint condition item, as the constraint condition.

[20] The culture-related process optimization method according to the above-described [16], in which in the execution procedure generation step, an execution condition constraint for specifying that the operation needs to be performed within a predetermined condition range is set for the constraint condition item, as the constraint condition.

[21] The culture-related process optimization method according to any one of the above-described [1] to [20], in which in the variable parameter item identification step, an item selection simulation of selecting a parameter value for item selection with respect to a candidate variable parameter item that may be the variable parameter item, which is assumed to allow a predetermined evaluation result to be obtained, and using the selected parameter value for item selection as input and the evaluation result as output, is executed by arithmetic processing, and the variable parameter item is selected on the basis of a result of the item selection simulation.

[22] The culture-related process optimization method according to any one of the above-described [1] to [20], in which in the execution procedure generation step, a variable parameter value selection simulation of selecting a candidate variable parameter value that may be the variable parameter value, which is assumed to allow a predetermined evaluation result to be obtained, and using the selected candidate variable parameter value as input and the evaluation result as output, is executed by arithmetic processing, and a range of the variable parameter value is limited on the basis of a result of the variable parameter value selection simulation.

[23] The culture-related process optimization method according to the above-described [22], in which a learned regression model that may differentiate the output with the input is generated by using the input and output of the variable parameter value selection simulation as learning data, and the range of the variable parameter value is limited on the basis of the regression model.

[24] The culture-related process optimization method according to the above-described [22], in which a learned regression model of extracting a feature amount according to a change in the candidate variable parameter value is generated by using the input and output of the variable parameter value selection simulation as learning data, and the range of the variable parameter value is limited on the basis of the regression model using the feature amount extracted from the learned regression model.

[25] The culture-related process optimization method according to the above-described [1], further including, before the execution procedure generation step: an existing condition acquisition step of acquiring an existing condition related to the culture-related process by an existing condition acquisition unit; and an optimal range search step of searching for an optimal range of the variable parameter value that may generate the execution procedure outside the range of the existing condition, the optimal range not satisfying at least one or more constituent features among a plurality of constituent features included in the existing condition within a search range of the variable parameter value specified in advance, by an optimal range search unit, in which in the execution procedure generation step, the variable parameter value is set in an optimal range of the variable parameter value searched in the optimal range search step, and then the execution procedure is generated.

[26] The culture-related process optimization method according to the above-described [25], in which the optimal range search step includes: an optimal range logic expression generation step of generating an optimal range logic expression that expresses an optimal range of the variable parameter value as a logic expression, on the basis of an existing condition logic expression expressing the existing condition as a logic expression and of a search range logic expression expressing a search range of the variable parameter value that has been set in advance as a logic expression, by an optimal range logic expression generation unit; and an analysis step of analyzing the optimal range logic expression by a logic expression analysis unit and identifying an optimal range of the variable parameter value that may generate a different execution procedure, the optimal range being outside the range of the existing condition, for each of the variable parameter items.

[27] The culture-related process optimization method according to the above-described or [26], in which in the optimal range search step, any one of a patent publication, a publication of patent application, and technical information is used as the existing condition.

[28] The culture-related process optimization method according to the above-described [27], in which when the existing condition is the patent publication or the publication of patent application, in the existing condition acquisition step, an existing claim described in the patent publication or the publication of patent application is acquired as the existing condition, and the optimal range search step includes a patent information analysis step of analyzing dependency relationships among a plurality of existing claims by a patent information analysis unit and analyzing mutual relationships among a plurality of constituent features respectively specified within the existing claims for each of the existing claims.

[29] A culture-related process optimization system for optimizing a culture-related process related to culture of cells, the culture-related process optimization system including: a starting point execution procedure acquisition unit for acquiring a starting point execution procedure, which serves as a starting point of a search and in which one or a plurality of operations performed in the culture-related process are specified and contents related to the operations are specified; a variable parameter item identification unit for identifying one or a plurality of variable parameter items for which a variable parameter value may be set in the starting point execution procedure; an execution procedure generation unit for setting the variable parameter value for the variable parameter item identified at the variable parameter item identification unit on the basis of a previous execution performance result and an evaluation performance result thereof and thereby generating an execution procedure; an execution result acquisition unit for acquiring an execution result obtained when an execution subject executes execution according to the execution procedure in an execution environment; an evaluation result acquisition unit for acquiring an evaluation result with respect to the execution result; and a database for recording the execution procedure, the variable parameter value, the execution result, and the evaluation result in association with each other.

[30] The culture-related process optimization system according to the above-described [29], further including: an existing condition acquisition unit for acquiring an existing condition related to the culture-related process; and an optimal range search unit for searching for an optimal range of the variable parameter value that may generate the execution procedure outside the range of the existing condition, the optimal range not satisfying at least one or more constituent features among a plurality of constituent features included in the existing condition within a search range of the variable parameter value specified in advance, in which in the execution procedure generation unit, the variable parameter value is set in an optimal range of the variable parameter value searched at the optimal range search unit, and then the execution procedure is generated.

Advantageous Effects of Invention

According to the invention, a culture-related process related to culture of cells can be optimized.

BRIEF DESCRIPTION OF DRAWINGS

FIG. 2 is a schematic view illustrating an example of a configuration of a starting point execution procedure.

FIG. 3 is a schematic view illustrating an example of a configuration of an execution performance result and an evaluation performance result 1 according to a previous execution procedure.

FIG. 4 is a schematic view illustrating an example of a configuration of an execution performance result and an evaluation performance result 2 according to a previous execution procedure.

FIG. 5 is a schematic view illustrating an example of a configuration of a template execution procedure.

FIG. 6 is a schematic view illustrating an example of a configuration of an execution procedure 1.

FIG. 7 is a schematic view illustrating an example of a configuration of an execution procedure 2.

FIG. 10A is a schematic view illustrating a configuration of execution environment information.

FIG. 11 is a schematic view for describing a set A' in which execution subjects are respectively allocated to operations.

FIG. 15 is a schematic view for describing a set A" in which an execution start time and an execution end hour are allocated to each element of the set A'.

FIG. 16 is a schematic view for describing a set A''' of combinations satisfying a constraint condition.

FIG. 19 is a schematic view illustrating an example of a configuration of another starting point execution procedure.

FIG. 20 is a schematic view illustrating an example of a configuration of a previous relevant execution procedure A.

FIG. 21 is a schematic view illustrating an example of a configuration of a previous relevant execution procedure B.

FIG. 22 is a schematic view illustrating an example of an evaluation performance result of a previous relevant execution procedure.

FIG. 23 is a schematic view illustrating an example of a configuration of another template execution procedure.

FIG. 24 is a schematic view illustrating an example of a configuration of another execution procedure 1.

FIG. 25 is a schematic view illustrating an example of a configuration of another execution procedure 2.

FIG. 52 is a schematic view for describing an occasion of limiting the range of the variable parameter value in the second embodiment.

FIG. 58 is a schematic view illustrating a logic expression that correlates the dependency relationships of existing condition logic expressions of the existing claims 1 to 4.

DESCRIPTION OF EMBODIMENTS

Figure 1:
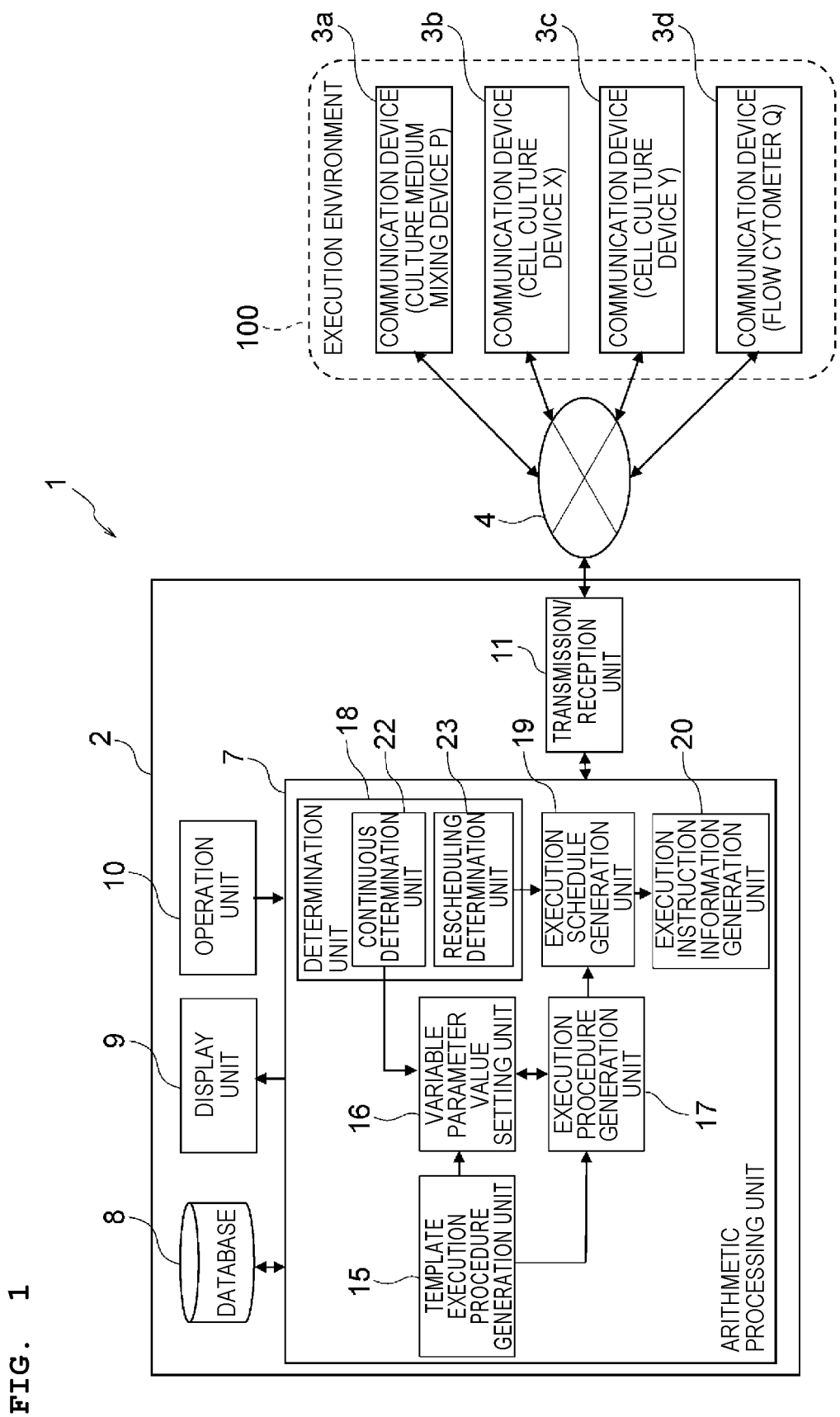
FIG. 1 is a block diagram illustrating an overall configuration of a culture-related process optimization system according to the present embodiment.

Hereinafter, an embodiment of the invention will be described in detail with reference to the drawings. In the following description, the same reference numerals will be assigned to the same constituent elements, and redundant descriptions will not be repeated herein.

(1) Culture-Related Process Optimization Method According to First Embodiment (1-1) Outline of Culture-Related Process Optimization Method According to First Embodiment First, an outline of a culture-related process optimization method according to the present embodiment will be described. The culture-related process as used herein is a variety of processes related to culture of cells, in which one or a plurality of operations required in the course of culturing various cells are executed. In the following embodiment, a series of processes including from a process of adjusting the culture medium used for culturing cells (hereinafter, also referred to as culture medium adjustment process) to a process of culturing cells using the culture medium (hereinafter, also referred to as cell culture process) may be applied as the culture-related process, and only the culture medium adjustment process may be applied as a culture-related process, or only the cell culture process may be applied as a culture-related process. The culture-related process includes at least some of operations such as selection of a basal culture medium, adjustment of a culture medium, selection of components used for the adjustment of a culture medium, culturing of cells using the culture medium after adjustment and culture conditions thereof, selection of an execution subject such as a device executing these operations, and determination of a processing procedure of the execution subject.

FIG. 1 is a block diagram illustrating the overall configuration of a culture-related process optimization system 1 that executes a culture-related process optimization method. As shown in FIG. 1, the culture-related process optimization system 1 has a configuration in which a culture-related process optimization device 2 and a plurality of communication devices 3a, 3b, 3c, and 3d are connected to a network 4 such as the Internet.

In the culture-related process optimization system 1, for example, in various culture-related processes such as a culture-related process related to regenerative medicine of culturing human iPS cells to induce differentiation into specific cells, a culture-related process of culturing CHO cells to produce biopharmaceuticals (antibody production), and a culture-related process related to the production of useful proteins, by which compounds are produced by culturing *Escherichia coli* X to induce expression of an enzyme R, an execution procedure for obtaining an optimal evaluation result with a gain as large as possible is sought through trial and error.

Here, regarding the optimal evaluation result, at least one or more kinds among cost, yield, quality, and execution time related to the execution procedure of the culture-related process, variations in the cost, yield, quality, and execution time, and deviations from given target values of the cost, yield, quality, and execution time, can be applied. For example, in an example of an evaluation result of a culture-related process of culturing cells in a plurality of types of culture media P and Q to induce differentiation from human iPS cells and the like into specific cells, examples of the optimal evaluation result include cost involved in producing cells, yield of the cells, quality of the cells, execution time taken to produce the cells, variations in the cost, yield, quality and execution time, and deviations from given target values of the cost, yield, quality and execution time.

Here, the execution procedure is data in which a series of operations (for example, adjustment of the culture medium, culturing, and evaluation of the expression of a marker gene) carried out in culture-related processes and evaluation processes, a processing target (for example, human iPS cells) to be respectively processed by each operation, an outcome (for example, cells induced to differentiate from human iPS cells) obtainable after processing the processing target by each operation, various execution parameter values (for example, basal culture medium concentration, BMP4 concentration, VEGF concentration, glucose concentration, and culture period) set when processing the processing target by the operations, and constraint conditions (for example, "after a lapse of 5 minutes or longer after the device starts up") related to the operations are described.

For example, an experimental procedure showing a series of operations employed when life science experiments are performed in a laboratory by a plurality of experimenters or the like, and culture medium adjustment and culture procedure showing a series of operations including from adjustment of a culture medium to culture of cells in the culture medium by using a plurality of devices, correspond to the execution procedure.

Here, the production conditions in the execution procedure of the culture-related process (for example, combinations of various execution parameter values such as the basal culture medium concentration and the glucose concentration), in which a gain obtained from a certain culture-related process is maximized, are not obvious, and in a naïve method, it is necessary to repeatedly execute a large number of experiments and perform trial and error. As the product becomes more complicated, the culture-related process also becomes more complicated and massive, and it is more difficult to seek an optimal production condition by searching for various production conditions. In addition, even in a culture-related process of various product types in large quantities and a culture-related process of utilizing a living organism in the production of a pharmaceutical product or the like, automation has been attempted by utilizing robots and the like; however, it is necessary to seek an optimal production condition each time in each case due to the difference in the varieties of the object of production, the difference in the individuals of the biological organism, and the like, and consequently, the total cost needed for searching for the production conditions is increased.

Generally, when searching for the production conditions, in a case where the type and number of an execution subject performing each operation in the culture-related process, such as a mechanical device, a robot, or a man (operator), are increased, execution instruction information appropriate for each execution subject is generated sequentially for each search condition of the production conditions, and therefore, enormous efforts are required.

In the culture-related process optimization system 1 according to the present embodiment, when the execution subject actually executes the culture-related process in an execution environment 100 according to the execution procedure in consideration of the above-described points and searches for an optimal production condition in which a gain as large as possible is obtained, it can be such that an optimal production condition with a large gain is sought by experiments at a number of times as minimal as possible, and reduction of the total cost and efforts required for searching for the production conditions is promoted, while at the same time, an optimal culture-related process with a large gain is sought.

Here, as an example of the culture-related process to be optimized by the culture-related process optimization system 1 according to the present embodiment, an outline of the culture-related process optimization system 1 according to the present embodiment will be described below by mentioning a culture-related process that induces human iPS cells by using a differentiation of differentiation-inducing culture medium A (hereinafter, also simply referred to as "culture medium A") and a differentiation-inducing culture medium B of a type different from the type of the culture medium A (hereinafter, also simply referred to as "culture medium B") and produces specific cells. In addition, as an example of an evaluation process for evaluating cells induced to differentiate from human iPS cells, which have been obtained by the culture-related process, a case of performing an evaluation of the expression positive rate of a marker gene will be described.

As shown in FIG. 1, a culture-related process optimization device 2 included in the culture-related process optimization system 1 has an arithmetic processing unit 7, a database 8, a display unit 9, an operation unit 10, and a transmission/reception unit 11. The transmission/reception unit 11 functions as an execution result acquisition unit and an evaluation result acquisition unit.

The arithmetic processing unit 7 has a microcomputer configuration consisting of a CPU (Central Processing unit), a RAM (Random Access Memory), a ROM (Read Only Memory), and the like, which are not shown in the figure, and the database 8, the display unit 9, the operation unit 10, and the transmission/reception unit 11 are connected to the arithmetic processing unit 7.

When various operation commands are given from a manager (also referred to as user) of the culture-related process optimization device 2 through the operation unit 10, the arithmetic processing unit 7 reads out a culture-related process optimization program, a template execution procedure generation processing program, a variable parameter value setting processing program, an execution schedule generation processing program, an execution instruction information generation processing program, and the like, which are stored in advance in the ROM, as appropriate on the basis of the operation commands and deploys the programs in the RAM, and thereby the arithmetic processing unit 7 controls each circuit unit according to the culture-related process optimization program and the like.

The arithmetic processing unit 7 generates a template execution procedure, an execution schedule, execution instruction information, and the like by executing, for example, culture-related process optimization processing and stores these arithmetic processing results in the database 8.

The database 8 stores the arithmetic processing result of the arithmetic processing unit 7 and also stores execution environment information (will be described below) received from the outside by the transmission/reception unit 11, and the like. In addition, in the database 8, various data such as an execution result obtained when an execution result executed an execution procedure of the culture-related process in the previous in the execution environment 100 (hereinafter, a previous execution result will be also referred to as an execution performance result), and a previous evaluation result obtained by evaluating the execution performance result (hereinafter, an evaluation result for a previous execution result is also referred to as an evaluation performance result), are stored.

The display unit 9 may display the arithmetic processing results of the template execution procedure generated by the arithmetic processing unit 7, an execution procedure, and the like, and allow a manager or the like who manages the culture-related process optimization device 2, to grasp the arithmetic processing result.

The culture-related process optimization device 2 according to the present embodiment generates execution procedures of the culture-related process of inducing human iPS cells to differentiate by using culture media A and B to produce specific cells and the evaluation process, an execution schedule, which is data indicating at what timing each of the execution subjects should collaboratively perform each operation in the execution procedure, and execution instruction information, which is data instructing the execution subjects of the execution environment 100 to execute corresponding operations, respectively, in accordance with the execution schedule, by the culture-related process optimization processing.

The culture-related process optimization device 2 transmits the execution schedule and the execution instruction information to the communication devices 3a, 3b, 3c, and 3d of the corresponding execution subjects in the execution environment 100 through the network 4.

Here, the execution environment 100 shown in FIG. 1 represents an environment in which the execution procedures of the culture-related process and the evaluation process are actually executed, and examples include a plant and a laboratory. An execution subject in the execution environment 100 executes each operation specified in the execution procedures of the culture-related process and the evaluation process. The execution subject varies in accordance with the types of the culture-related process and the evaluation process, and for example, a mechanical device, a robot arm, a man, an incubator, a measuring instrument of a camera or the like, an experimental automation device, and a calculator correspond to the execution subject.

In the present embodiment, a culture-related process of inducing differentiation of human iPS cells (hereinafter, also simply referred to as "cells") by using culture media A and B and producing specific cells, and an evaluation process of performing a marker gene expression evaluation of the cells produced by executing the execution procedure of the culture-related process will be described as an example, and in this case, a culture medium mixing device P for adjusting and mixing the culture media A and B, cell culture devices X and Y for culturing cells, and a flow cytometer Q for performing the marker gene expression evaluation may be execution subjects.

In the culture-related process optimization system 1 according to the present embodiment, the execution schedule and execution instruction information generated by the culture-related process optimization device 2 are transmitted to the communication devices 3a, 3b, 3c, and 3d of the execution subjects through the network 4, in order to present the execution schedule and the execution instruction information to the culture medium mixing device P, cell culture devices X and Y, and the flow cytometer Q, which are the execution subjects.

For example, the communication device 3a is connected to or mounted on the culture medium mixing device P, and may present setting information included in the execution instruction information generated for the culture medium mixing device P to the culture medium mixing device P and automatically operate the culture medium mixing device P according to the execution schedule on the basis of the setting information.

The communication device 3a may also be, for example, an electronic instrument such as a personal computer or a smartphone possessed by an operator performing an operation for adjusting each of the culture media A and B and mixing of the culture media A and B as necessary. In this case, the communication device 3a presents the execution schedule received from the culture-related process optimization device 2 and the execution instruction information generated for the culture medium mixing device P to the operator operating the culture medium mixing device P, and allows the operator to perform an adjustment operation or the like by using the culture medium mixing device P.

The communication device 3b is connected to or mounted on the cell culture device X, and may present setting information included in the execution instruction information generated for the cell culture device X to the cell culture device X and automatically operate the cell culture device X according to the execution schedule on the basis of the setting information. In addition, the communication device 3c is also connected to or mounted on the cell culture device Y, and may present setting information included in the execution instruction information generated for the cell culture device Y to the cell culture device Y and automatically operate the cell culture device Y according to the execution schedule on the basis of the setting information.

Each of the communication devices 3b and 3c may be, for example, an electronic instrument such as a personal computer or a smartphone possessed by each operator performing a culturing operation with the culture medium A or the culture medium B. In this case, the communication devices 3b and 3c present an execution schedule received from the culture-related process optimization device 2 and the execution instruction information generated for the cell culture devices X and Y to each of the operators operating the cell culture devices X and Y, and allow each of the operators to perform a culturing operation by using the cell culture device X or Y.

The flow cytometer Q is, for example, a cell analysis device capable of performing a marker gene expression evaluation of cells cultured by using the culture media A and B. The communication device 3d is connected to or mounted on the flow cytometer Q, and may present setting information included the in execution instruction information generated for the flow cytometer Q to the flow cytometer Q and automatically operate the flow cytometer Q according to the execution schedule on the basis of the setting information. In addition, the communication device 3d may be, for example, an electronic instrument such as a personal computer or a smartphone possessed by an operator performing a marker gene expression evaluation operation. In this case, the communication device 3d presents an execution schedule received from the culture-related process optimization device 2 and the execution instruction information generated for the flow cytometer Q to the operator operating the flow cytometer Q, and allows each of the operators to perform a marker gene expression evaluation operation or the like by using the flow cytometer Q.

Furthermore, these communication devices 3a, 3b, 3c, and 3d transmit the execution results obtained when the corresponding execution subjects execute the execution according to the execution schedule or the execution instruction information, or the evaluation results as appropriate to the culture-related process optimization device 2 through the network 4.

Next, the arithmetic processing unit 7 of the culture-related process optimization device 2 will be described. The arithmetic processing unit 7 includes a template execution procedure generation unit 15, a variable parameter value setting unit 16, an execution procedure generation unit 17, a determination unit 18, an execution schedule generation unit 19, and an execution instruction information generation unit 20, and a template execution procedure, an execution procedure, an execution schedule, and execution instruction information, which will be described below, are generated in the arithmetic processing unit 7.

Here, the template execution procedure is created in the form of rewriting an execution procedure that serves as a starting point of a certain search (hereinafter, referred to as starting point execution procedure). FIG. 2 is a schematic view illustrating an example of the configuration of the starting point execution procedures related to the culture-related process related to cells to be cultured using the culture media A and B and the evaluation process.

In the template execution procedure generation unit 15, when the culture-related processes (for example, adjustment of culture media A and B, cell culture using the culture medium A, and culture of cells that have been cultured using the culture medium A and are in the middle of differentiation, using the culture medium B) and the evaluation process (marker gene expression evaluation), which are desired to be optimized by the manager, are selected or inputted through the operation unit 10, the execution procedures corresponding to these culture-related processes and evaluation process among a plurality of execution procedures stored in the database 8 are selected as the starting point execution procedures.

In this case, in the template execution procedure generation unit 15, as shown in FIG. 2, an execution procedure in which four operations of the adjustment of the culture medium A, cell culture using the culture medium A (having been adjusted), the adjustment of the culture medium B, and culture of cells that have been cultured using the culture medium A and are in the middle of differentiation, using the culture medium B (having been adjusted), are specified as operations of the culture-related process, and one operation of marker gene expression evaluation is specified as an operation of the evaluation process, is selected as the starting point execution procedure.

In the starting point execution procedure, contents related to the operations performed in the culture-related process and the evaluation process are specified for operation outline fields C1, C2, C3, and C4 for each operation. The operation outline fields C1, C2, C3, and C4 of the starting point execution procedure according to the present embodiment include, for example, an operation item 26a that specifies the content of an operation, an input item 26b that specifies the processing target of the operation, an output item 26c that specifies an outcome obtained by the operation, an execution parameter item 26d that specifies a numerical value related to the operation, and a constraint condition item 26e that specifies a constraint condition related to the operation.

For example, in the operation outline field C1, the "adjustment of differentiation-inducing culture medium A" is specified for the operation item 26a; the "Basal culture medium, BMP4, and VEGF", which are processing targets, are specified for the input item 26b; the "differentiation-inducing culture medium A", which is an outcome, is specified for the output item 26c; the "Basal culture medium concentration", the "BMP4 concentration", "VEGF concentration", and "Glucose concentration" are specified for the execution parameter item 26d, and "None" is specified for the constraint condition item 26e.

In addition, in the "Basal culture medium concentration" specified for the execution parameter item 26d, "10 mM" is specified as a parameter value indicating the concentration of the basal culture medium; in the "BMP4 concentration", "2 µM" is specified as a parameter value indicating the concentration of BMP4 (Bone Morphogenetic Protein 4: bone morphogenetic factor 4); in the "VEGF concentration", "5 µM" is specified as a parameter value indicating the concentration of VEGF (Vascular Endothelial Growth Factor); and in the "glucose concentration", "4 UM" is specified as a parameter value indicating the concentration of glucose.

The term "None" as specified for the constraint condition item 26e implies that a constraint condition related to an operation called "Adjustment of differentiation-inducing culture medium A" is not specified.

A constraint condition specifies a condition for constraining an operation, examples thereof include a time constraint, a concurrency constraint, and an execution condition constraint, and it is specified that an operation is constrained by time, environment, temperature, humidity, degree of cleanliness, and the like.

Examples of the time constraint include a time constraint for specifying the execution time taken for an operation of the execution procedure by an execution subject, and a time constraint for providing a temporal constraint between operations of the execution procedure. The execution condition constraint includes an execution condition constraint for specifying that an operation of the execution procedure must be performed within a predetermined range of condition, and for example, a constraint condition such as "Within 60 minutes after adjustment of differentiation-inducing culture medium B is finished" as shown in the constraint condition item 26*e* of the operation outline field C4 corresponds to the execution condition constraint.

In the starting point execution procedure of the culture-related process and the evaluation process according to the present embodiment, in addition to the operation outline field C1 related to "Adjustment of differentiation-inducing culture medium A", an operation outline field C2 related to "Cell culture using differentiation-inducing culture medium A (target cell induction)", an operation outline field C3 related to "Adjustment of differentiation-inducing culture medium B", an operation outline field C4 related to "Cell culture using differentiation-inducing culture medium B (target cell differentiation)", and an operation outline field C5 related to "Marker gene expression evaluation" are specified. In the "SCF concentration" specified for the execution parameter item 26*d* of the operation outline field C3, a parameter value indicating the concentration of SCF (Stem Cell Factor) is specified. Furthermore, in the operation outline field C5 related to the "Marker gene expression evaluation", an index of 0% to 100% indicating the probability as an expression positive rate of the marker gene is set for the output item 26*c*.

In the operation outline field C2 related to the "Cell culture using differentiation-inducing culture medium A (target cell induction)", "Differentiation-inducing culture medium A (adjusted), human iPS cells (HPS0003 strain)" is specified for the input item 26*b*, and from the specification "Differentiation-inducing culture medium A (adjusted)", it is specified that the operation is an operation performed after the operation specified in the operation outline field C1 is ended. In addition, in the operation outline field C4 related to the "Cell culture using differentiation-inducing culture medium B (target cell differentiation)", "Differentiation-inducing culture medium B (adjusted), human iPS cells (HPS0003 strain) (cultured in differentiation-inducing culture medium A and being in middle of differentiation)" is specified for the input item 26*b*; from the specification "Differentiation-inducing culture medium B (adjusted)", it is specified that the operation is an operation performed after the operation specified in the operation outline field C3 is ended; and from the specification "human iPS cells (HPS0003 strain) (cultured in differentiation-inducing culture medium A and being in middle of differentiation), it is specified that the operation is an operation performed after the operation specified for the operation outline field C2 is ended.

The template execution procedure generation unit 15 selects the execution parameter item 26*d* in which the execution parameter value can be changed during the starting point execution procedure, as a variable parameter item on the basis of the execution performance result of the previous execution procedure and the evaluation performance result thereof stored in the database 8, and generates a template execution procedure for determining which execution procedure of the execution parameter value should be used subsequently to execute the culture-related process and the evaluation process in the execution environment 100 and to evaluate the execution result.

FIG. 3 and FIG. 4 illustrate examples of the configuration of the execution performance result and the evaluation performance result obtained by the previous execution procedure, which are searched from the database 8 on the basis of the contents of the operation outline fields C1, C2, C3, and C4 of the starting point execution procedure shown in FIG. 2. The template execution procedure generation unit 15 makes, for example, a comparison of a plurality of execution performance results and evaluation performance results searched from the database 8 and identifies an execution parameter item 26*d* that can serve as a variable parameter item for which the execution parameter value can be changed, among the execution parameter items 26*d* of the operation outline fields C1, C2, C3, and C4. On the occasion of identifying the execution parameter item 26*d* that can serve as a variable parameter item, for example, the tendency of change in the numerical value of the execution parameter value and the like in the execution performance result and the evaluation performance result can be adopted as a guide.

The template execution procedure generation unit 15 compares, for example, the execution performance result and evaluation performance result 1 shown in FIG. 3 with the execution performance result and evaluation performance result 2 shown in FIG. 4, and with regard to the "BMP4 concentration", "VEGF concentration", and "Glucose concentration" of the execution parameter item 26*d* in the operation outline field C1 of the "Adjustment of differentiation-inducing culture medium A", the template execution procedure generation unit 15 may assume an item for which these execution parameter values may be variable parameter values (variable parameter item), on the basis of the fact that each of the execution parameter values is different, and due to the differences of these, the evaluation performance results indicated for the output item 26*c* of the operation outline field C5 in FIG. 3 and FIG. 4 are different.

Among the execution parameter values of the starting point execution procedure, a search range set for the previous execution procedure in which the execution performance result has been obtained may be identified, and an intersection with a sum set of this previous search range may be set as a new search range. In addition, with regard to a plurality of execution performance results, in a case where even though the same execution parameter item is changed, the fluctuation range of each of the evaluation performance results is equal to or less than a predetermined value, a rule may be set in which the execution parameter item has less influence on the evaluation performance result and is not adopted as the variable parameter item.

In the present embodiment, in order to simplify the description, a case in which the variable parameter item is determined from among the execution parameter items for which numerical values are set, as the variable parameter item will be described; however, the operation item 26*a* and the like which specify operations other than numerical values, such as adjustment of the culture medium and culturing of cells, may be selected as the variable parameter items. That is, in the starting point execution procedure, all the operations that can be changed in the execution environment 100 and the conditions related to the operations may be variable parameter items. An example in which the operation item 26*a* and the like that specify operations other than numerical values are selected as the variable parameter items, will be described in detail in another embodiment that will be described below.

The template execution procedure generation unit 15 compares the execution performance result and the evaluation performance result 1 shown in FIG. 3 with the execution performance result and the evaluation performance result 2 shown in FIG. 4, and sets a search range that is a numerical value range of a variable parameter value for the variable parameter item. In this case, with regard to these execution performance results and evaluation performance results, the template execution procedure generation unit 15 may estimate the range (search range) of a variable parameter value in which a desired marker gene expression positive rate is obtained, on the basis of the fact that the "Marker gene expression positive rate" of the output item 26c in the operation outline field C5 of the "Marker gene expression evaluation" of the evaluation process is different, and of the execution parameter value of the execution parameter item 26d that is a variable parameter item, and may generate a template execution procedure in which the variable parameter item 26g and a search range thereof are set, as shown in FIG. 5.

For example, in the execution performance result and the evaluation performance result 1 shown in FIG. 3 as an example, the "BMP4 concentration" of the execution parameter item 26d in the operation outline field C1 of the "Adjustment of differentiation-inducing culture medium A" is 8 UM, which is higher than the "BMP4 concentration" of FIG. 4; the "VEGF concentration" is also 12 μM, which is higher than the "VEGF concentration" of FIG. 4; and the "Glucose concentration" is 4 μM, which is lower than the "Glucose concentration" of FIG. 4. This is assumed to be a factor for obtaining a result that the marker gene expression positive rate shown in FIG. 3 is "75%", which is higher than the marker gene expression positive rate shown in FIG. 4. Then, it is assumed that the execution parameter item 26d in the operation outline field C1 of the "Adjustment of differentiation-inducing culture medium A" affects the marker gene expression positive rate, and these are set as the search range of the variable parameter value. According to such a feature extraction rule, the search range of the variable parameter value is estimated.

In this way, the template execution procedure generation unit 15 estimates one or more types of execution parameter items that may affect the evaluation performance result and search ranges thereof from one or more types of previous execution performance results and evaluation performance results on the basis of a given feature extraction rule.

Here, a case has been described in which there is a previous execution procedure configured to include the same operations as those of the starting point execution procedure, and the variable parameter item 26g and a search range thereof in the starting point execution procedure are set on the basis of the execution performance result and the evaluation performance result of this previous execution procedure. The template execution procedure generation unit 15 also has a function of, even in a case where the starting point execution procedure is configured to include operations different from those of previous execution procedures, selecting a previous execution procedure related to the starting point execution procedure (hereinafter, referred to as related execution procedure) and setting the variable parameter item 26g and a search range thereof in the starting point execution procedure on the basis of the execution performance result and the evaluation performance result of the related execution procedure.

For example, in a case where the operations of the starting point execution procedure include an unknown operation that is not included in the previous execution procedure, the types and the numerical values of the execution parameter values of the two procedures are generally different. However, the template execution procedure generation unit 15 estimates, for example, the execution parameter item that will affect the evaluation result by the operations of the evaluation process in the starting point execution procedure, and a search range thereof, by performing contrast analysis with respect to the execution performance results and the evaluation performance results of a plurality of relevant execution procedures.

In the template execution procedure generation unit 15, by designing a feature amount transformation function in the form of combining at least one matrix operation and at least one linear or nonlinear transformation between the execution parameter values of the starting execution procedure and the execution parameter values of the execution performance results and the evaluation performance results of a plurality of relevant execution procedures, a correspondence between the two can be obtained. In addition, the feature amount transformation function itself may be made changeable by sequential optimization.

Here, the feature amount transformation function refers to a function such that even though a search space used for estimating the search range is high-dimensional, when the dimension that actually contributes to an objective variable is low-dimensional, the function is intended to extract a low-dimensional space effective for the objective variable on the basis of previous execution performance results and evaluation performance results. By performing a search for the variable parameter value on a low-dimensional search space generated by such a feature amount transformation function, the search can be performed more efficiently.

Here, for example, a machine learning model according to a neural network or the like, which is a kind of regression model, can be defined as a type of combining at least one matrix operation and at least one linear or nonlinear transformation.

As an example of designing a feature amount transformation function in the form of combining at least one matrix operation and at least one linear or nonlinear transformation, the following example may be mentioned. For example, a case is assumed in which there is a constant relationship between the culture temperature and the culture time of cells, and the conditions (culture temperature and culture time) are changed while the relationship is satisfied, the evaluation value is a little high (a case in which a desired evaluation result is obtained). In such a case, an efficient search can be carried out by learning the relationship between the culture time and culture temperature at which the evaluation value is a little higher through the feature amount transformation function, and then performing sequential optimization on a space designated by the feature amount transformation function.

Furthermore, with regard to the execution performance result and evaluation performance result of the relevant execution procedure, the template execution procedure generation unit 15 sets previous knowledge in which a manager and the like have analyzed in advance which factor contributes most to the improvement of the evaluation result, as a rule, and therefore, setting of the variable parameter item and the search range thereof in the starting point execution procedure can be effectively performed from the execution performance result and the evaluation performance result of the relevant execution procedure. A detailed description on the occasion of setting the variable parameter item and the search range thereof on the basis of the execution performance result and the evaluation performance result of the relevant execution procedure will be described below.

FIG. 5 illustrates an example of the configuration of a template execution procedure in which the variable parameter items 26g are set in the starting point execution procedure with reference to the execution performance result and the evaluation performance result, and setting a search range for each of the variable parameter items 26g.

In this example, the "BMP4 concentration", "VEGF concentration", and "Glucose concentration" in the operation outline field C1 of the "Adjustment of differentiation-inducing culture medium A" are set as the variable parameter item 26g, with reference to the execution performance result and the evaluation performance result.

The template execution procedure generation unit 15 transmits the generated template execution procedure to the variable parameter value setting unit 16 and the execution procedure generation unit 17. The variable parameter value setting unit 16 determines by which variable parameter value in the search range the execution procedure will be executed in the execution environment 100, on the basis of previous execution performance results and evaluation performance results, and transmits a plurality of variable parameter values selected from the search range to the execution procedure generation unit 17.

Here, the variable parameter value setting unit 16 generates a plurality of variable parameter values included in the search range for the template execution procedure according to a given procedure (for example, Bayesian optimization, an orthogonal table, or a Latin hypercube method), on the basis of one or more types of previous execution performance results and evaluation performance results. In addition, the variable parameter values may be set by projecting the execution performance result onto a search space representing the search range of the variable parameter item 26g.

In the present embodiment, even in a case where previous execution performance results and evaluation performance results are not present in the database 8, for example, the variable parameter values can be set in the search range according to the rule set by the manager, such as an orthogonal method.

In the variable parameter value setting unit 16 according to the present embodiment, for example, a regression model (response surface) is generated from one or more types of previous execution performance results and evaluation performance results, and by using this regression model, a plurality of variable parameter values are selected from within the search range by, for example, Bayesian optimization or multitask Bayesian optimization.

The execution procedure generation unit 17 writes each of the variable parameter values selected by the variable parameter value setting unit 16 into the variable parameter item 26g of the template execution procedure, and generates a plurality of execution procedures with different variable parameter values. In this way, the execution procedure generation unit 17 generates a list of a plurality of execution procedures with different variable parameter values.

FIG. 6 and FIG. 7 illustrate examples of two execution procedures with different variable parameter values, which are set for the variable parameter item 26g. FIG. 6 shows, as an example of the execution procedure, an execution procedure in which for the variable parameter item 26g in the operation outline field C1 of the "Adjustment of differentiation-inducing culture medium A", "5 μM" is set as the variable parameter value of the "BMP4 concentration", "10 μM" is set as the variable parameter value of the "VEGF concentration", and "11 μM" is set as the variable parameter value of the "Glucose concentration".

Furthermore, FIG. 7 shows, as an example of another execution procedure, an execution procedure in which for the variable parameter item 26g in the operation outline field C1 of the "Adjustment of differentiation-inducing culture medium A", "6 μM" is set as the variable parameter value of the "BMP4 concentration", "8 μM" is set as the variable parameter value of the "VEGF concentration", and "6 μM" is set as the variable parameter value of the "Glucose concentration".

The execution procedure generation unit 17 generates a list including such a plurality of execution procedures and transmits the list of these execution procedures to the execution schedule generation unit 19.

The execution schedule generation unit 19 sequentially selects the execution procedures from the list of execution procedures and generates an execution schedule for each execution procedure. Here, as an example, an outline of generating an execution schedule from the execution procedure shown in FIG. 6 is described.

Here, in order to simplify the description, a case is described in which the execution procedures are sequentially selected from the list of execution procedures, and execution schedules of the execution procedures are generated; however, each execution schedule may be generated at one time for a plurality of execution procedures in the list, or one execution schedule indicating the relationship in the progress circumstances of a plurality of execution procedures may be generated.

The execution subject to which a plurality of execution schedules are presented at one time may execute, for example, execution procedures according to a plurality of execution schedules simultaneously at one time in accordance with the contents of the execution schedules, or the execution subject may sequentially select any execution schedules from among a plurality of execution schedules and execute the execution procedures according to each execution schedule. It is desirable that every time when an execution result or an evaluation result of executing these execution procedures is obtained, the execution subject transmits these results to the culture-related process optimization device 2 each and every time.

The culture-related process optimization device 2 presents the execution schedules to the execution subject in the execution environment 100 and allows the execution subject to execute the execution procedures according to the execution schedules; however, for example, when execution results and evaluation results are received from the execution subject, it is desirable that execution procedures reflecting the contents of these execution results and evaluation results are regenerated, and an execution schedule of the regenerated execution procedures is generated at each and every time. As a result, an optimal execution procedure reflecting the actual execution results and evaluation results obtained by the execution subject in the execution environment 100 each and every time can be generated, and optimization of the culture-related process can be promoted.

As described above, the processing of the culture-related process optimization device 2 when a plurality of execution schedules are presented to the execution subjects, and the culture-related process optimization device 2 receives each of the execution results, evaluation results, and the like of the plurality of execution procedures from each execution subject, will be described below by using FIG. 17B.

Figure 8:
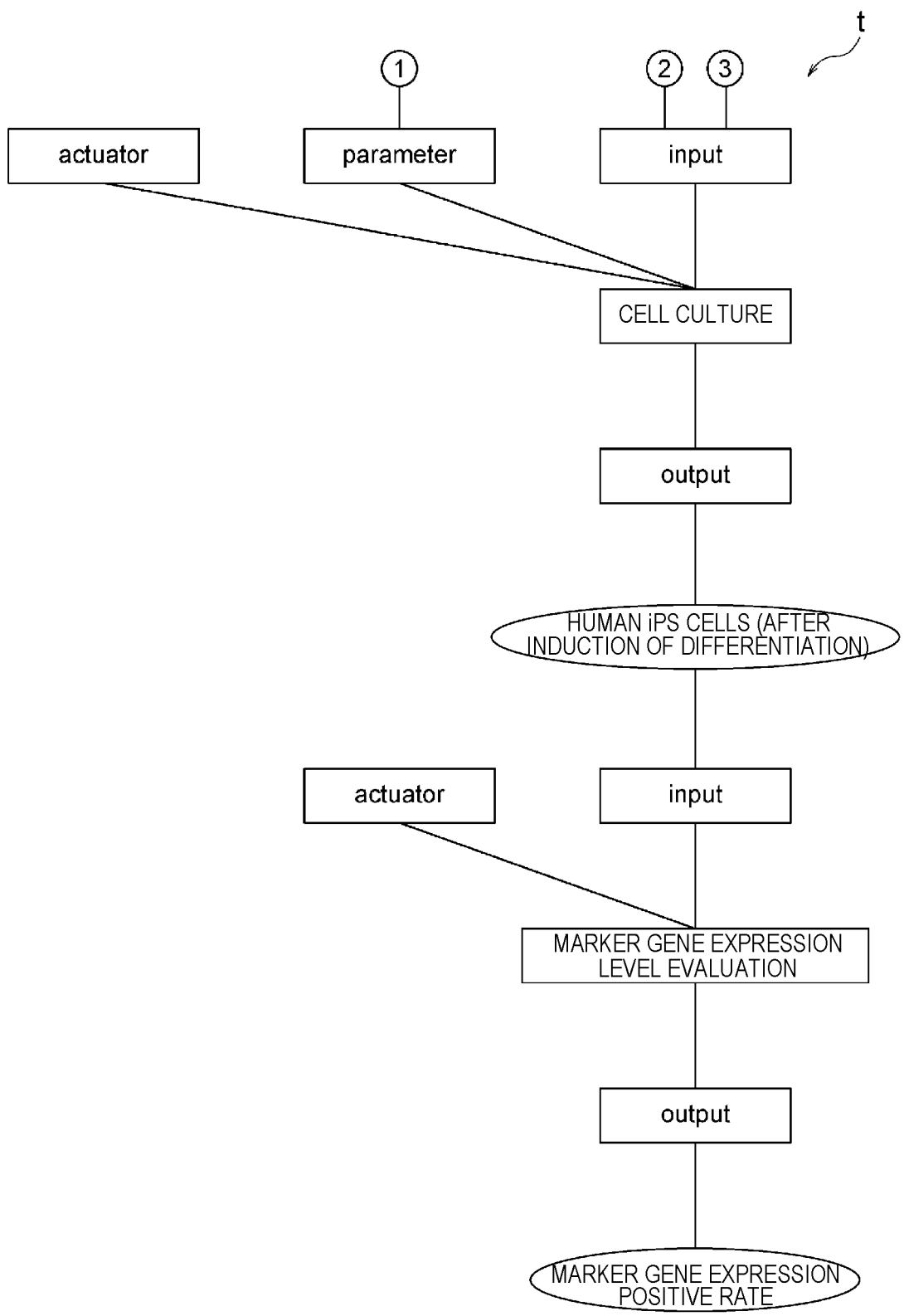
FIG. 8 is a schematic view illustrating an example of a configuration of f an execution procedure abstract syntax tree.
Figure 9A:
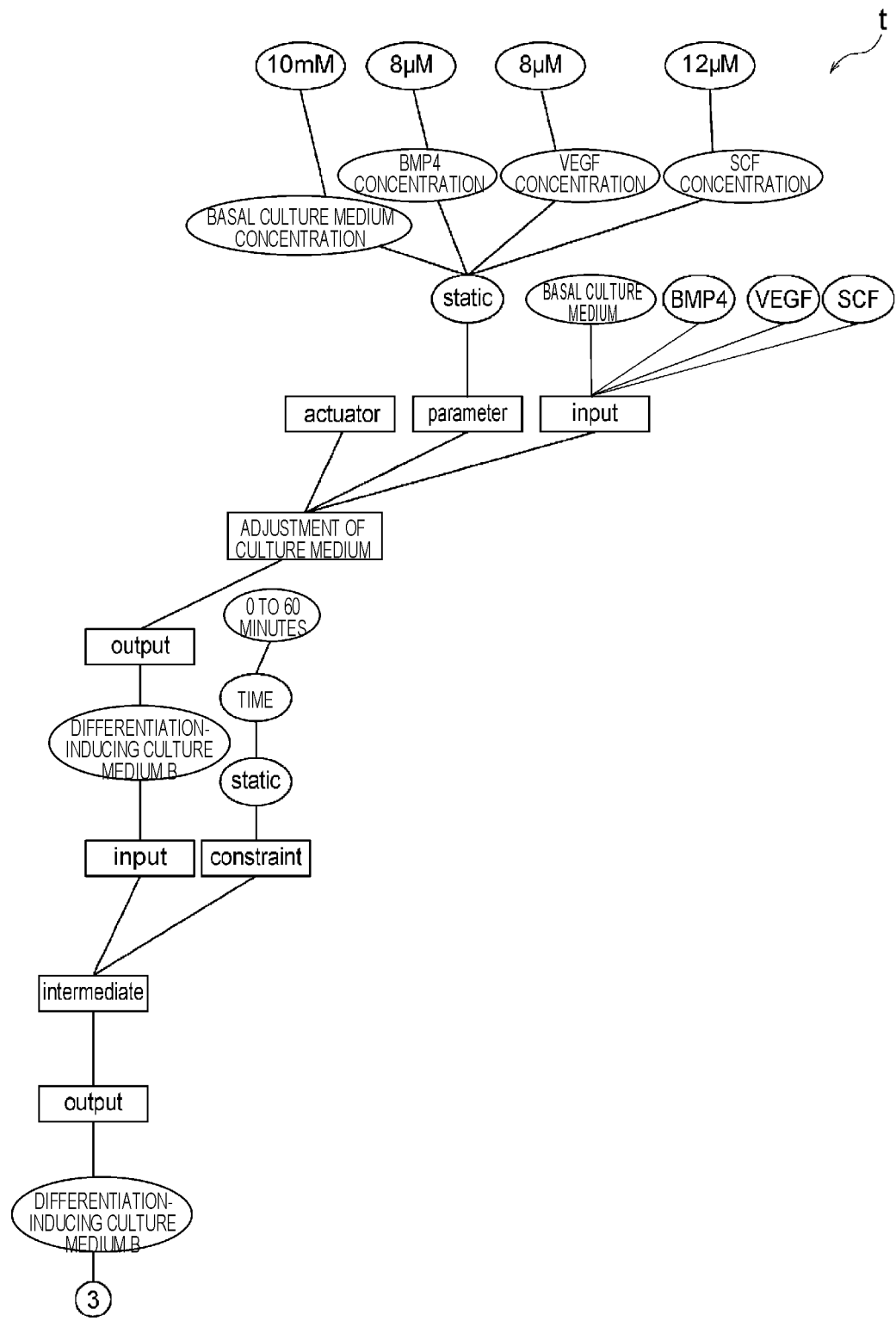
FIG. 9A is a schematic view illustrating a configuration of a continuation of the execution procedure abstract syntax tree shown in FIG. 8.
Figure 9B:
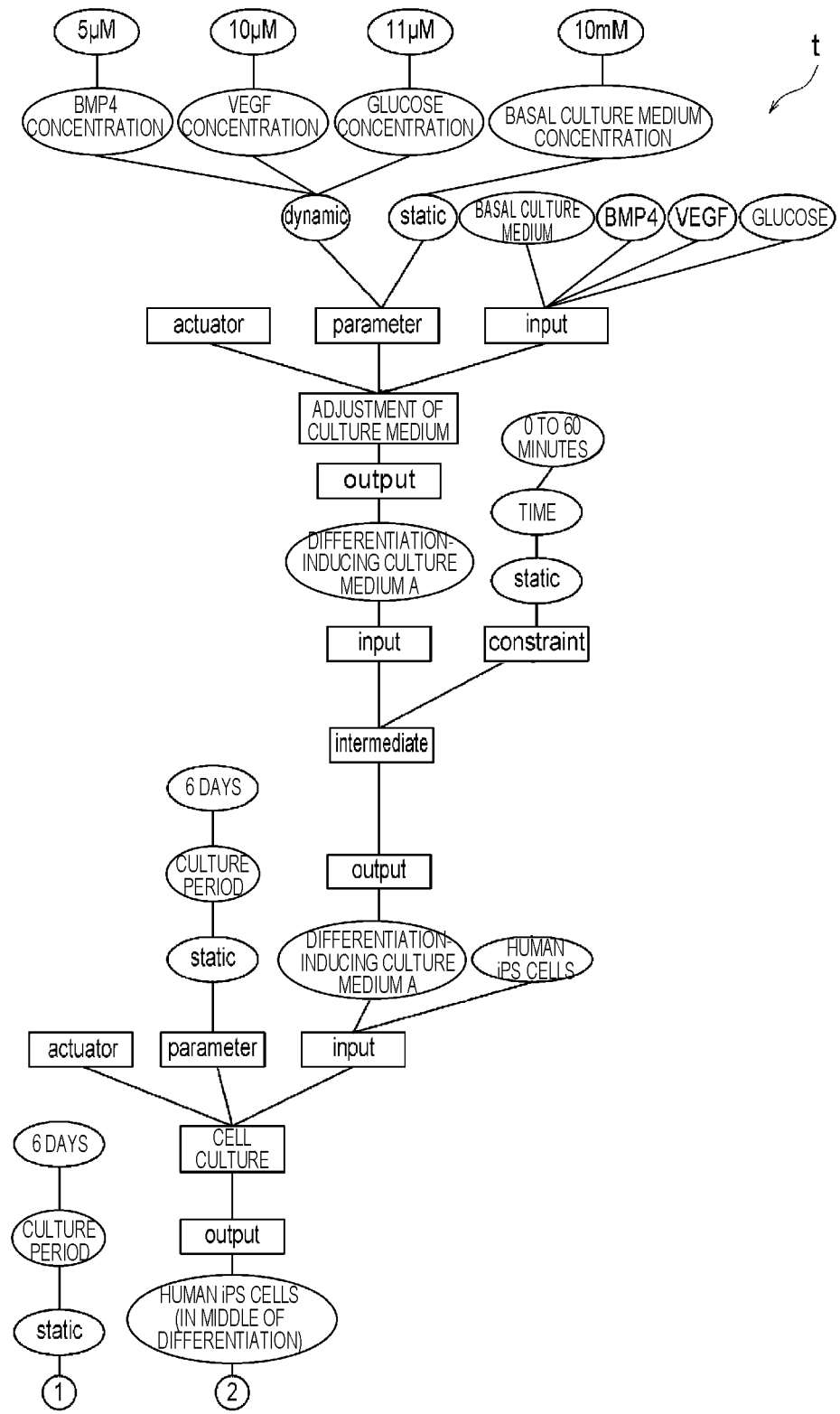
FIG. 9B is a schematic view illustrating a configuration of a continuation of the execution procedure abstract syntax tree shown in FIG. 8.

The execution schedule generation unit 19 generates an execution procedure abstract syntax tree t shown in FIG. 8, FIG. 9A, and FIG. 9B on the basis of the execution procedure shown in FIG. 6. The execution procedure abstract syntax tree is a syntax tree that is a data structure in which an execution procedure is subjected to syntax analysis, and the dependency between the respective operations specified by the execution procedure, the processing targets of the operations, the outcomes obtainable by the operations, and the constraint conditions related to the operations can be analyzed.

The execution procedure abstract syntax tree t as a syntax tree has a data structure in the form of a tree structure in which the contents of the operation item 26a, the input item 26b, the output item 26c, the execution parameter item 26d, the variable parameter item 26g, and the constraint condition item 26e as specified in the operation outline fields C1, C2, C3, and C4 in the execution procedure are set as nodes, and the dependency between the operations is specified by connecting these nodes with edges.

In this case, the execution schedule generation unit 19 can set the contents of the operation item 26a, the input item 26b, the output item 26c, the execution parameter item 26d, the variable parameter item 26g, and the constraint condition item 26e as nodes for each of the operation outline fields C1, C2, C3, and C4 in the execution procedure, individually generate each of individual abstract syntax trees for which dependency is specified by connecting these nodes with edges, and generate an execution procedure abstract syntax tree t by associating these individual abstract syntax trees with each other on the basis of a progress sequence of the operations of the execution procedure.

The details of the individual abstract syntax tree generation process and the execution procedure abstract syntax tree generation processing, by which the individual abstract syntax trees and execution procedure abstract syntax tree t are generated from the execution procedure, will be described below.

Next, the execution schedule generation unit 19 generates an extended abstract syntax tree (will be described below) in which the execution subjects executing each of the operations in the execution procedure are associated with the execution procedure abstract syntax tree t, on the basis of execution environment information (will be described below) received from the execution environment 100 through the transmission/reception unit 11, and the above-mentioned execution procedure abstract syntax tree t.

The extended abstract syntax tree as a syntax tree is a syntax tree that is a data structure in which the execution procedure is subjected to syntax analysis, and the dependency between the respective operations specified by the execution procedure, the processing target of the operations, the outcomes obtainable by the operations, the constraint conditions related to the operations, and the execution subject executing each operation in the execution procedure can be analyzed.

Here, FIG. 10A illustrates an example of the configuration of execution environment information E. As shown in FIG. 10A, the execution environment information E is information indicating a candidate of the execution subject that can actually execute each operation specified in the execution procedure in the execution environment 100, an execution time taken when the execution subject executes the operation, and an execution unavailable time (usage circumstances) for which it is impossible to use the execution subject for the operation.

With regard to the execution environment information E shown in FIG. 10A, it is specified that the operation of "Adjustment" indicated in the operation outline fields C1 and C3 of the execution procedure can be executed by the culture medium mixing device P but cannot be executed by the cell culture devices X and Y and the flow cytometer Q, and the execution time required when the culture medium mixing device P executes the "Adjustment" (30 minutes for the adjustment of the culture medium A, and 30 minutes for the adjustment of the culture medium B) is specified.

With regard to the execution environment information E, for example, a temperature, a humidity, and the like appropriate for reaching the intended state of the culture media A and B may be specified for the device as an execution subject (here, the culture medium mixing device P). In addition to that, in the execution environment information E, information related to the function or performance of a machine as an execution subject, such as the operation accuracy of the machine, or a standby time, may be specified.

With regard to the execution environment information E, it is specified that the operation of "Culture" indicated in the operation outline field C2 of the execution procedure can be executed by the cell culture devices X and Y but cannot be executed by the culture medium mixing device P and the flow cytometer Q, and the execution time required when the cell culture devices X and Y execute the "Cell culture" (the cell culture device X requires 6 days for culture using the culture media A and B, and the cell culture device Y requires 6 days for culture using the culture media A and B) is specified.

Furthermore, with regard to the execution environment information E, it is specified that the operation of "Marker gene expression evaluation" indicated in the operation outline field C5 of the execution procedure can be executed only by the flow cytometer Q but cannot be executed by the culture medium mixing device P and the cell culture devices X and Y, and the execution time required when the flow cytometer Q executes the "Marker gene expression evaluation" (the flow cytometer Q requires 60 minutes for the marker gene expression evaluation) is specified.

In the execution environment information E, an execution unavailable time indicating that the cell culture device X cannot execute the operation of the execution procedure from 17:00 on Jan. 3, 2020, to 17:00 on Jan. 6, 2020, is specified, and an execution unavailable time indicating that the cell culture device Y cannot execute the operation of the execution procedure from 17:00 on Jan. 12, 2020, to 17:00 on Jan. 15, 2020, is specified, as the use circumstances.

In the execution environment information E according to the present embodiment, a case is described in which as a use circumstance indicating the availability of an operation for the execution subject, the execution unavailable time for which the execution subject cannot execute the operation is specified; however, the invention is not limited to this. For example, execution environment information E in which as a use circumstance indicating the availability of an operation for the execution subject, the execution available time for which the execution subject can execute the operation (for example, from 09:00 to 16:00 on Jan. 2, 2020) is specified, may be applied. These execution unavailable time and the execution available time are simply referred to as usage circumstances.

In the present embodiment, a predetermined information processing device (not shown in FIG. 1) in the execution environment 100 may generate execution environment information E by summarizing individual information of each execution subject (which execution subject can execute which operation, the execution time, and the usage circumstances), and the culture-related process optimization device 2 may receive the execution environment information E generated by the information processing device on the execution environment 100 side. In addition, each execution subject in the execution environment 100 may transmit each own individual information to the culture-related process optimization device 2 through the communication devices 3a, 3b, 3c, and 3d, and the execution environment information E may be generated by summarizing individual information at the arithmetic processing unit 7 of the culture-related process optimization device 2.

The execution schedule generation unit 19 identifies an operation node that is required to be allocated to an execution subject node (denoted as "Actuator" in FIG. 8, FIG. 9A, and FIG. 9B) included in the execution procedure abstract syntax tree t, allocates the execution subject specified by the execution procedure abstract syntax tree t from the acquired execution environment information E and the execution procedure abstract syntax tree t, first without considering the constraint conditions, to the execution subject node ("Actuator") of each operation node of the execution procedure abstract syntax tree t, and obtains a set A' in which each execution subject is allocated to each operation, as shown in FIG. 11.

Here, the set A' shows a combination pattern by allocating all the execution subjects capable of executing the operations to the execution subject nodes in the execution procedure abstract syntax tree t, respectively, without considering the constraint condition.

Figure 12:
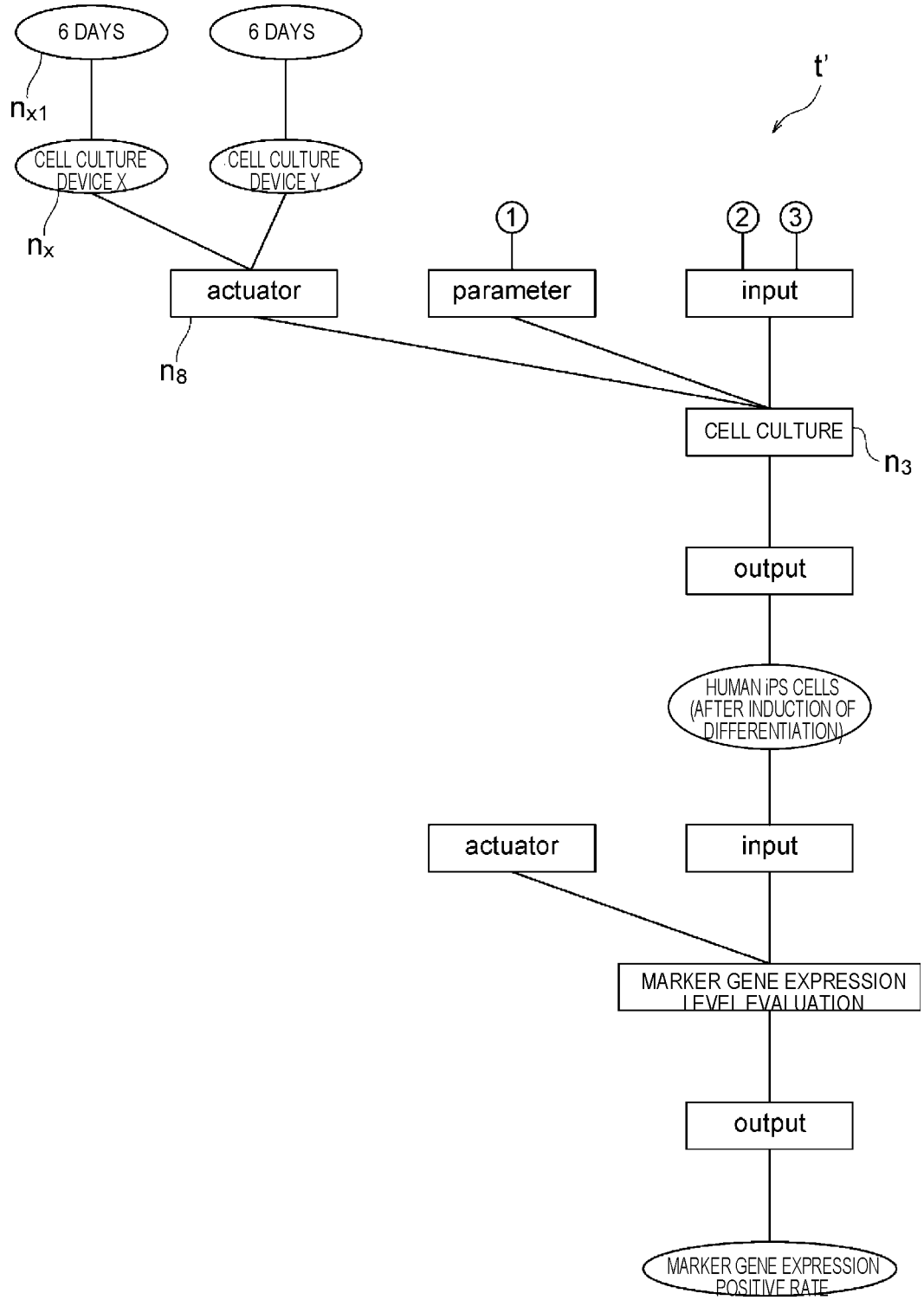
FIG. 12 is a schematic view illustrating an example of a configuration of an extended abstract syntax tree.
Figure 13:
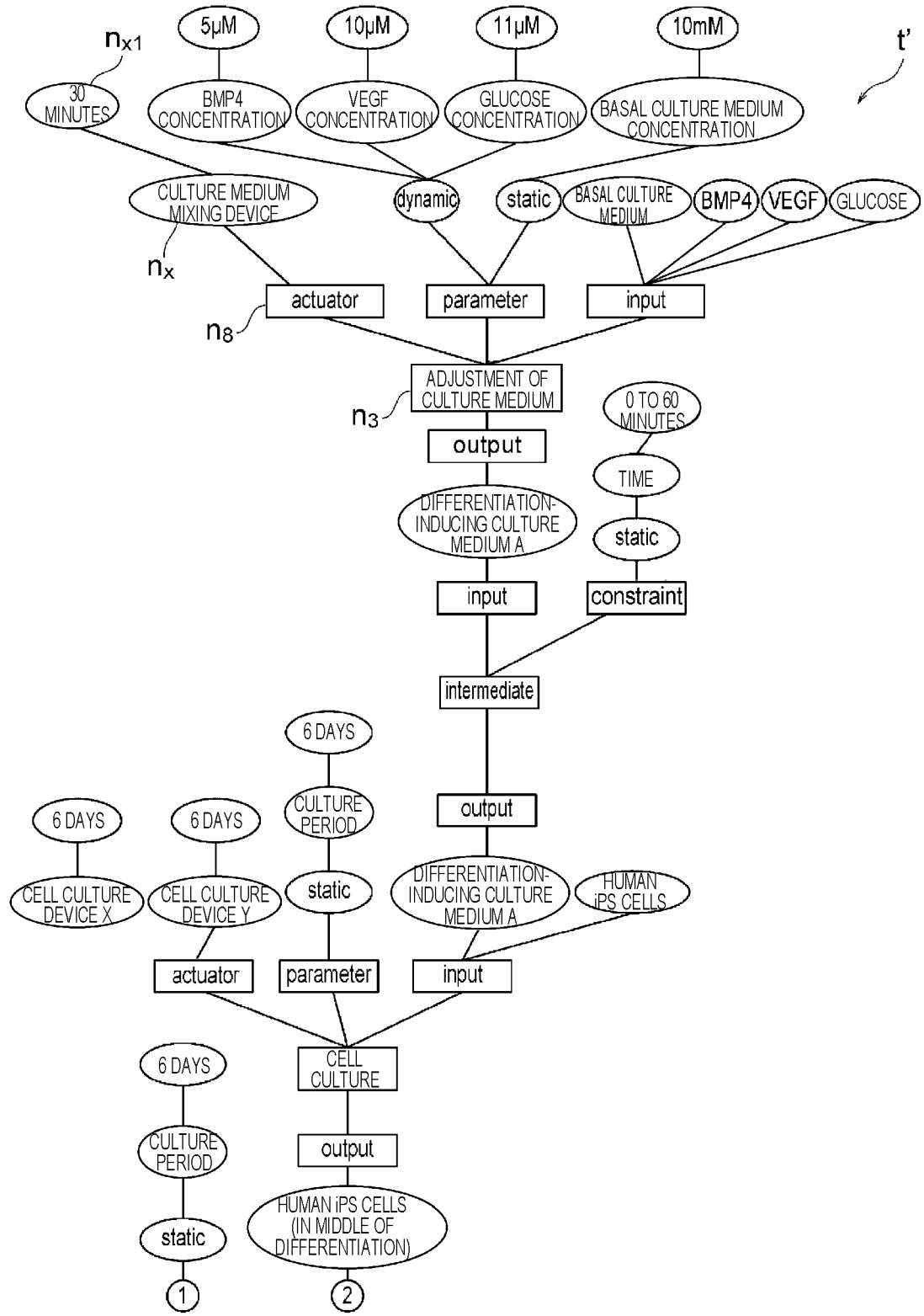
FIG. 13 is a schematic view illustrating a configuration of a continuation of the extended abstract syntax tree shown in FIG. 12.
Figure 14:
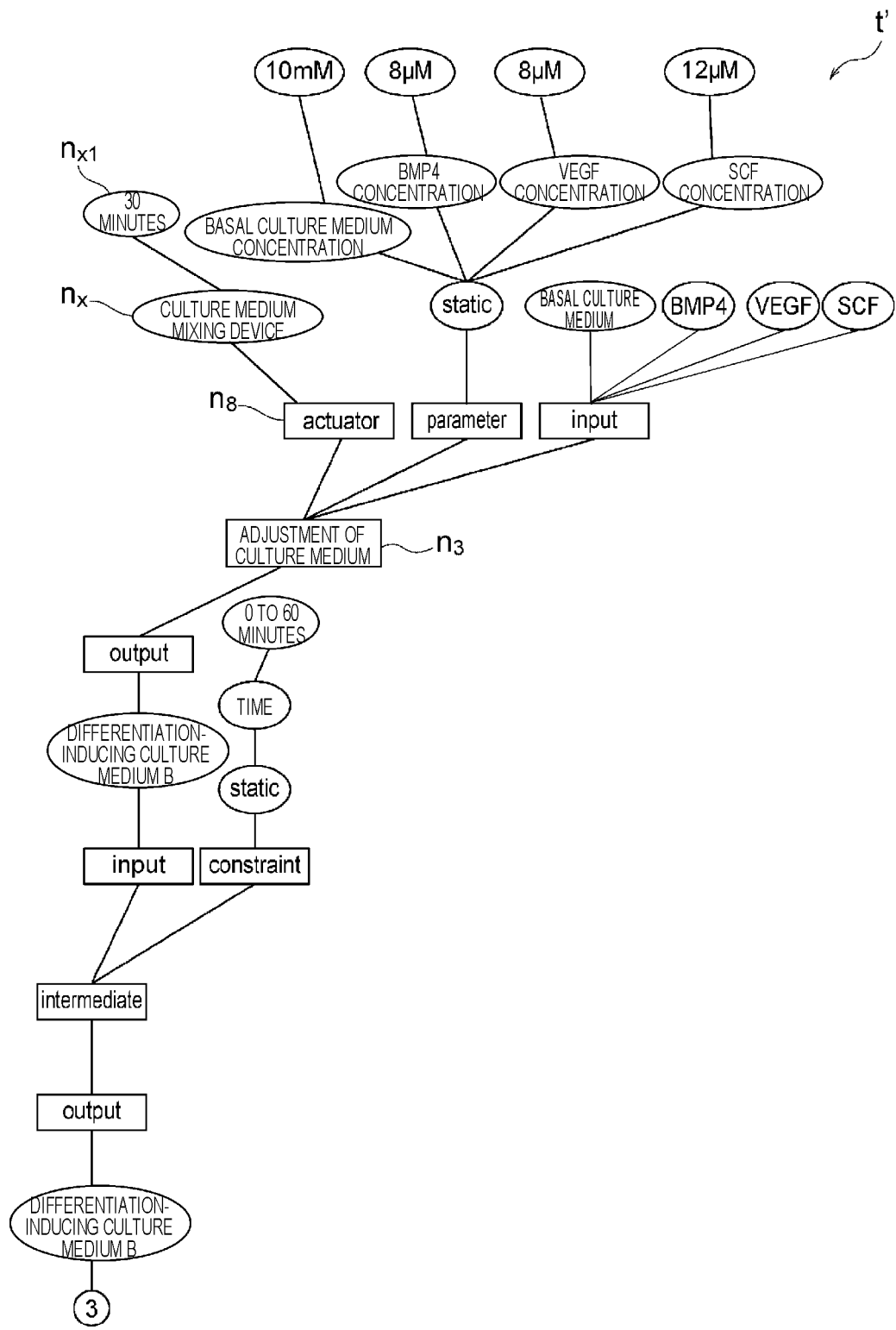
FIG. 14 is a schematic view illustrating a configuration of a continuation of the extended abstract syntax tree shown in FIG. 12.

The execution schedule generation unit 19 reflects the result of the set A' in which an execution subject is allocated to each operation, onto the execution subject nodes in the execution procedure abstract syntax tree t, and generates an extended abstract syntax tree t' as shown in FIG. 12, FIG. 13, and FIG. 14.

FIG. 12, FIG. 13, and FIG. 14 illustrate an example of the extended abstract syntax tree t' that is a data structure in the form of a tree structure in which execution subjects of the execution environment information E shown in FIG. 10A are allocated to the execution procedure shown in FIG. 6, and an execution subject, an execution time, and a constraint condition are associated with a series of operations including from the adjustment of the culture media A and B to cell culture and marker gene expression evaluation. The generation of such an extended abstract syntax tree t' will be described below.

Figure 10B:
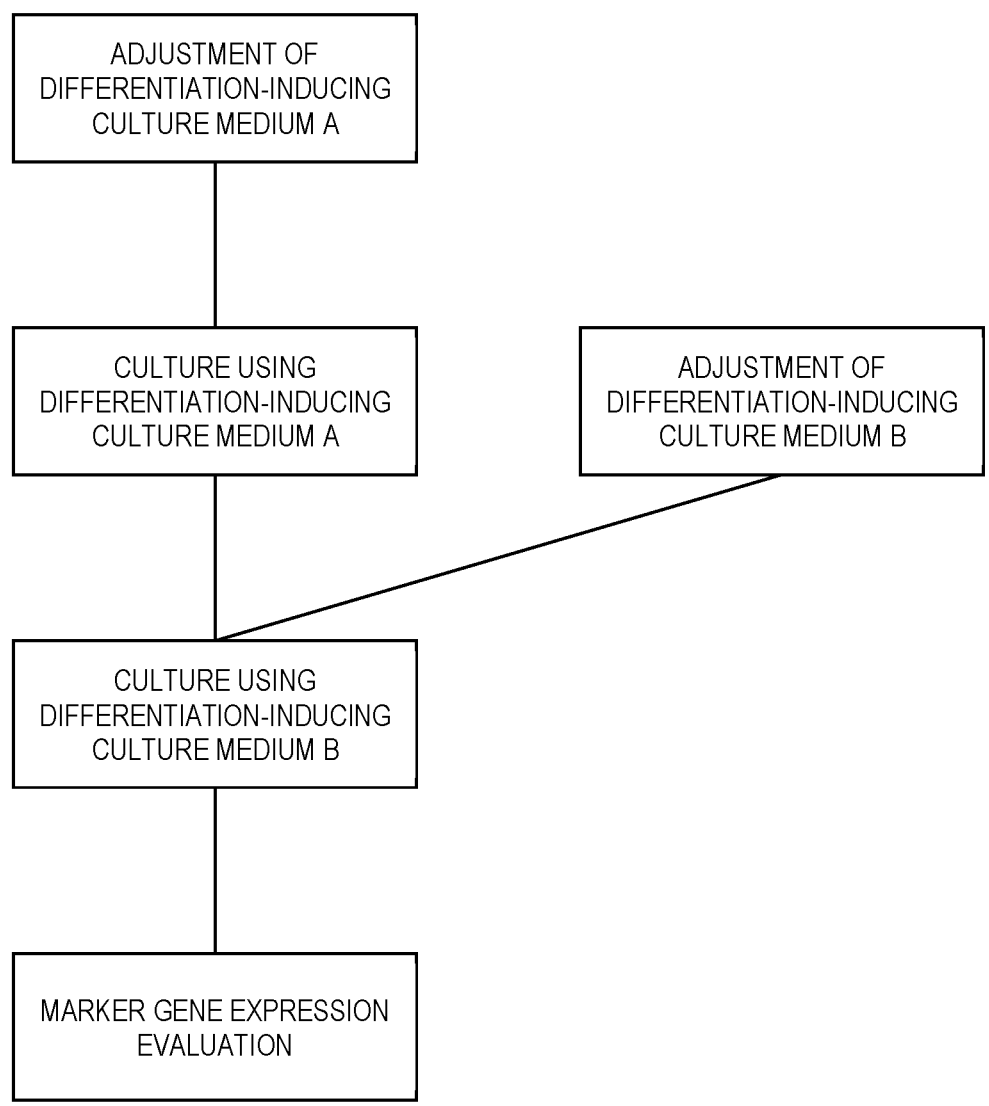
FIG. 10B is a schematic view illustrating a configuration of a partial order.

Next, the execution schedule generation unit 19 generates a partial order indicating operations that can be executed in series and operations that can be executed in parallel among the series of operations executed sequentially, as shown in FIG. 10B, on the basis of the extended abstract syntax tree t'. The execution schedule generation unit 19 determines the start hour for starting the execution procedure (here, set to 08:30 on Jan. 2, 2020), allocates the execution start time and the execution end hour to each element of the set A' according to the sequence for executing the operations, on the basis of the partial order by which concurrency constraints can be analyzed for the series of operations of the execution procedure, and obtains a set A" as shown in FIG. 15.

In an execution procedure in which a plurality of operations can be executed simultaneously, simultaneously inexecutable operations and simultaneously executable operations are specified as a concurrency constraint between the respective operations, and this concurrency constraint can be reflected on the extended abstract syntax tree t' or the partial order. In addition, in the concurrency constraint, whether the time efficiency in the entire culture-related process can be improved by performing only the adjustment of the culture medium B in parallel with cell culture using the culture medium A, is also specified.

Here, the set A" in FIG. 15 has a combination pattern in which the execution start hour and the execution end hour at which each execution subject can execute the execution are allocated to each operation according to the sequence of the operations sequentially executed in the execution procedure from a predetermined start hour (08:30 on Jan. 2, 2020), without considering the constraint conditions in the execution procedure.

For example, "No. 2" of the set A" in FIG. 15 shows a time allocation schedule in which, for the "Culture using differentiation-inducing culture medium A" and "Adjustment of differentiation-inducing culture medium B" with no concurrency constraint, the "Culture using differentiation-inducing culture medium A" is executed by "Cell culture device X" until 17:00 on Jan. 13, 2020, subsequently the next "Adjustment of differentiation-inducing culture medium B" is executed using the "Culture medium mixing device P" a few days later from 16:30 on Jan. 15, 2020, and then the "Culture using differentiation-inducing culture medium B" by the "Cell culture device Y" and the "Marker gene expression evaluation" by the "Flow cytometer Q" are executed sequentially.

In addition, "No. 4" of the set A" in FIG. 15 shows a time allocation schedule in which, for the "Culture using differentiation-inducing culture medium A" and "Adjustment of differentiation-inducing culture medium B" with no concurrency constraint, the "Culture using differentiation-inducing culture medium A" by "Cell culture device Y" (from 09:00 on Jan. 2, 2020, until 09:00 on Jan. 8, 2020) and the "Adjustment of differentiation-inducing culture medium B" by "Culture medium mixing device P" (from 08:30 on Jan. 8, 2020, until 09:00 on Jan. 8, 2020) are executed in parallel, and immediately thereafter, the "Culture using differentiation-inducing culture medium B" by the "Cell culture device X" and the "Marker gene expression evaluation" by the "Flow cytometer Q" are executed.

In "No. 3" and "No. 5" of the set A" in FIG. 15, after the "Adjustment of differentiation-inducing culture medium B" by the "Culture medium mixing device P" is ended, the "Culture using differentiation-inducing culture medium B" by the "Cell culture device Y" is executed after a lapse of a time longer than 60 minutes, and for the operation outline field C4 related to the "Cell culture using differentiation-inducing culture medium B (target cell differentiation)" in the execution procedure shown in FIG. 6, the constraint condition of "Within 60 minutes after adjustment of differentiation-inducing culture medium B is finished" as specified in the constraint condition item 26e is not satisfied.

As described above, the execution schedule generation unit 19 generates all the combinations of time allocation schedules with a possibility that when the constraint conditions in the execution procedure are not taken into consideration, the operations of the execution procedure can be executed by the execution subject, and obtains such a combination pattern as the set A".

Next, the execution schedule generation unit 19 reads out the constraint condition of each operation (condition specified in the constraint condition item 26e) from the execution procedure, the execution procedure abstract syntax tree t, or the extended abstract syntax tree t', extracts a time allocation schedule in which all the constraints such as the execution time specified in the constraint conditions are satisfied, from the set A" as a candidate schedule, and obtains a set A'" including candidate schedules.

FIG. 16 illustrates an example of the set A'" of combinations satisfying the constraint conditions specified in the constraint condition item 26e. For example, in the execution procedure of FIG. 6, with regard to the operation outline field C4 of the "Cell culture using differentiation-inducing culture medium B", a constraint condition of "Within 60 minutes after adjustment of differentiation-inducing culture medium B is finished" is specified in the constraint condition item 26*e*. Therefore, as shown in FIG. 16, the execution schedule generation unit 19 extracts "No. 1", "No. 2", and "No. 4" satisfying the above-described constraint conditions as candidate schedules, and obtains a set A''' including these candidate schedules. It is noted that "No. 3" and "No. 5" do not satisfy the constraint condition of "Within 60 minutes after adjustment of differentiation-inducing culture medium B is finished" as specified in the constraint condition 26*e* of "Culture using differentiation-inducing culture medium B" and are therefore not included in the set A'''.

Here, in the execution schedule generation unit 19, for example, a selection condition such as selecting a candidate schedule having the earliest execution end time of the "Marker gene expression evaluation", which is the final operation of the execution procedure, is set in advance by the manager. As a result, the execution schedule generation unit 19 selects one candidate schedule corresponding to the selection condition from the set A''' as the final execution schedule.

In the set A''' shown in FIG. 16, the candidate schedule with the earliest execution end time is "No. 4". "No. 4" is a schedule in which the "Culture using differentiation-inducing culture medium A" and the "Adjustment of differentiation-inducing culture medium B" with no concurrency constraint are executed in parallel after the "Adjustment of differentiation-inducing culture medium A", and by executing the "Culture using differentiation-inducing culture medium B" immediately after the "Culture using differentiation-inducing culture medium A" and the "Adjustment of differentiation-inducing culture medium B" are simultaneously completed, the greatest time shortening is realized among "No. 1", "No. 2", and "No. 4". In "No. 2", since concurrency constraint is not taken into consideration, a schedule with the longest execution time is obtained.

In addition, in a case where there are a plurality of candidate schedules with the earliest end time, for example, an index for determining superiority or inferiority is set in addition to the execution end time, and a schedule with a smaller numerical value of the number (No), which is a discriminator of the candidate schedule, is selected as the execution schedule.

The execution schedule generation unit 19 transmits the selected execution schedule to the execution instruction information generation unit 20. The execution instruction information generation unit 20 generates execution instruction information for respectively instructing each execution subject that executes each operation to perform the operation according to the execution schedule, with reference to the execution environment information E.

Here, the execution instruction information is data in which information sufficient to allow the execution subject to execute each operation of the execution procedure in the execution environment 100 according to the execution schedule is described. Typically, setting information such as a program for controlling and operating the culture medium mixing device P, the cell culture devices X and Y, and the flow cytometer Q corresponds to the execution instruction information.

In this way, the arithmetic processing unit 7 transmits each execution schedule and execution instruction information generated for each execution procedure to the transmission/reception unit 11 on the basis of the list of execution procedures, and the execution schedule and the execution instruction information are sent from the transmission/reception unit 11 to each of the communication devices 3*a*, 3*b*, 3*c*, and 3*d* of the corresponding execution subjects through the network 4.

The communication devices 3*a*, 3*b*, 3*c*, and 3*d* that have received the execution schedule and the execution instruction information present the execution schedule and the execution instruction information to the culture medium mixing device P, the cell culture devices X and Y, and the flow cytometer Q, which are respective corresponding execution subjects, and allow the execution subjects to perform each operation in the execution environment 100.

As a result, in the culture-related process optimization system 1, when each execution subject is allowed to execute each operation of the execution procedure on the basis of the execution schedule and the execution instruction information in the execution environment 100, and as a result, when an execution result or an evaluation result of the execution procedure is obtained, these execution result and evaluation result are transmitted every time from the communication devices 3*a*, 3*b*, 3*c*, and 3*d* to the culture-related process optimization device 2.

When the culture-related process optimization device 2 receives the execution result or the evaluation result from the communication devices 3*a*, 3*b*, 3*c*, and 3*d* of the execution environment 100, the culture-related process optimization device 2 records the execution procedure, the variable parameter value set in the execution procedure, the execution result, and the evaluation result in the database 8 in association with each other, and these execution result and the evaluation result are analyzed by the determination unit 18 of the arithmetic processing unit 7.

At this time, when the rescheduling determination unit 23 of the determination unit 18 determines that: (i) the progress of the actual execution procedure in the execution environment 100 is different from the execution schedule, and the execution procedure is not executed according to the execution schedule, or (ii) there is an influence on an unexecuted part in the execution schedule, and it is necessary to change the execution schedule, the rescheduling determination unit 23 regenerates the execution schedule and execution instruction information for executing the execution procedure according to the execution schedule.

For example, when the cell culture device X executes the execution procedure according to an execution schedule in which culture using the culture medium A is executed by the cell culture device X, and thereafter, culture using the culture medium B is also executed by the same cell culture device X, in a case where an execution result that the cell culture device X requires a time longer than expected in the culture using the culture medium A, and the execution of subsequent culture using the culture medium B by the cell culture device X is delayed, is received from the cell culture device X, the determination unit 18 determines that the execution procedure of the cell culture device X is not executed according to the execution schedule, and regenerates the execution schedule and the execution instruction information.

On the other hand, for example, when the cell culture device X and the culture medium mixing device P execute the execution procedure according to an execution schedule in which culture using the culture medium A is executed by the cell culture device X, and adjustment of the culture medium B is executed by the culture medium mixing device P in parallel, even in a case where the cell culture device X requires a time longer than expected in the culture using the culture medium A, there is no influence on the adjustment of the culture medium B by the culture medium mixing device P, and operations such as the adjustment of the culture medium B and subsequent cell culture in the culture medium B using the cell culture devices X and Y can be executed according to the execution schedule. In such a case, even when the determination unit 18 receives from the cell culture device X an execution result that culture using the culture medium A requires time and cannot be executed according to the execution schedule, the determination unit 18 determines that there is no influence on the unexecuted parts (for example, adjustment of the culture medium B, cell culture in the culture medium B using the cell culture devices X and Y, and marker gene expression evaluation) in the execution schedule, and it is not necessary to change the execution schedule.

That is, the determination unit 18 not only simply determines whether all the execution subjects execute the execution according to the execution schedule, but also determines whether, even in a case where some execution subjects in the execution environment 100 do not execute the execution according to the execution schedule, the operations of the some execution subjects do not affect the operations of other execution subjects, the other execution subjects execute the operation according to the execution schedule, and the execution procedure is finally ended until an end date presented by the execution schedule.

In this example, the determination unit 18 determines that even in a case where some execution subjects in the execution environment 100 do not execute the execution according to the execution schedule, when the execution procedure is finally ended until the end date presented by the execution schedule, execution according to the execution schedule is made possible, and it is not necessary to change the execution schedule.

When the execution schedule and the execution instruction information are regenerated, the culture-related process optimization device 2 transmits the regenerated execution schedule and execution instruction information again to the communication devices 3*a*, 3*b*, 3*c*, and 3*d* of the respective corresponding execution subjects, presents a new execution schedule and new execution instruction information to the culture medium mixing device P, the cell culture devices X and Y, or the flow cytometer Q, which are the respective corresponding execution subjects, and allows the execution subjects to perform each operation in the execution environment 100.

In addition, when the continuous determination unit 22 of the determination unit 18 receives the execution result and the evaluation result from the communication devices 3*a*, 3*b*, 3*c*, and 3*d* of the execution environment 100, the continuous determination unit 22 determines again whether to search for new variable parameter values reflecting the execution result and the evaluation result at the variable parameter value setting unit 16 based on the execution result and evaluation result received from the communication devices 3*a*, 3*b*, 3*c*, and 3*d* in the execution environment 100, on the basis of whether a continuous command is given from the manager through the operation unit 10, whether the evaluation result is a desired evaluation result, or whether the evaluation result is obtained a predetermined number of times.

When a continuous command is given, for example, from the manager through the operation unit 10, the continuous determination unit 22 allows the variable parameter value setting unit 16 to generate again a regression model (response surface) including the newly obtained execution result and evaluation result. As a result, the arithmetic processing unit 7 allows the variable parameter value setting unit 16 to newly select a plurality of variable parameter values from within the search range by using this regression model through Bayesian optimization, multitask Bayesian optimization, or the like, and allows the execution procedure generation unit 17 to generate a list of a plurality of execution procedures in which the variable parameter values are different or the same.

When a list of execution procedures having the same variable parameter values is generated, the execution procedure generation unit 17 allows the execution subjects in the execution environment 100 to execute the same execution procedures a plurality of times; however, it is effective, for example, from the viewpoints of verification of certainty of the execution procedure, verification of whether the same evaluation results are obtained, and the like. More specifically, in a case where it can be anticipated that the noise of the execution result or the evaluation result of the culture-related process will be large (a case where even though the evaluation result obtained by predetermined variable parameter values is greater than the previous maximum value by 5%, it is not obvious from one observation whether such a state is due to the noise or an actual improvement), a statistic quantity such as a standard deviation or an average is obtained, and evaluation with higher accuracy can be performed.

In this way, the culture-related process optimization device 2 generates again the execution schedule and execution instruction corresponding to the newly generated execution procedure, transmits again these execution schedule and execution instruction to the communication devices 3*a*, 3*b*, 3*c*, and 3*d* of the execution subjects in the execution environment 100, presents the execution schedule and execution instruction information to the culture medium mixing device P, the cell culture devices X and Y, and the flow cytometer Q, which are the respective corresponding execution subjects in the execution environment 100, and allows the culture medium mixing device P, the cell culture devices X and Y, and the flow cytometer Q in the execution environment 100 to perform each operation.

Thus, the culture-related process optimization system 1 repeatedly performs the generation of an execution schedule and execution instruction information, presentation of the execution schedule and the execution instruction information to the execution subjects (culture medium mixing device P, cell culture devices X and Y, and flow cytometer Q), acquisition of an execution result and an evaluation result from the execution subjects on the basis of this presentation, and setting of new variable parameter values reflecting the obtained execution result and evaluation result.

As a result, in the culture-related process optimization system 1, optimal variable parameter values and execution schedule in which a gain as large as possible is obtained can be searched for while reflecting the execution result and the evaluation result obtained as the execution subjects actually execute the culture-related process in the execution environment 100, and an optimal culture-related process with a large gain can be sought.

Next, an outline of the above-mentioned culture-related process optimization method will be described by using a flowchart in FIG. 17A. In the culture-related process optimization system 1, in reality, it is desirable that a plurality of execution schedules and execution instruction information generated for each of the listed execution procedures are presented to each execution subject, and a plurality of different execution procedures are simultaneously executed in the execution environment 100; however, in that case, an execution result and an evaluation result may be received each time for each of the different execution procedures. Such a case will be described by using FIG. 17B, and in the flowchart of FIG. 17A, in order to simplify the description, processing with respect to one execution procedure will be mainly described below.

Figure 17A:
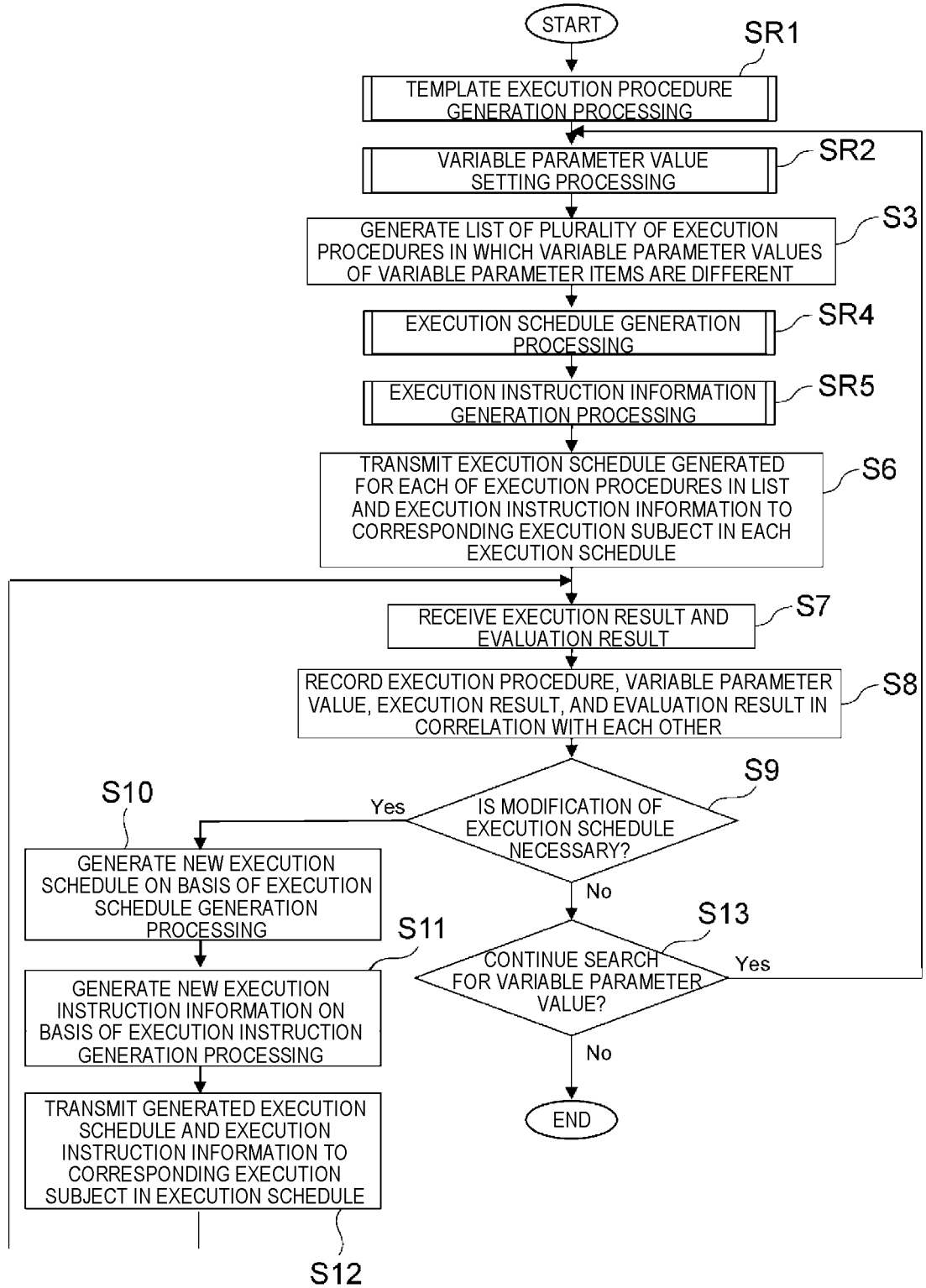
FIG. 17A is a flow chart illustrating a culture-related process optimization processing procedure according to the present embodiment.

As shown in the flowchart of FIG. 17A, the culture-related process optimization device 2 starts a culture-related process optimization processing procedure from a start step, performs template execution procedure generation processing in a subroutine SR1, and generates a template execution procedure. The culture-related process optimization device 2 performs variable parameter value setting processing in a next subroutine SR2 and selects a plurality of variable parameter values in the search range for the variable parameter item 26g specified in the template execution procedure.

In a next step S3, the culture-related process optimization device 2 generates a list of a plurality of execution procedures in which the variable parameter values of the variable parameter item 26g are different (or the same). In a next subroutine SR4, the culture-related process optimization device 2 performs execution schedule generation processing and generates an execution schedule for each of the execution procedures generated in the step S3. In a next subroutine SR5, the culture-related process optimization device 2 performs execution instruction information generation processing and generates execution instruction information of the execution schedule generated in the subroutine SR4.

In a next step S6, the culture-related process optimization device 2 transmits the execution schedule and execution instruction information generated for each of the execution procedures in the list to the respective corresponding execution subjects in the execution schedule. As a result, the culture-related process optimization system 1 allows each execution subject to perform the respective operations of the execution procedure according to the execution schedule and execution instruction information in the execution environment 100.

In a next step S7, the culture-related process optimization device 2 receives the execution result and evaluation result obtained in the execution environment 100 at the transmission/reception unit 11, and in a next step S8, the culture-related process optimization device 2 records the execution procedure executed by the execution subject in the execution environment 100 on the basis of the execution schedule and the execution instruction information, the variable parameter values at this time, the execution result acquired from the execution environment 100, and the evaluation result acquired from the same execution environment 100, in association with each other in the database 8.

In a next S9, the culture-related process optimization device 2 decides whether the execution procedure is executed according to the execution schedule presented to the execution subjects from the execution result, the evaluation result, and the like. Here, in a case where the execution procedure is not executed according to the execution schedule presented to the execution subjects, it is considered that the execution schedule needs to be changed (Yes), and in a step S10, the culture-related process optimization device 2 analyzes unexecuted parts of the execution schedule and generates an execution schedule that can be executed in the execution environment 100, by execution schedule generation processing.

Furthermore, the culture-related process optimization device 2 generates execution instruction information of the newly generated execution schedule in a next step S11 and transmits the newly generated execution schedule and execution instruction information to the corresponding execution subjects in the execution schedule in a next step S12.

On the other hand, in a case where the execution procedure is executed according to the execution schedule presented to the execution subjects in the step S9, it is not necessary to change the execution schedule (No), and the culture-related process optimization device 2 reflects the execution result and evaluation result acquired from the execution subjects in the execution environment 100 in a next step S13 and decides whether to search for optimal variable parameter values again in the search range of the template execution procedure.

For example, in a case where a continuous command for search of the variable parameter values through the operation unit 10 is given to the manager who checked the execution result and the evaluation result acquired from the execution subjects in the execution environment 100, in a case where it is set to perform a search for the variable parameter values until an evaluation result set in advance for the evaluation result acquired from the execution subjects in the execution environment 100 is obtained, in a case where it is set to perform a search for the variable parameter values only a predetermined number of times after the execution result and the evaluation result are acquired from the execution subjects in the execution environment 100, or the like, optimal variable parameter values are searched again from within the search range of the template execution procedure (Yes).

In this case, the culture-related process optimization device 2 returns again to the subroutine SR2 and repeats the above-mentioned processing until a negative result (No) is obtained in the step S13. On the other hand, in the step S13, in a case where the culture-related process optimization device 2 decides that optimal variable parameter values are not searched again in the search range of the template execution procedure, the above-mentioned culture-related process optimization process is ended.

Here, the flowchart of FIG. 17A focuses on one execution procedure in order to simplify the description, and it is described that when the optimal execution result and evaluation result are obtained, the culture-related process optimization processing is ended. Thus, an outline of the processing of the culture-related process optimization device 2 in which a plurality of execution schedules and execution instruction information pieces are presented to the execution subjects, and the culture-related process optimization device 2 receives each execution result, each evaluation result, and the like of the plurality of different execution procedures from each execution subject, will be described by using FIG. 17B.

Figure 17B:
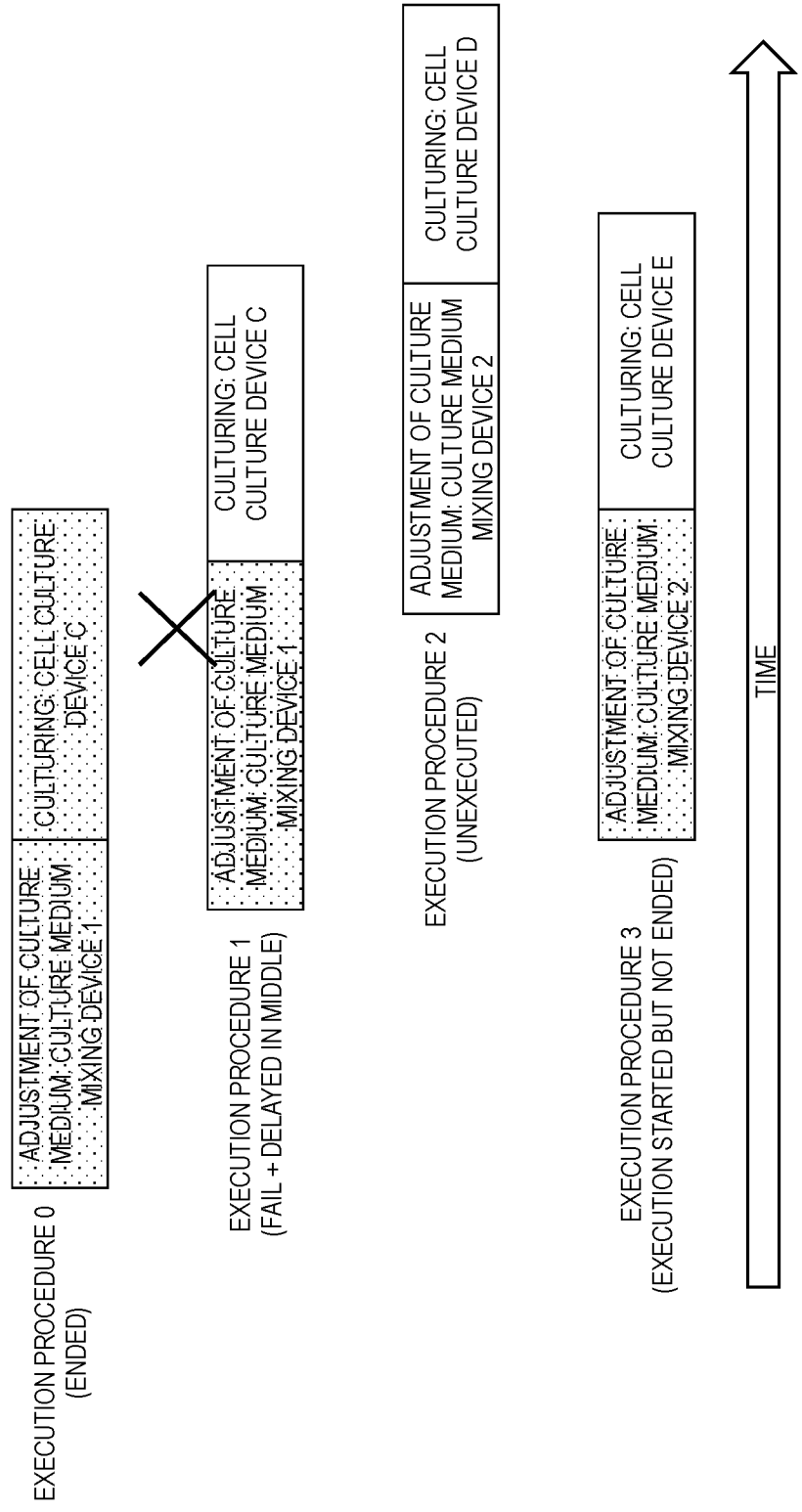
FIG. 17B is a schematic view for describing an occasion of executing a plurality of execution procedures.

The example shown in FIG. 17B shows an example in which four execution procedures 0, 1, 2, and 3 are presented as the execution procedure of the culture-related process. As described above, in the culture-related process optimization system 1, it is desirable that a plurality of different execution procedures are presented to each execution subject through the execution schedules and execution instruction information, and a plurality of different execution procedures are executed in parallel in the execution environment 100.

Here, with regard to the execution procedure 0, it is assumed that adjustment of the culture medium A, cell culture using the culture medium A, adjustment of the culture medium B, and cell culture using the culture medium B are ended, and an optimal execution result is obtained. On the other hand, with regard to the execution procedure 1, it is assumed that adjustment of the culture medium A (or adjustment of the culture medium B) is failed or delayed, and an execution result in which there is an unexecuted operation (culturing) due to the influence thereof, is obtained. It is assumed that the execution procedure 2 has not been executed, the execution procedure 3 is currently being executed, and no execution result has been obtained from the respective execution procedures.

In this case, as shown in FIG. 17B, the culture-related process optimization device 2 receives the execution result of the execution procedure 0 and then receives an execution result that adjustment of the culture medium A or adjustment of the culture medium B is failed or delayed in the other execution procedure 2, and due to the influence thereof, there is an unexecuted operation (culturing).

In this case, in the culture-related process optimization device 2, the execution result of the optimal execution procedure 0 is stored in the database 8 and is utilized for the generation of a regression model the next and subsequent times. In addition, in the culture-related process optimization device 2, even after an optimal execution result is received with regard to the execution procedure 0, the culture-related process optimization processing is not ended immediately, and the execution result of the execution procedure 1 that is subsequently obtained is also stored in the database 8. Even such a non-optimal execution result may be utilized as necessary as reference data the next and subsequent times when a new execution procedure is generated.

As described above, in the culture-related process optimization system 1, it is desirable that without focusing only on one execution procedure 0 and terminating the culture-related process optimization processing, the execution results and evaluation results of other execution procedures 1, 2, and 3 are also acquired as necessary and accumulated in the database 8, and in accordance with the circumstances, the culture-related process optimization processing is ended according to the decision of the manager or the like.

Figure 18:
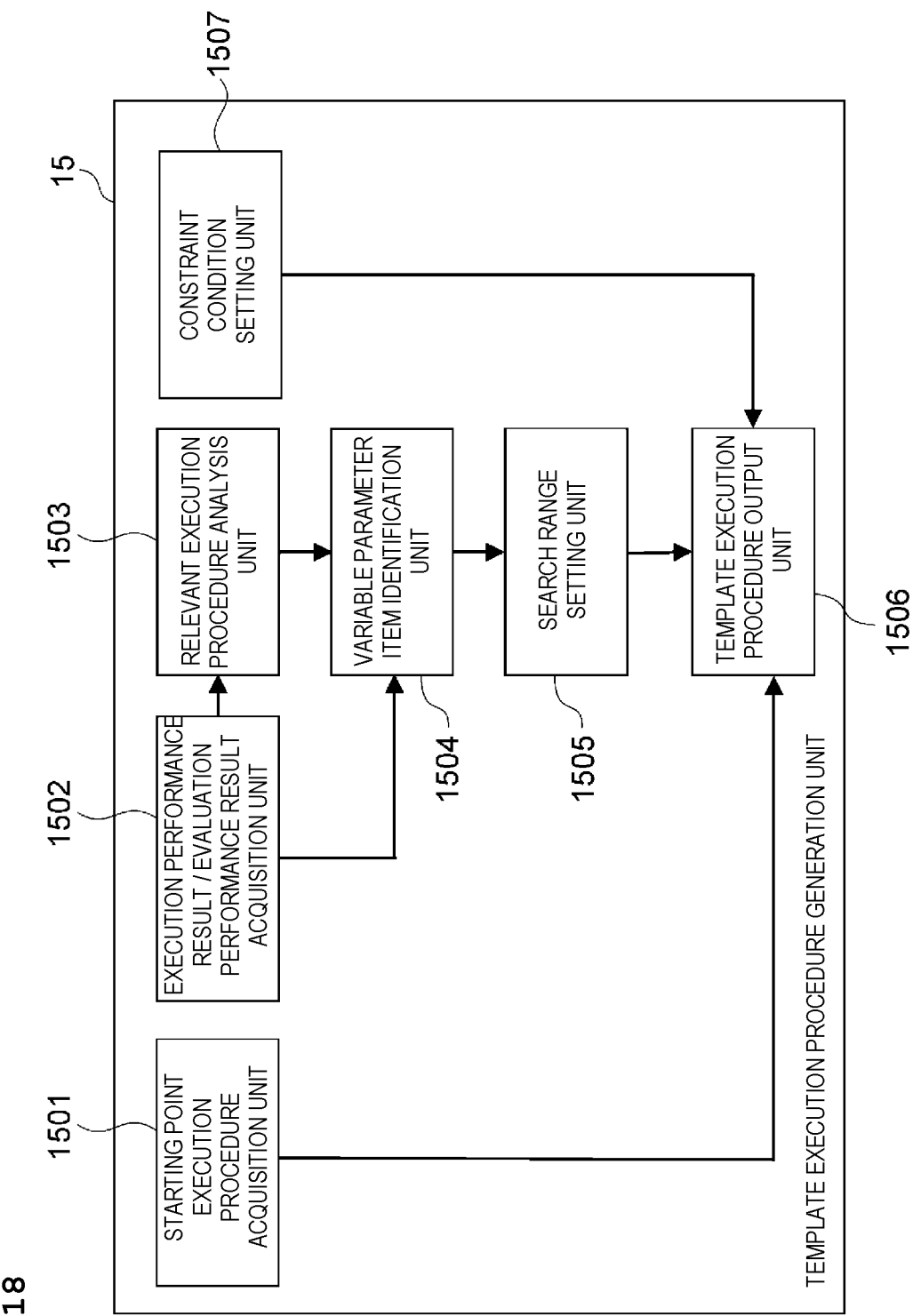
FIG. 18 is a block diagram illustrating a configuration of a template execution procedure generation unit.

(1-2) Template Execution Procedure Generation Processing (1-2-1) Configuration of Template Execution Procedure Generation Unit Next, the template execution procedure generation processing for generating the above-mentioned template execution procedure will be described. FIG. 18 is a block diagram illustrating the configuration of the template execution procedure generation unit 15. As shown in FIG. 18, the template execution procedure generation unit 15 includes a starting point execution procedure acquisition unit 1501, an execution performance result/evaluation performance result acquisition unit 1502, a relevant execution procedure analysis unit 1503, a variable parameter item identification unit 1504, a search range setting unit 1505, a template execution procedure output unit 1506, and a constraint condition setting unit 1507.

Here, the starting point execution procedure acquisition unit 1501 acquires a starting point execution procedure that is the starting point of optimization, with the contents (for example, processing target, outcome, and operation) being common, as shown in FIG. 2, to the contents of the culture-related process and the evaluation process, such as "Adjustment of differentiation-inducing culture medium A", "Culture using differentiation-inducing culture medium A", "Adjustment of differentiation-inducing culture medium B", "Culture using differentiation-inducing culture medium B", and "Marker gene expression evaluation", which have been inputted through the operation unit 10, from the database 8.

The execution performance result/evaluation performance result acquisition unit 1502 acquires, as shown in FIG. 3 and FIG. 4, the execution performance result and the evaluation performance result of the same execution procedure as the starting point execution procedure, or in a case where there are no execution performance result and evaluation performance result of the same execution procedure as the starting point execution procedure in the database 8, the execution performance result and the evaluation performance result of an execution procedure (relevant execution procedure) relevant to the starting point execution procedure from the database 8, on the basis of the contents of the culture-related process and evaluation process inputted through the operation unit 10 and the contents of the operation outline fields of the starting point execution procedure.

Here, a case has been described in which the same execution performance result and evaluation performance result as the contents of the culture-related process and the evaluation process inputted through the operation unit 10 and the contents of the operation outline fields in the starting point execution procedure are acquired from the database 8; however, for example, an execution performance result and an evaluation performance result having similarity with the content of the inputted culture-related process and evaluation process, or an execution performance result and evaluation performance result having similarity with the contents of the operation outline fields in the starting point execution procedure may be acquired from the database 8.

Here, the similarity is determined from, for example, the operation contents included in the culture-related process and evaluation process (hereinafter, collectively referred to as processes) and the sequence thereof, the names and characteristics of the inputs and outputs of the processes. In the case of the operation contents and the sequence thereof, it is desirable to compare normalized intermediate representations. Specifically, for example, a distance between the abstract syntax tress of the processes is determined. In addition, a tree automaton that accepts abstract syntax trees expressing similar processes on the basis of the abstract syntax tree of one process is created, and whether the abstract syntax trees are accepted is determined. With regard to the comparison of inputs and outputs of the processes, it is desirable to compare, in the case of the culture medium or cells, simply the distances between the names, and characteristic values such as the content of each component in the culture medium, and the genotype of the cells.

By specifying in advance such a definition of the similarity in the execution performance result/evaluation performance result acquisition unit 1502, an execution performance result and an evaluation performance result having similarity with the contents of the inputted culture-related process and evaluation process, and an execution performance result and an evaluation performance result having similarity with the contents of the operation outline fields in the starting point execution procedure can be acquired from the database 8.

When there are no execution performance result and evaluation performance result of the same execution procedure as the starting point execution procedure in the database 8, and the execution performance result and the evaluation performance result of an execution procedure (relevant execution procedure) relevant to the starting point execution procedure are read out from the database 8, the relevant execution procedure analysis unit 1503 analyzes the execution performance result and the evaluation performance result of the relevant execution procedure in order to identify the variable parameter item and a search range thereof from the starting point execution procedure. A case in which the execution performance result and the evaluation performance result of the relevant execution procedure are analyzed, and the variable parameter item and the search range thereof are identified from the starting point execution procedure, will be described below.

The variable parameter item identification unit 1504 identifies the execution parameter item 26d and the like, which can set the variable parameter item 26g for setting the search range of the variable parameter values in the starting point execution procedure, on the basis of the execution performance result and the evaluation performance result. The search range setting unit 1505 identifies the search range to be set by the variable parameter item 26g and thereby sets the range thereof, on the basis of the execution performance result and the evaluation performance result.

The setting of the variable parameter item 26g and the search range thereof may be set by the manager through the operation unit 10. In addition, the search range set for the variable parameter item 26g may be, for example: (i) a search range indicating a maximum variable estimation range in which a predetermined region range is further widened based on the range of a variable parameter value identified by the arithmetic processing unit 7 or the manager; or (ii) a search range indicating a minimum variable estimation range in which a predetermined region range that is considered promising (for example, a range identified from previous empirical measurement or knowledge of the manager, and the constraint condition) is further narrowed on the basis of the range of a variable parameter value identified by the arithmetic processing unit 7 or the manager. An example in which the search range of a variable parameter value is narrowed, on the basis of a patent publication, a publication of patent application, and the like, to an optimal range avoiding the contents of the patent publication, will be described in detail in a fourth embodiment that will be described below.

For example, in a case where optimization of the variable parameter value is performed while securing constant quality or the like in the actual production site, the search range setting unit 1505 may narrow the search range of the variable parameter item or narrow the search range to optimize an accumulated value of a set of evaluation performance results, by performing an inverse calculation from allowable variations in the quality or the like.

The template execution procedure output unit 1506 sets the search range determined by the search range setting unit 1505 for the starting point execution procedure, generates the template execution procedure on the basis of the starting point execution procedure, and outputs the template execution procedure. The constraint condition setting unit 1507 adds a new constraint condition to the constraint condition item 26e in the template execution procedure or corrects the constraint condition, as necessary.

(1-2-2) Case where there are No Execution Performance Result and Evaluation Performance Result of Same Execution Procedure as Starting Point Execution Procedure Here, in a case where when there are no execution performance result and evaluation performance result of the same execution procedure as the starting point execution procedure in the database 8, the execution performance result and the evaluation performance result of the relevant execution procedure are analyzed, and the variable parameter item or the search range thereof is identified in the starting point execution procedure, will be described below by using from FIG. 19 to FIG. 28.

FIG. 19 is a schematic view illustrating an example of the starting point execution procedure in which a culture-related process of adjusting the culture medium A, culturing cells by using the culture medium A, adjusting the culture medium B, culturing the cells cultured in the culture medium A by using the culture medium B, and producing the cells of desired conditions, and an evaluation process of executing marker gene expression evaluation for the obtained cells are specified.

In this case, for example, when terms such as "Adjustment of differentiation-inducing culture medium A", "Adjustment of differentiation-inducing culture medium B", "Culture using differentiation-inducing culture medium A", and "Culture using differentiation-inducing culture medium B", which identify the culture-related process that is wished to be optimized by the manager, are inputted through the operation unit 10, and terms such as "Marker gene expression evaluation" for identifying the evaluation process are inputted through the operation unit 10, the starting point execution procedure acquisition unit 1501 searches for the execution procedures of the same culture-related process and the same evaluation process from the database 8 on the basis of these terms, and acquires the starting point execution procedure.

Here, in order to simplify the description, a case is described in which an execution procedure including the same terms is searched from the database 8 on the basis of the terms inputted by the manager and is acquired as the starting point execution procedure; however, the invention is not limited to this. For example, in addition to the terms themselves, the starting point procedure may be acquired from the database 8 on the basis of the degree of similarity specified in advance between the following: the types represented by the terms (for example, an operation, an input, an output, and a constraint), the procedure of the operations, the usage sequence of the processing target before performing the operations, the appearance sequence of the outcomes obtainable by the operations, the structure of an intermediate representation (for example, an abstract syntax tree), and the like.

FIG. 19 illustrates an example of the configuration of the starting point execution procedure searched from the database 8. As shown in FIG. 19, in this starting point execution procedure, the contents related to the operations performed in the culture-related process and the evaluation process are specified for the operation outline fields C6, C7, C8, C9, and C10 for each operation. As with the above-described starting point execution procedure in FIG. 2, for example, the operation outline fields C6, C7, C8, C9, and C10 of this starting point execution procedure also include the operation item 26a in which the contents of the operations are specified, the input item 26b in which the processing targets of the operations are specified, the output item 26c in which the outcomes obtainable by the operations are specified, the execution parameter item 26d in which the numerical values relevant to the operations are specified, and the constraint condition item 26e in which the constraint conditions related to the operations are specified.

Next, the execution performance result/evaluation performance result acquisition unit 1502 searches whether the execution performance result and the evaluation performance result of the same execution procedure as the starting point execution procedure are recorded in the database 8, and in a case where the execution performance result and the evaluation performance result of the same execution procedure as the point execution procedure are not recorded in the database 8, the execution performance result and the evaluation performance result of an execution procedure (relevant execution procedure) relevant to the starting point execution procedure are acquired from the database 8.

In this case, for example, on the basis of terms such as "Adjustment of differentiation-inducing culture medium A", "Adjustment of differentiation-inducing culture medium B", "Culture using differentiation-inducing culture medium A", and "Culture using differentiation-inducing culture medium B" specified in the culture-related process in the starting point execution procedure, and terms such as "Marker gene expression evaluation" specified in the evaluation process, the execution performance result/evaluation performance result acquisition unit 1502 identifies an execution procedure in which these terms are included, from the execution procedures recorded in the database 8, uses the identified execution procedure as a relevant execution procedure, and acquires the execution performance result and the evaluation performance result of the relevant execution procedure from the database 8.

Here, FIG. 20 and FIG. 21 illustrate examples of the configuration of the execution performance result and the evaluation process of the relevant execution procedures. FIG. 22 illustrates the evaluation performance results of the relevant execution procedures (execution procedures A and Z) shown in these FIG. 20 and FIG. 21.

The relevant execution procedure (execution procedure A) shown in FIG. 20 does not include the operation outline field C8 of the "Adjustment of differentiation-inducing culture medium B" and the operation outline field C9 of the "Cell culture using differentiation-inducing culture medium B" of the starting point execution procedure shown in FIG. 19; however, the operation outline fields C6, C12, and C13 include the terms such as "Adjustment of differentiation-inducing culture medium A", "Cell culture using differentiation-inducing culture medium A", and "Marker gene expression evaluation" in the starting point execution procedure. As a result, the execution performance result/evaluation performance result acquisition unit 1502 acquires the evaluation performance results of the relevant execution procedure shown in FIG. 20 and the execution procedure A shown in FIG. 22 as the execution performance result and the evaluation performance result of the relevant execution procedures.

In addition, the relevant execution procedure (execution procedure B) shown in FIG. 21 includes all of the operation outline fields of the starting point execution procedure. That is, the operation outline fields C6, C12, C13, C14, and C15 include the terms such as "Adjustment of differentiation-inducing culture medium A", "Cell culture using differentiation-inducing culture medium A", "Adjustment of differentiation-inducing culture medium B", "Cell culture using differentiation-inducing culture medium B", and "Marker gene expression evaluation", which are the same terms as those of the starting point execution procedure. As a result, the execution performance result/evaluation performance result acquisition unit 1502 acquires the relevant execution procedure shown in FIG. 21 and the evaluation performance result of the execution procedure B shown in FIG. 22 as the execution performance result and the evaluation performance result of the relevant execution procedure.

The relevant execution procedure analysis unit 1503 compares the contents of the execution performance result shown in the operation outline field C6 of each culture-related process of the relevant execution procedures shown in these FIG. 20 and FIG. 21 with the contents of each evaluation performance result shown in FIG. 22, analyzes relevancy, dependency, and the like between the contents of the execution performance result (fluctuations in the numerical value of the execution parameter values, and the like) and the contents of the evaluation performance result obtained in the evaluation process, and estimates the execution parameter item of the culture-related process that affects the evaluation performance result.

In the relevant execution procedure analysis unit 1503 according to this embodiment, for example, since the "Marker gene expression positive rate", which is the evaluation performance result of the "Execution procedure B" shown in FIG. 22, is "82%", which is higher than the "Execution procedure A", a hypothesis that it is desirable to search for execution parameter values deriving a result close to the value of the "Marker gene expression positive rate" ("82%"), which is the evaluation performance result of the same "Execution procedure B", can be established.

The relevant execution procedure analysis unit 1503 analyzes, for example, the contents of the "Execution parameter values" of the execution procedures A and B, and obtains an analysis result that with regard to the "Basal culture medium concentration", "BMP4 concentration", and "Glucose concentration", the values of the "Execution procedure A" and the "Execution procedure B" are the same, and with regard to the "VEGF concentration", the value of the "Execution procedure A" is "10 µM", which is larger than "5 µM" of the "Execution procedure B".

As a result, the relevant execution procedure analysis unit 1503 obtains an analysis result that when the value of the "VEGF concentration" in the "Execution parameters" is made large, there is a possibility that cells close to the "Marker gene expression positive rate" obtained by the "Execution procedure B" may be produced. Here, only two evaluation performance results of the execution procedures A and Z are mentioned as examples; however, the variable parameter values may be determined by making a comparison of the execution parameter values of a large number of previously executed evaluation performance results, for example, several hundred evaluation performance results. At this time, in the relevant execution procedure analysis unit 1503, the execution parameter values of a plurality of procedures in which an evaluation execution result with the value of the "Marker gene expression positive rate" being a value close to "82%", for example, "77% to 87%" with a range of around "5%" is obtained, may be compared.

The relevant execution procedure analysis unit 1503 transmits such an analysis result to the variable parameter item identification unit 1504. The variable parameter item identification unit 1504 sets, as shown in FIG. 23, the "BMP4 concentration", the "VEGF concentration", and the "Glucose concentration" of the execution parameter item specified for the operation outline field C6 of the "Adjustment of differentiation-inducing culture medium A" of the starting point execution procedure, as a variable parameter item 26j, on the basis of the analysis result received from the relevant execution procedure analysis unit 1503 and the execution performance result and the evaluation performance result of the relevant execution procedure.

The variable parameter item identification unit 1504 estimates the search range of the variable parameter item 26j on the basis of the analysis result from the relevant execution procedure analysis unit 1503, the execution performance result and the evaluation performance result of the relevant execution procedure, and a starting point execution procedure in which the "BMP4 concentration", the "VEGF concentration", and the "Glucose concentration" of the operation outline field C6 are set as the variable parameter item 26j, and for example, "0 μM<BMP4 concentration <10 μM", "0 μM<VEGF concentration <15 μM", and "3 μM<Glucose concentration <15 μM" are set. Here, with regard to the "Basal culture medium concentration", a unique value is set not as the "variable parameter" but as the "execution parameter". As a result, the template execution procedure output unit 1506 outputs the template execution procedure shown in FIG. 23 on the basis of these pieces of information.

FIG. 24 and FIG. 25 illustrate examples of the configuration of the execution procedure generated on the basis of the template execution procedure shown in FIG. 23. In the arithmetic processing unit 7, when the variable parameter value setting unit 16 receives the template execution procedure shown in FIG. 23 from the template execution procedure generation unit 15, the variable parameter value setting processing is performed by the variable parameter value setting unit 16, a plurality of variable parameter values (in this example, the "BMP4 concentration" is "5 μM", "6 μM", or the like) in the search range of the variable parameter item 26j, and a list of a plurality of execution procedures in which each variable parameter value is set is generated by the execution procedure generation unit 17.

Figure 26:
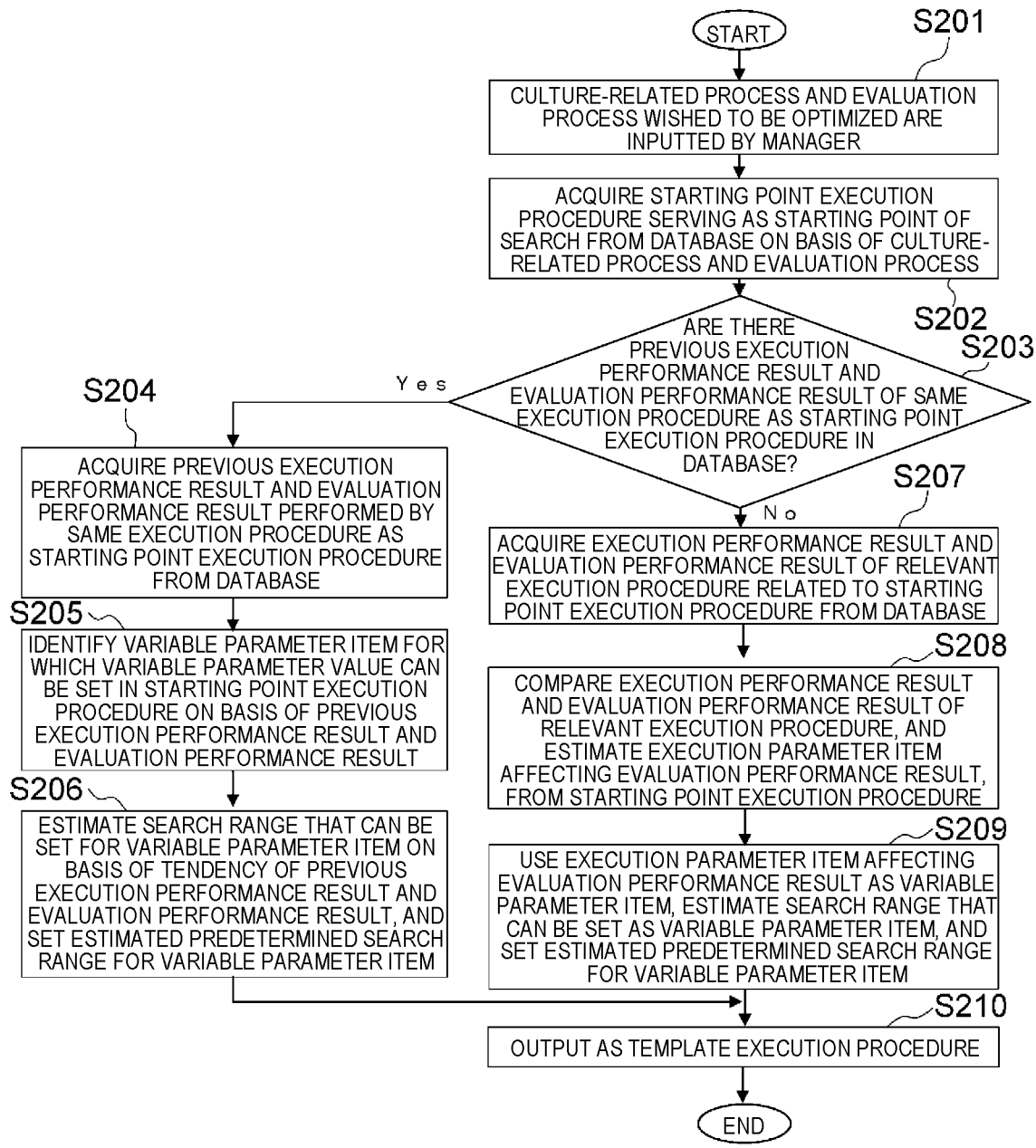
FIG. 26 is a flow chart illustrating a template execution procedure generation processing procedure.

(1-2-3) Flowchart of Template Execution Procedure Generation Processing Procedure Next, the above-mentioned template execution procedure generation processing will be described below by using the flowchart in FIG. 26. As shown in FIG. 26, the culture-related process optimization device 2 starts the template execution procedure generation processing procedure from a start step, and in a next step S201, the culture-related process and evaluation process that are wished to be optimized are inputted by the manager.

In a next step S202, the template execution procedure generation unit 15 acquires the starting point execution procedure that serves as a starting point of search, from the database 8 on the basis of the culture-related process and the evaluation process.

Here, in order to simplify the description, a case in which the database 8 is searched to acquire the starting point execution procedure serving as the starting point of search, has been described; however, the invention is not limited to this. For example, in a case where even though the database 8 is searched, a starting point execution procedure that serves as the starting point of search is not present and cannot be acquired from the database 8, a starting point execution procedure may be newly created in the template execution procedure generation unit 15, and the starting point execution procedure may be acquired. Regarding the creation of a new starting point execution procedure, the manager himself/herself may create and acquire a new starting point execution procedure through the operation unit 10, or the template execution procedure generation unit 15 may automatically create and acquire an approximate starting point execution procedure on the model of the operations of a predetermined culture-related process and a predetermined evaluation process, from a tendency of operation names, used device names, or the like inputted by the manager.

In a next step S203, the template execution procedure generation unit 15 decides whether there are previous execution performance results and evaluation performance results of the same execution procedure as the starting point execution procedure in the database 8. Here, when it is decided that the execution performance result and the evaluation performance result of the same execution procedure as the starting point execution procedure are present in the database 8 (Yes), in a next step S204, the template execution procedure generation unit 15 acquires the execution performance result and the evaluation performance result of the same execution procedure as the starting point execution procedure from the database 8.

In a next step S205, the template execution procedure generation unit 15 identifies the variable parameter item for which the variable parameter values can be set in the starting point execution procedure on the basis of the previous execution performance result and evaluation performance result acquired in the step S204.

With regard to the setting of such a variable parameter item, the manager may closely examine the item from the starting point execution procedure and set a predetermined item as the variable parameter item on the basis of the input of a selection command by the manager through the operation unit 10.

In a next step S206, the template execution procedure generation unit 15 estimates a search range that can be set for the variable parameter item on the basis of the previous execution performance results and evaluation performance result acquired in the step S204, and sets the estimated predetermined search range for the variable parameter item. In a next step S210, the template execution procedure generation unit 15 outputs the template execution procedure in which the search range is set for the variable parameter item, and ends the above-mentioned template execution procedure generation processing procedure.

With regard to such setting of the search range for the variable parameter item, the manager may closely examine the range of the variable parameter value and set the search range on the basis of the input of the input command by the manage through the operation unit 10.

On the other hand, when it is decided in the above-mentioned step S203 that there are no execution performance result and evaluation performance result of the same execution procedure as the starting point execution procedure (No), the template execution procedure generation unit 15 acquires, in a next step S207, the execution performance result and the evaluation performance result of a relevant execution procedure relevant to the starting point execution procedure from the database 8, on the basis of the inputted culture-related process and evaluation process.

In a next step S208, the template execution procedure generation unit 15 compares the execution performance results and evaluation performance results of a plurality of relevant execution procedures and estimates the execution parameter items affecting the evaluation performance result from the starting point execution procedure.

In a next step S209, the template execution procedure generation unit 15 uses the execution parameter item that affects the evaluation performance result as a variable parameter item, and estimates the search range that can be set for this variable parameter item on the basis of the execution performance results and the evaluation performance results of the relevant execution procedures. Then, the template execution procedure generation unit 15 sets the estimated predetermined search range for the variable parameter item. In a next step S210, the template execution procedure generation unit 15 outputs the template execution procedure in which the search range is set for the variable parameter item, and ends the above-mentioned template execution procedure generation processing procedure.

(1-3) Variable Parameter Value Setting Processing

Figure 27:
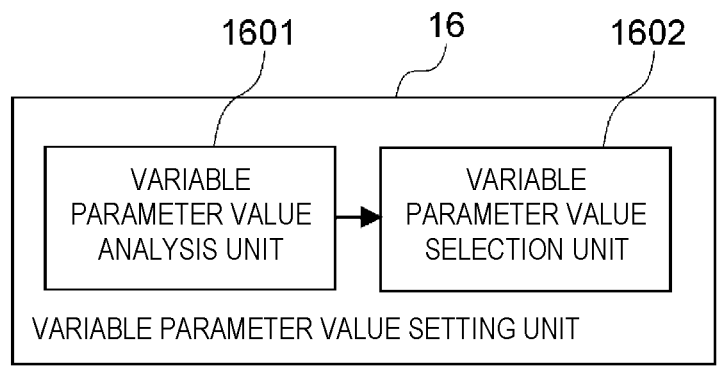
FIG. 27 is a block diagram illustrating a configuration of a variable parameter value setting unit.

Next, the above-mentioned variable parameter value setting processing procedure will be described. FIG. 27 is a block diagram illustrating the configuration of the variable parameter value setting unit 16. As shown in FIG. 27, the variable parameter value setting unit 16 includes a variable parameter value analysis unit 1601 and a variable parameter value selection unit 1602. The variable parameter value analysis unit 1601 acquires, for example, an execution performance result and an evaluation performance result identical or relevant to the starting point execution procedure from the database 8, and analyzes a variable parameter value that affects the evaluation performance result from within the search range by a regression model or the like using these execution performance result and evaluation performance result.

As the regression model, for example, principal component analysis (PCA) in which an execution parameter value of the execution performance result at a part corresponding to the variable parameter item for which the search range is set by the template execution procedure, as an explanatory variable, and the evaluation performance is set as an objective variable; partial least squares (PLS) in which an execution parameter value of the execution performance result and the evaluation performance result at a part corresponding to the variable parameter item for which the search range is set by the template execution procedure, are set as explanatory variables, and the evaluation performance result is set as an objective variable; and various regression models that apply linear or nonlinear transformation, such as polynomial regression, Gaussian process regression, and random forest regression, can be applied. In addition, as the regression model, for example, a machine learning model in which an execution performance result and an evaluation performance result are generated by machine learning, may also be applied.

As the machine learning model, for example, a neural network defined as a type of combining at least one matrix operation and at least one linear or nonlinear transformation can be applied. When the machine learning model is learned, supervised learning and unsupervised learning are available. When an unlearned machine learning model is subjected to supervised learning, an execution performance result, an evaluation performance result thereof, and a truth label indicating whether the evaluation performance result is a desired result (for example, an accuracy indicating whether the evaluation performance result is a desired evaluation performance result) are used, and when the execution performance result and the evaluation performance result are learned, the machine learning model is subjected to learning by applying the truth label.

When an unlearned machine learning model is subjected to unsupervised learning, an execution performance result and an evaluation performance result thereof are used, and the regularity or characteristics of the execution performance result and the evaluation performance result are learned.

The variable parameter value setting unit 16 acquires a prediction result (for example, an accuracy in the case of supervised learning, or a predicted evaluation result in the case of unsupervised learning) by inputting an arbitrarily selected variable parameter value to a learned machine learning model in the variable parameter value analysis unit 1601, and selects the variable parameter value on the basis of the prediction result in the variable parameter value selection unit 1602.

In such a regression model, it is desirable to add the execution result and the evaluation result received from the execution environment 100 each time as an explanatory variable, an objective variable, learning data, or the like. As a result, a regression model reflecting the latest data of the execution procedure executed in the execution environment 100 can be generated, and optimization of the culture-related process can be further promoted.

The variable parameter value selection unit 1602 selects a predetermined number of variable parameter values from within the search range of the variable parameter item, for example, according to Bayesian optimization, an orthogonal table, a Latin hypercube method, or the like, on the basis of the analysis result of the variable parameter value analysis unit 1601.

Specifically, for example, the variable parameter value selection unit 1602 selects the variable parameter values by using the regression model generated by the variable parameter value analysis unit 1601 on the basis of previous execution performance results and evaluation performance results. As a method for selecting the variable parameter values by using a regression model, the variable parameter values may be algorithmically selected by defining certain functions on the search space on the basis of the regression model, and optimizing the functions, and in addition, some or all of the variable parameter values generated as described above may be substituted under the decision of the manager.

The functions defined on the search space on the basis of the regression model are, for example, functions (for example, upper confidence bound, expected improvement, parallel knowledge gradient, and mutual information) that quantitatively define how much improvement of the evaluation result or how much information is newly obtained when the variable parameter values are generated at which point of the search space, and by performing optimization (for example, maximization, minimization, or weighted sampling) of a given procedure in relation to these functions, a list of the predetermined number of variable parameter values can be obtained.

In a case where there are a plurality of variable parameter values, when it is necessary to allocate a priority order to those variable parameter values, the priority order can be algorithmically determined by a given criterion that is suitably determined (for example, in addition to sorting based on the values of the functions, in a case where the variable parameter values are sequentially generated by a method such as local penalization, the priority order is allocated to a generation order of the variable parameter values in an ascending order), the priority order may be allocated arbitrarily by the decision of the manager.

The variable parameter value setting unit 16 may have a function of transforming or limiting the search range by reflecting an attribute value of a variable parameter value (for example, in the case of a substance concentration in a solution, a flow rate, or the like, it is more effective when the variable parameter value is multiplied by log, such that the change of the objective variable becomes even with respect to the change of the explanatory variable, and the contribution is easily noticeable, and therefore, for example, a value obtained by multiplying the variable parameter value by log), and may estimate the variable parameter values from within the transformed or limited search range. For example, in a case where it has been found that a certain variable parameter value is of a type that is logarithmically changed with respect to the evaluation value, the cases of also correspondingly subjecting the variable parameter values to logarithmic transformation, are included.

In addition, for example, in a case where optimization is performed while securing constant quality and the like in the actual production site, the variable parameter value setting unit 16 may narrow the variable parameter value from within the search range by performing inverse calculation from the allowable variation of the quality and the like, or may select the variable parameter values for optimizing the accumulated values of a set of evaluation performance results from the search range.

Figure 28:
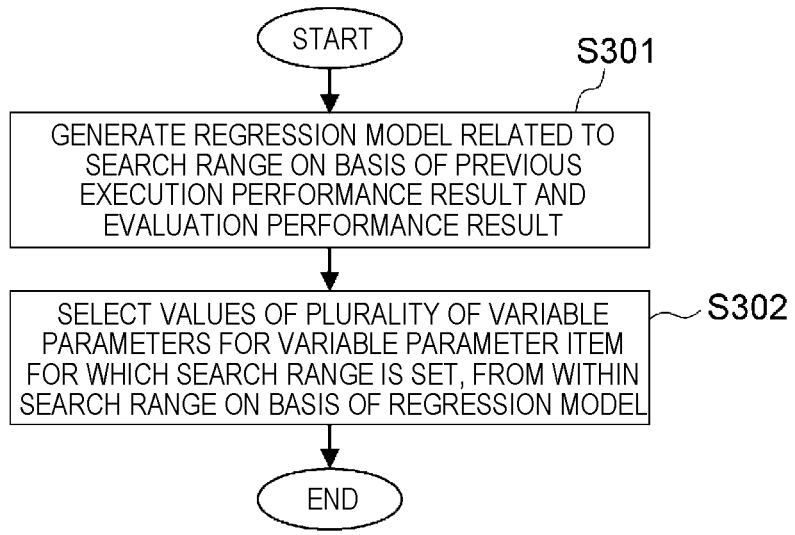
FIG. 28 is a flow chart illustrating a variable parameter value setting processing procedure.

For example, when the above-mentioned variable parameter value setting processing is described by using the flowchart in FIG. 28, the variable parameter value setting unit 16 starts the variable parameter value setting processing procedure from a start step and generates, in a next step S301, for example, a regression model related to the search range on the basis of previous execution performance results and evaluation performance results.

In a next step S302, the variable parameter value setting unit 16 selects a plurality of variable parameter values from within the search range on the basis of a regression model for the variable parameter item for which the search range is set, and ends the variable parameter value setting processing procedure.

Figure 29:
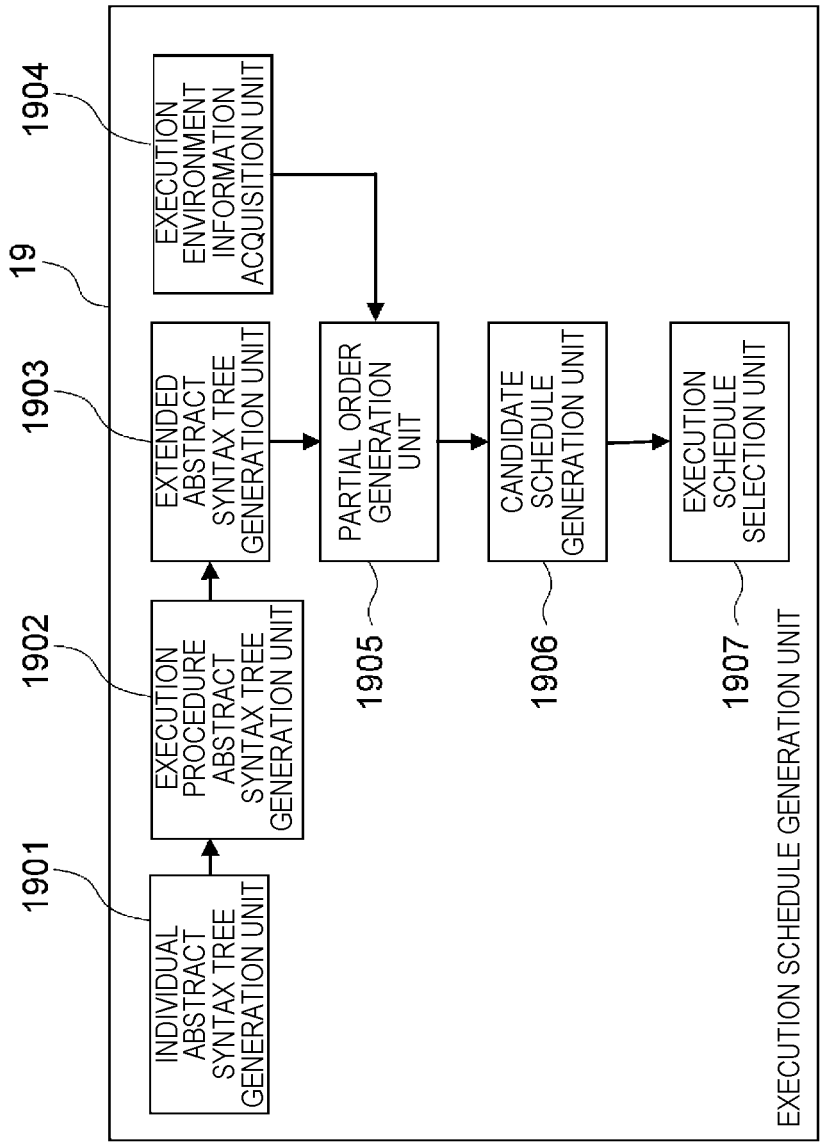
FIG. 29 is a block diagram illustrating a configuration of an execution schedule generation unit.
Figure 30:
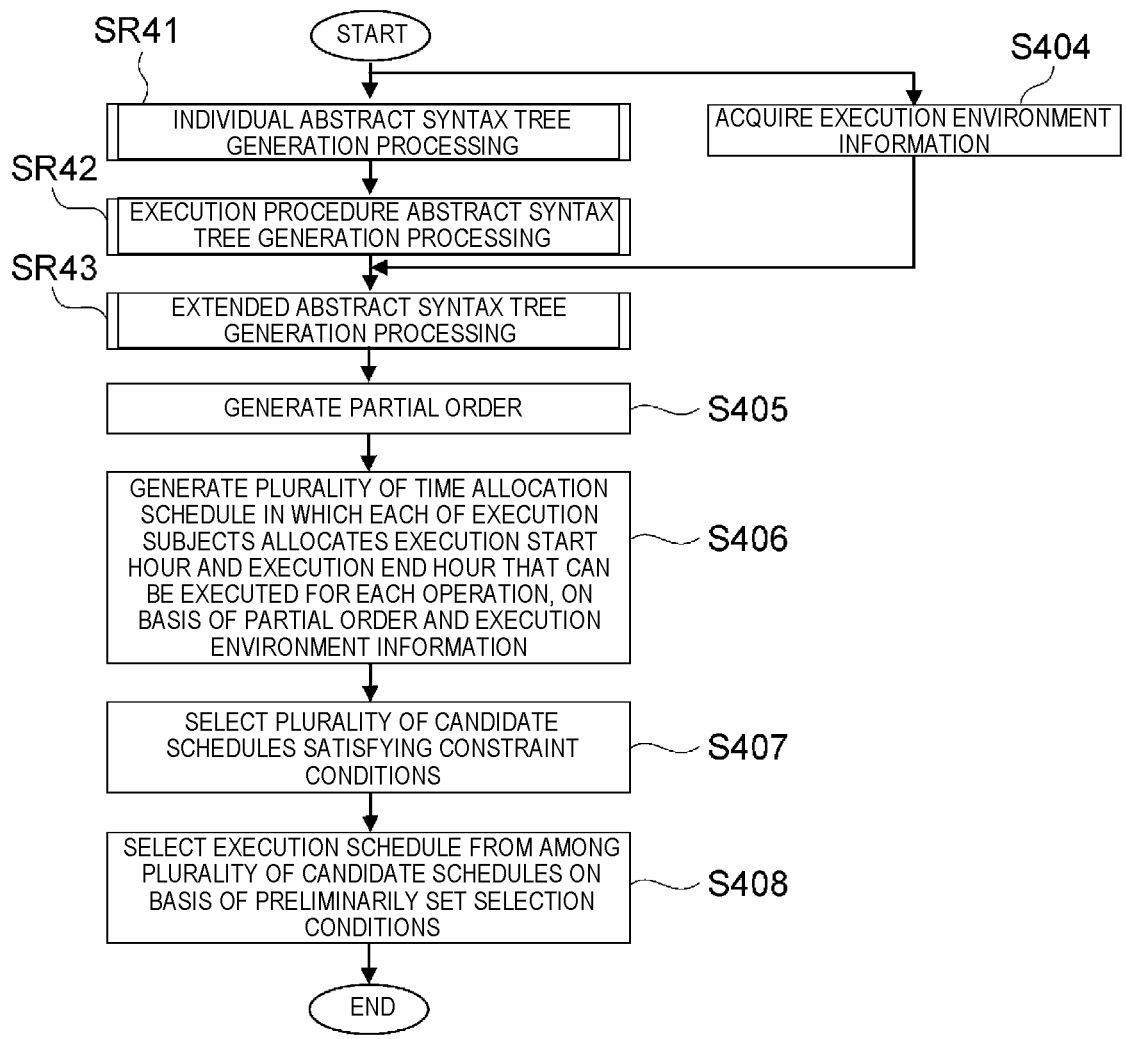
FIG. 30 is a flow chart illustrating an execution schedule generation processing procedure.

(1-4) Execution Schedule Generation Processing (1-4-1) Outline of Execution Schedule Generation Processing Next, the above-mentioned execution schedule generation processing procedure will be described. FIG. 29 is a block diagram illustrating the configuration of the execution schedule generation unit 19. FIG. 30 is a flowchart illustrating the execution schedule generation processing procedure. Here, an example of generating an execution schedule of the execution procedure shown in FIG. 6 will be described below.

As shown in FIG. 29, the execution schedule generation unit 19 includes an individual abstract syntax tree generation unit 1901, an execution procedure abstract syntax tree generation unit 1902, an extended abstract syntax tree generation unit 1903, an execution environment information acquisition unit 1904, a partial order generation unit 1905, a candidate schedule generation unit 1906, and an execution schedule selection unit 1907.

In this case, the execution schedule generation unit 19 starts an execution schedule generation processing procedure from the start step as shown in FIG. 30 and proceeds to a next subroutine SR41 and a step S404. In the subroutine SR41, the execution schedule generation unit 19 allows the individual abstract syntax tree generation unit 1901 to perform individual abstract syntax tree generation processing (will be described below), and generates individual abstract syntax trees for the operations specified in the operation outline fields C1, C2, C3, C4, and C5, respectively, in the execution procedure as shown in FIG. 6.

Figure 31:
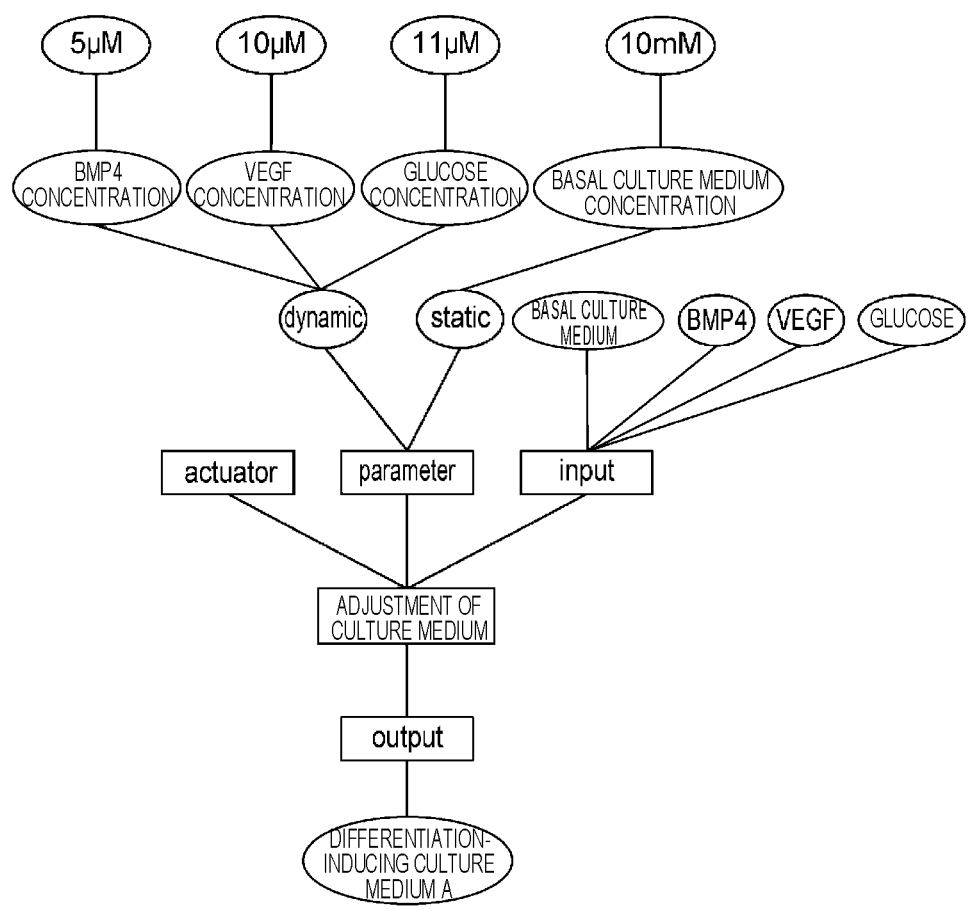
FIG. 31 is a schematic view illustrating an example of a configuration (1) of an individual abstract syntax tree.
Figure 32:
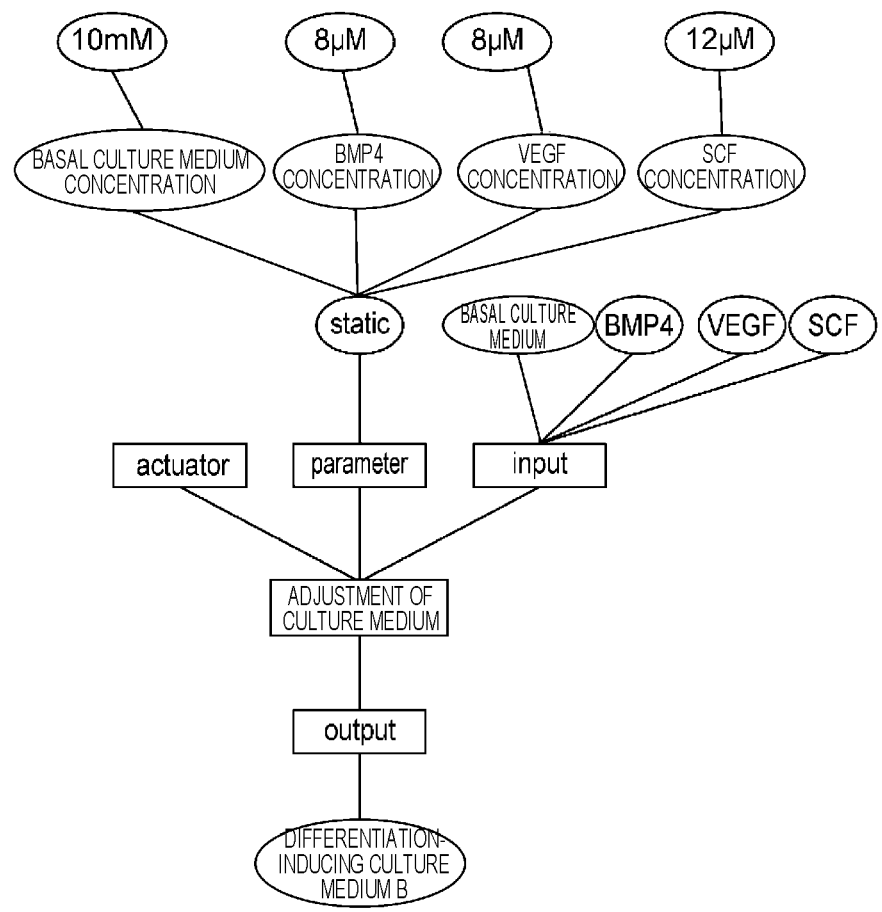
FIG. 32 is a schematic view illustrating an example of a configuration (2) of the individual abstract syntax tree.

Here, FIG. 31 illustrates the configuration of an individual abstract syntax tree generated from the operation outline field C1 of the "Adjustment of differentiation-inducing culture medium A" of the execution procedure shown in FIG. 6 by the individual abstract syntax tree generation processing. FIG. 32 illustrates the configuration of an individual abstract syntax tree generated from the operation outline field C2 of the "Cell culture using differentiation-inducing culture medium A" of the execution procedure shown in FIG. 6.

Figure 33:
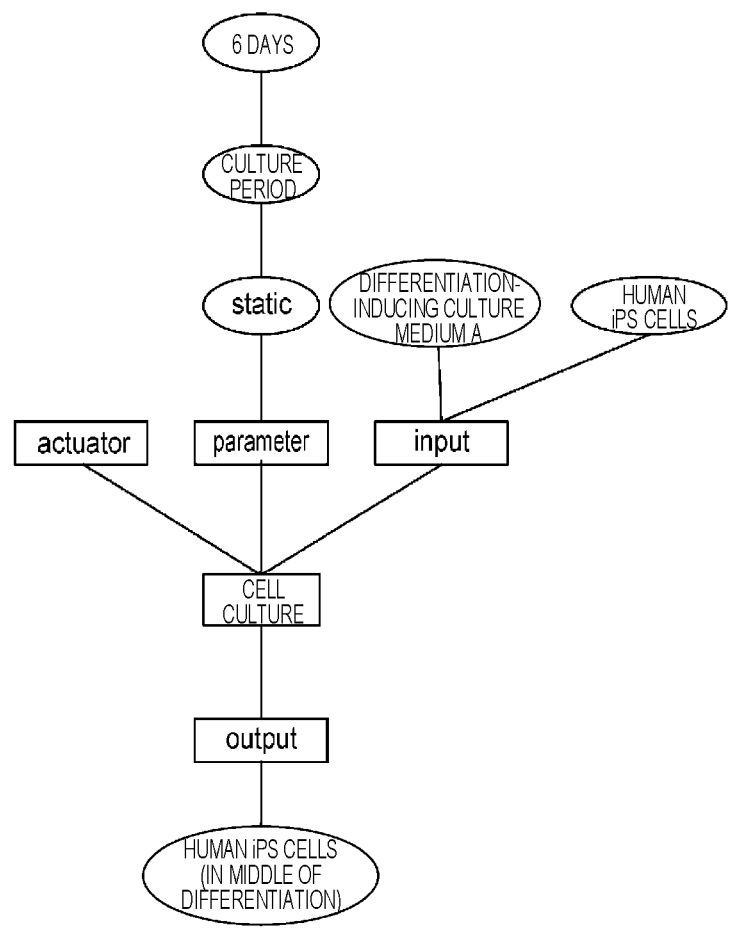
FIG. 33 is a schematic view illustrating an example of a configuration (3) of the individual abstract syntax tree.
Figure 34:
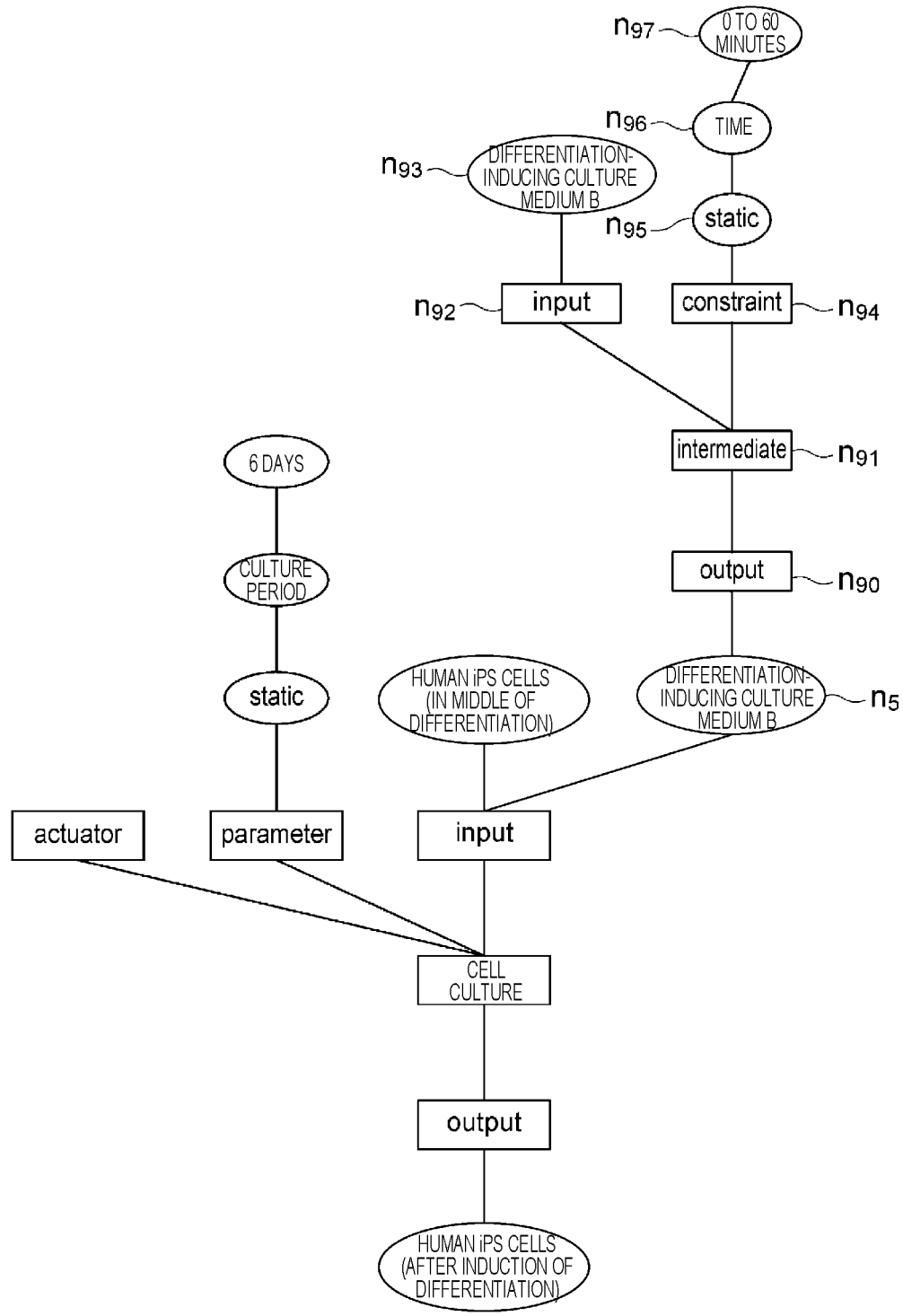
FIG. 34 is a schematic view illustrating an example of a configuration (4) of the individual abstract syntax tree.

FIG. 33 illustrates the configuration of an individual abstract syntax tree generated from the operation outline field C3 of the "Adjustment of differentiation-inducing culture medium B" of the execution procedure shown in FIG. 6 by the individual abstract syntax tree generation processing. FIG. 34 illustrates the configuration of an individual abstract syntax tree generated from the operation outline field C4 of the "Cell culture using differentiation-inducing culture medium B" of the execution procedure shown in FIG. 6.

On the other hand, in a step S404, the execution schedule generation unit 19 allows the execution environment information acquisition unit 1904 to acquire execution environment information E shown in FIG. 10A, for example, from the database 8 or the execution environment 100.

In a subroutine SR42, the execution schedule generation unit 19 allows the execution procedure abstract syntax tree generation unit 1902 to perform execution procedure abstract syntax tree generation processing (will be described below), integrate a plurality of individual abstract syntax trees generated in the above-described subroutine SR41, and generate an execution procedure abstract syntax tree t shown in FIG. 8, FIG. 9A, and FIG. 9B. It is noted that when there is only one individual abstract syntax tree, this individual abstract syntax tree is handled as the execution procedure abstract syntax tree.

In a next subroutine SR43, the execution schedule generation unit 19 allows the extended abstract syntax tree generation unit 1903 to perform extended abstract syntax tree generation processing (will be described below), reflects the contents of the execution environment information E shown in FIG. 10A to the execution procedure abstract syntax tree t shown in FIG. 8, FIG. 9A, and FIG. 9B, and generates an extended abstract syntax tree t' shown in FIG. 12, FIG. 13, and FIG. 14.

In a next step S405, the execution schedule generation unit 19 allows the partial order generation unit 1905 to generate a partial order shown in FIG. 10B from the extended abstract syntax tree t'. In a next step S406, the execution schedule generation unit 19 allows the candidate schedule generation unit 1906 to determine a start hour (for example, set as 8:30 on Jan. 2, 2020) for starting the execution procedure, and generate a set A" (FIG. 15) of a plurality of time allocation schedules, in which an execution start hour and an execution end hour, at which each of the execution subjects can execute the execution, are allocated for each operation according to the sequence for executing the operations, on the basis of the partial order and the execution environment information E.

Furthermore, the execution schedule generation unit 19 allows the candidate schedule generation unit 1906 to select a candidate schedule that satisfies the constraint condition specified in the execution procedure or the like from among the plurality of time allocation schedules, and generate a set A''' (FIG. 16) of the candidate schedules.

In a next step S408, the execution schedule generation unit 19 allows the execution schedule selection unit 1907 to select an execution schedule from among a plurality of candidate schedules, for example, on the basis of a selection condition set in advance, such as "Select a candidate schedule with earliest execution end time of "Marker gene expression evaluation", which is final operation of execution procedure", and end the execution schedule generation processing procedure.

(1-4-2) Individual Abstract Syntax Tree Generation Processing

Figure 35:
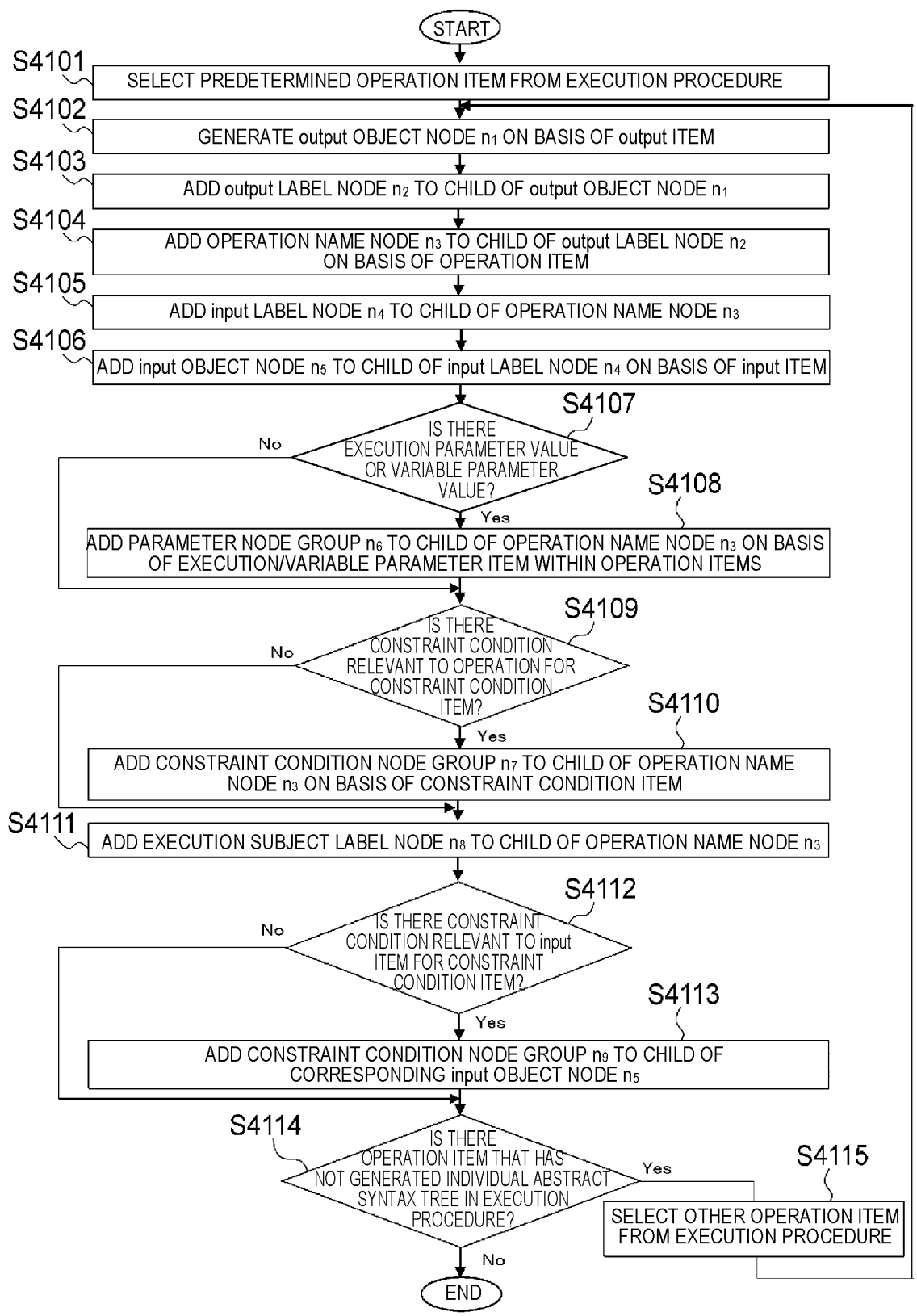
FIG. 35 is a flow chart illustrating an individual abstract syntax tree generation processing procedure.

Next, the above-mentioned individual abstract syntax tree generation processing will be described. FIG. 35 is a flowchart illustrating an example of the individual abstract syntax tree generation processing procedure. Here, an example of generating the individual abstract syntax tree shown in FIG. 39 on the basis of the operation outline field C2 of the "Cell culture using differentiation-induced culture medium A" of the execution procedure 1 shown in FIG. 6, will be described.

As shown in FIG. 35, the individual abstract syntax tree generation unit 1901 starts the individual abstract syntax tree generation processing procedure from a start step, and selects, in a next step S4101, for example, an operation item 26a of the operation outline field C2 for generating an individual abstract syntax tree from the execution procedure.

Figure 36:
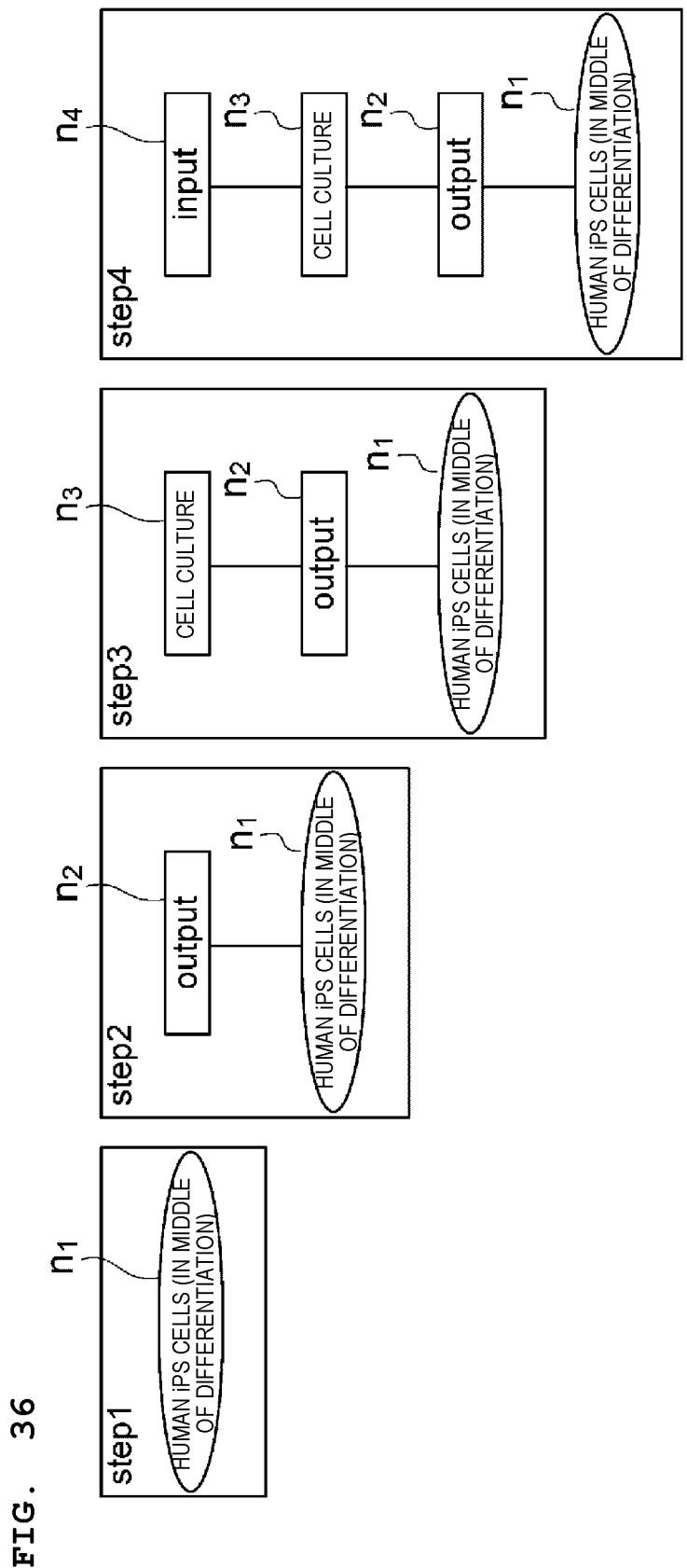
FIG. 36 is a schematic view for describing an outline (1) of the individual abstract syntax tree generation processing procedure.

In a next step S4102, the individual abstract syntax tree generation unit 1901 generates, on the basis of an output item 26c of the operation outline field C2, an output object node $n_1$ indicating the contents of the output item 26c (here, "Human iPS cells (in middle of differentiation)") as shown in "step 1" of FIG. 36. In a next step S4103, the individual abstract syntax tree generation unit 1901 adds an output label node $n_2$ indicating "output" to a child of the output object node $n_1$ through an edge, as shown in "step 2" of FIG. 36.

In a next step S4104, the individual abstract syntax tree generation unit 1901 adds, on the basis of the operation item 26a of the operation outline field C2, an operation name node $n_3$ indicating the operation contents of the operation item 26a (here, the operation is "Cell culture using differentiation-inducing culture medium A" indicating the operation contents and is represented simply as "Cell culture"), to a child of the output label node $n_2$ through an edge, as shown in "step 3" of FIG. 36. In a next step S4105, the individual abstract syntax tree generation unit 1901 adds an input label node nq indicating "input" to a child of the operation name node $n_3$ through an edge, as shown in "step 4" of FIG. 36.

Figure 37:
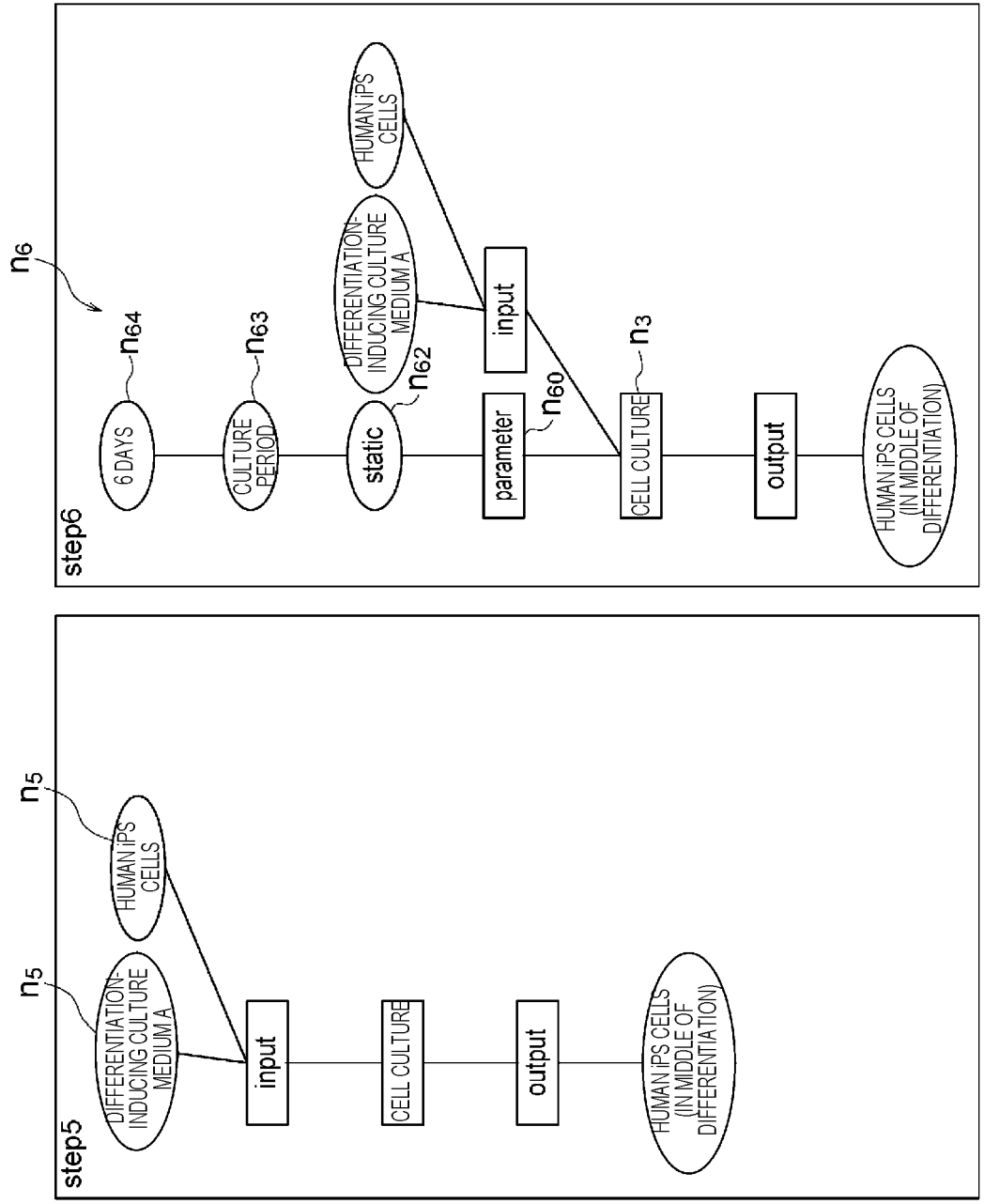
FIG. 37 is a schematic view for describing an outline (2) of the individual abstract syntax tree generation processing procedure.

In a next step S4106, the individual abstract syntax tree generation unit 1901 adds an input object node $n_5$ indicating the contents of the input item 26b (herein, "Differentiation-inducing culture medium A" and "Human iPS cells") through an edge, as shown in "step 5" of FIG. 37, on the basis of the input item 26b of the operation outline field C2.

In a next step S4107, the individual abstract syntax tree generation unit 1901 decides whether there is the execution parameter value or the variable parameter value in the operation outline field C2. Here, in the operation outline field C2 of the execution procedure shown in FIG. 6, there is an execution parameter value for the execution parameter item 26d (also for the variable parameter item 26g), and since an affirmative result (Yes) is obtained in the step S4107, the individual abstract syntax tree generation unit 1901 proceeds to a next step S4108.

In the step S4108, the individual abstract syntax tree generation unit 1901 adds a parameter node group $n_6$ indicating the contents of the execution parameter item 26d (in a case where there is the variable parameter item 26g, the variable parameter item 26g) to a child of the operation name node $n_3$ through an edge, as shown in "step 6" of FIG. 37.

The parameter node group ne has a parameter label node $n_{60}$ indicating a node of a parameter, and a static label node $n_{62}$ indicating an execution parameter value that is added to a child of the parameter label node $n_{60}$ through an edge. In a case where there is a variable parameter value, a dynamic label node is added by a method similar to that of the parameter label node $n_{60}$.

To the static label node $n_{62}$ indicating an execution parameter value, each of the execution parameter values (herein, "Culture period") is added as a child through an edge, and a parameter value node $n_{64}$ indicating the numerical value of the execution parameter value (herein, "6 days") is added to the child of the parameter name node $n_{63}$ through an edge. Even in a case where there is the variable parameter value, in the same manner as described above, a parameter name node indicating a parameter name that is specified by the variable parameter value is added to the dynamic label node indicating a variable parameter value as a child through an edge, and a parameter value node indicating the numerical value of the variable parameter value is added to the child of the parameter name node through an edge.

When it is decided that there is no execution parameter value or variable parameter value in the above-described step S4107, the individual abstract syntax tree generation unit 1901 proceeds to a next step S4109.

In the step S4109, the individual abstract syntax tree generation unit 1901 decides whether there is a constraint condition related to an operation, for the constraint condition item 26e of the operation outline field C3, and proceeds to a next step S4110 in a case where there is the constraint condition. It is noted that whether the constraint condition specified for the constraint condition item 26e is a constraint condition directly related to an operation, a constraint condition related to the input item 26b, a constraint condition related to the output item 26c, or a constraint condition related to the execution parameter item 26d or the variable parameter item 26g, is determined when the execution procedure is generated. For the constraint condition item 26e of the operation outline field C2 described here, there is a constraint condition related to the input item 26b (herein, "Within 60 minutes after adjustment of differentiation-inducing culture medium A is finished"); however, there is no constraint condition related to an operation (for example, "Cell culture (operation of operation outline field C2) is within 10 days" or the like).

As described above, since there is no constraint condition related to an operation for the operation outline field C2, it is not shown in the diagram. In a case where there is a constraint condition related to an operation, in a step S4110, the individual abstract syntax tree generation unit 1901 adds a constraint condition node group $n_7$ (not shown in the diagram) indicating the contents of the constraint condition related to the operation to a child of the operation name node $n_3$, on the basis of the constraint condition item 26e.

In this case, in the constraint condition node group $n_7$ related to the operation, a constraint label node $n_{70}$ indicating the contents of the constraint condition related to the operation is added to the child of the operation name node $n_3$ through an edge, and in a case where the constraint condition is static (a fixed condition without fluctuations), a static label node nm (not shown in the diagram) is added to a child of the constraint label node no (not shown in the diagram) through an edge. In addition, as a child of this static label node nm, a constraint name node $n_{72}$ (not shown in the diagram) indicating a target name to be constrained is added through an edge, and as a child of this constraint name node $n_{72}$, a parameter value node $n_{73}$ (not shown in the diagram) indicating a parameter value to be constrained is added through an edge. In a case where the constraint condition is dynamic, a dynamic label node is added by a procedure similar to the above-described procedure.

Figure 38:
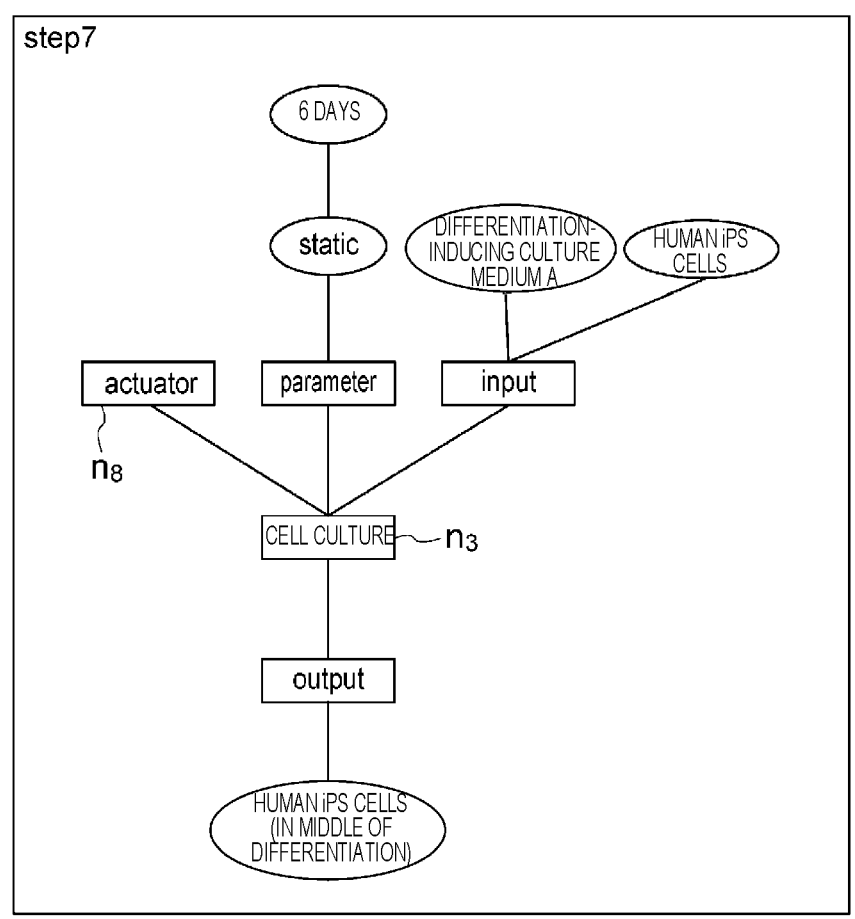
FIG. 38 is a schematic view for describing an outline (3) of the individual abstract syntax tree generation processing procedure.

On the other hand, when it is decided that there is no constraint condition related to the operation in the above-described step S4109, the individual abstract syntax tree generation unit 1901 proceeds to a next step S4111. In the step S4111, the individual abstract syntax tree generation unit 1901 adds an actuator label node $n_8$ indicating an execution subject of the operation to a child of the operation name node $n_3$ through an edge, as shown in "step 7" of FIG. 38.

In a next step S4112, the individual abstract syntax tree generation unit 1901 decides whether there is a constraint condition related to the input item 26b for the constraint condition item 26e of the operation outline field C3, and proceeds to a next step S4113 in a case where there is a constraint condition.

Figure 39:
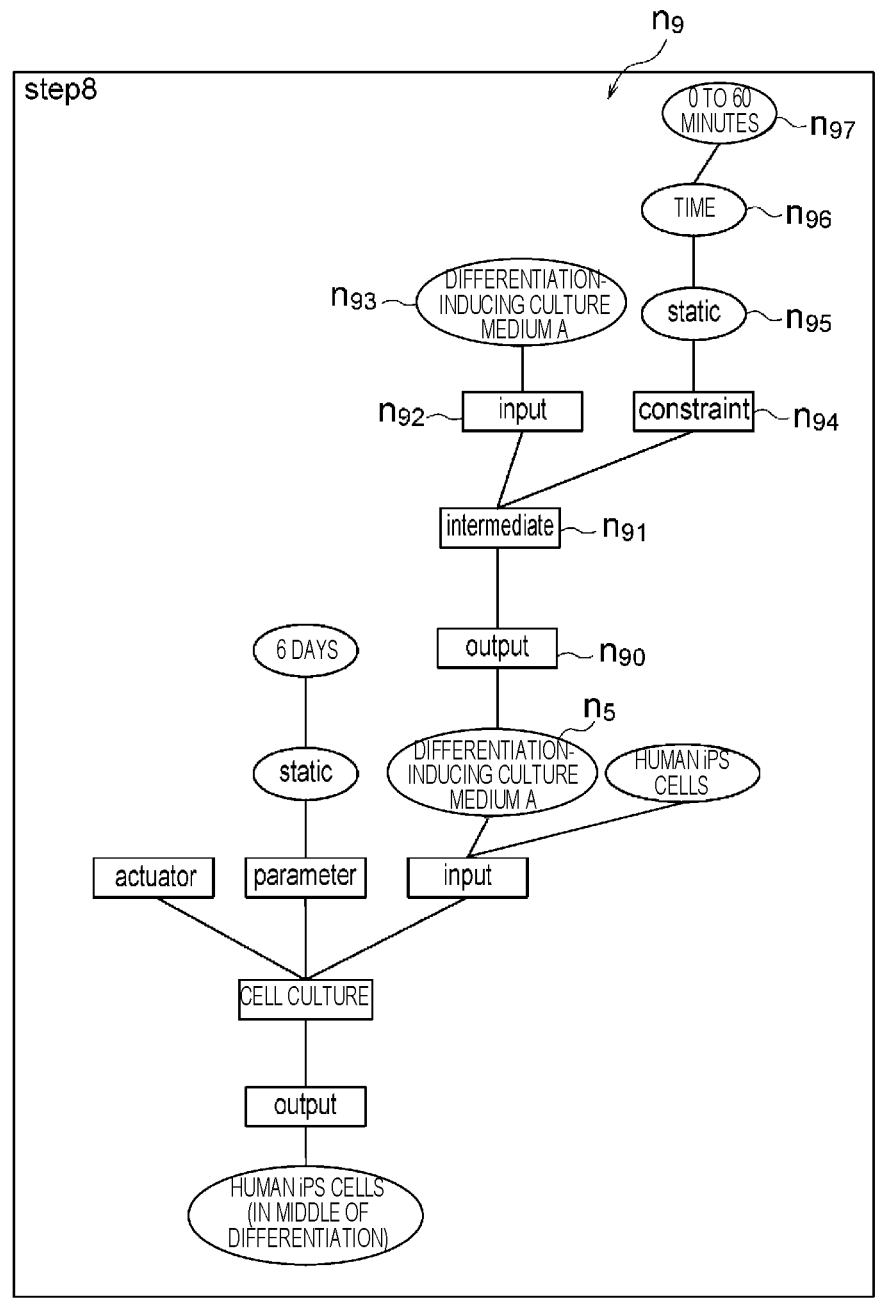
FIG. 39 is a schematic view for describing an outline (4) of the individual abstract syntax tree generation processing procedure.

In the step S4113, the individual abstract syntax tree generation unit 1901 adds a constraint condition node group $n_9$ indicating the contents of the constraint condition related to the input item 26b to a child of the corresponding input object node $n_5$, on the basis of the constraint condition item 26e as shown in "step 8" of FIG. 39.

Here, in the constraint condition node group $n_9$, an output label node $n_{90}$ is added to a child of the corresponding input object node $n_5$ through an edge, and an intermediate label node $n_{91}$ is added to a child of the output label node $n_{90}$. In addition, in the constraint condition node group $n_9$, an input label node $n_{92}$ is added to a child of the intermediate label node $n_{91}$ through an edge, and to a child of this input label node $n_{92}$, an input object node $n_{93}$ indicating an input target to be a decision criterion for operation start/end specified by the constraint condition (in this case, since a constraint condition for operation start of "Within 60 minutes after adjustment of differentiation-inducing culture medium A is finished" is specified, here, the "Differentiation-inducing culture medium A" is a decision criterion for the operation start specified by the constraint condition) is added through an edge.

Furthermore, in the constraint condition node group ng, a constraint label node $n_{94}$ indicating the contents of the constraint condition related to the input item 26b is added to a child of the intermediate label node $n_{91}$ through an edge, and to a child of this constraint label node $n_{94}$, a static label node $n_{95}$ indicating that the constraint condition is static (a fixed condition without fluctuations), a constraint name node $n_{96}$ indicating the target name to be constrained (here, "Time"), and a parameter value node $n_{97}$ indicating the parameter value to be constrained (here, "0 minutes to 60 minutes") are added in series through edges.

When it is decided that there is no constraint condition related to the input item 26b in the above-described step S4112, the individual abstract syntax tree generation unit 1901 proceeds to a next step S4114.

As described above, the individual abstract syntax tree generation unit 1901 can generate, for example, an individual abstract syntax tree for the operation outline field C2 of the execution procedure.

In the step S4114, the individual abstract syntax tree generation unit 1901 decides whether there is the operation item 26a for which an individual abstract syntax tree is not generated, in the execution procedure. Here, in a case where it is decided that the operation item 26a for which the individual abstract syntax tree is not generated is present in the execution procedure (Yes), in a next step S4115, the individual abstract syntax tree generation unit 1901 selects the operation items 26a of other operation outline fields C1, C3, C4, and C5 for which the individual abstract syntax tree is not generated, from the execution procedure, returns again to the above-mentioned step S4102, and repeats the above-mentioned processing until a negative result (No) is obtained in the step S4114.

On the other hand, in the step S4114, when it is decided that the operation item 26a for which the individual abstract syntax tree is not generated is not present in the execution procedure (No), this indicates that individual abstract syntax trees are generated for the operation items 26a of all the operation outline fields C1, C2, C3, C4, and C5 in the execution procedure, and the individual abstract syntax tree generation unit 1901 ends the above-mentioned individual abstract syntax tree generation processing procedure.

(1-4-3) Execution Procedure Abstract Syntax Tree Generation Processing

Figure 40:
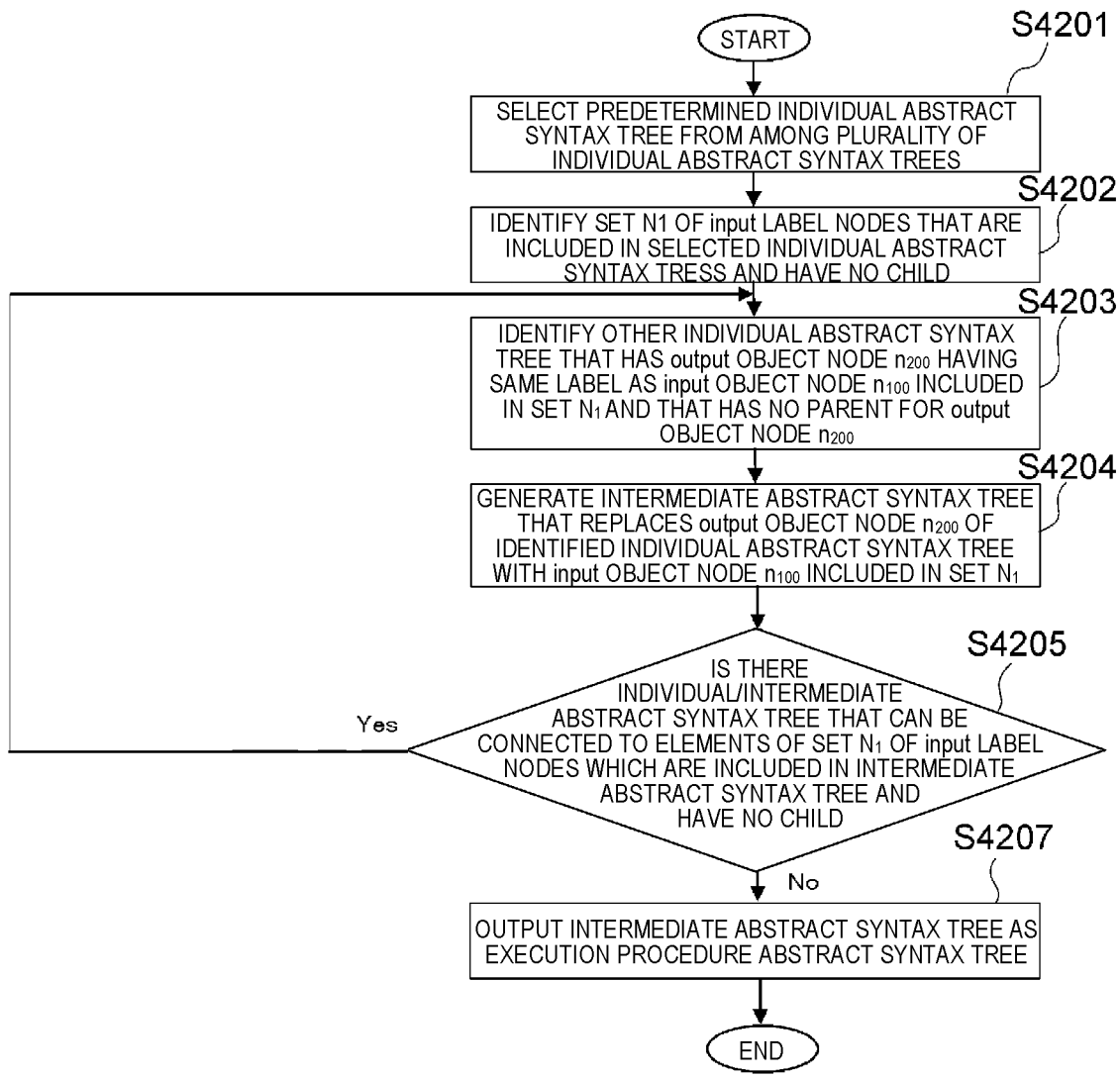
FIG. 40 is a flow chart illustrating an execution procedure abstract syntax tree generation processing procedure.

Next, the above-mentioned execution procedure abstract syntax tree generation processing for integrating the individual abstract syntax trees will be described. FIG. 40 is a flowchart illustrating an example of the execution procedure abstract syntax tree generation processing procedure. Here, an example of integrating the individual abstracts syntax trees in FIG. 41, which is generated on the basis of the operation outline field C4 of the "Cell culture using differentiation-inducing culture medium B", and the individual abstract syntax tree in FIG. 42, which is generated on the basis of the operation outline field C5 of the "Evaluation process", in regard to the execution procedure shown in FIG. 6, is shown.

Here, a case where a plurality of individual abstract syntax trees are generated and these individual abstract syntax trees are integrated, will be described; however, depending on the template execution procedure, there may be only one operation outline field, and only one individual abstract syntax tree may be generated. In this case, as described above, one individual abstract syntax tree that has been generated is handled as the execution procedure abstract syntax tree.

Figure 41:
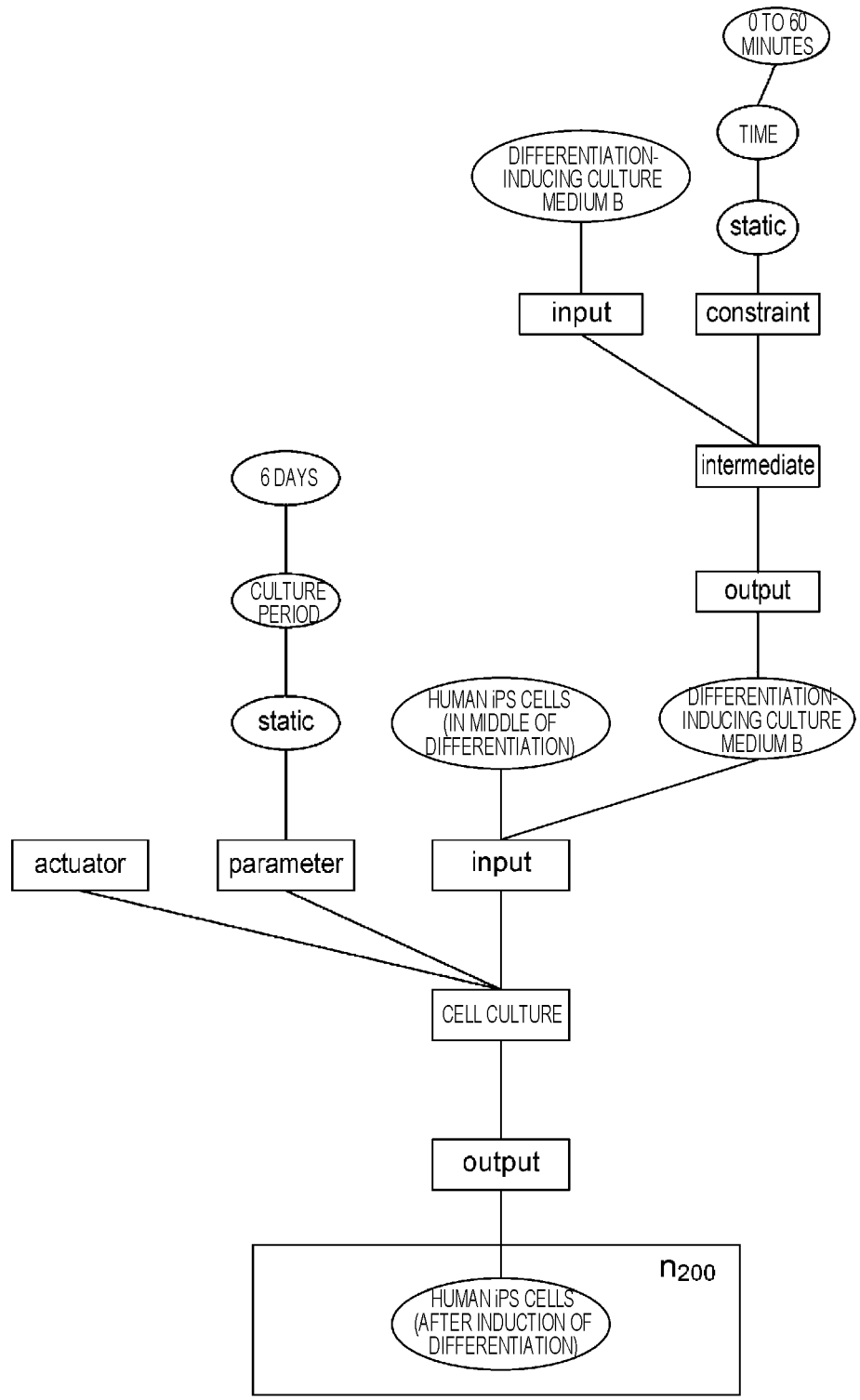
FIG. 41 is a schematic view illustrating a configuration (1) of individual abstract syntax trees integrated by execution e abstract syntax tree generation processing.

As shown in FIG. 40, the execution procedure abstract syntax tree generation unit 1902 starts the execution procedure abstract syntax tree generation processing procedure from a start step, and in a next step S4201, selects a predetermined individual abstract syntax tree (here, for example, an individual abstract syntax tree related to the operation of "Evaluation process" that is finally performed (FIG. 42)) from among a plurality of individual abstract syntax trees shown in FIG. 31, FIG. 32, FIG. 33, and FIG. 34 (FIG. 41 has the same configuration as that in FIG. 34).

Figure 42:
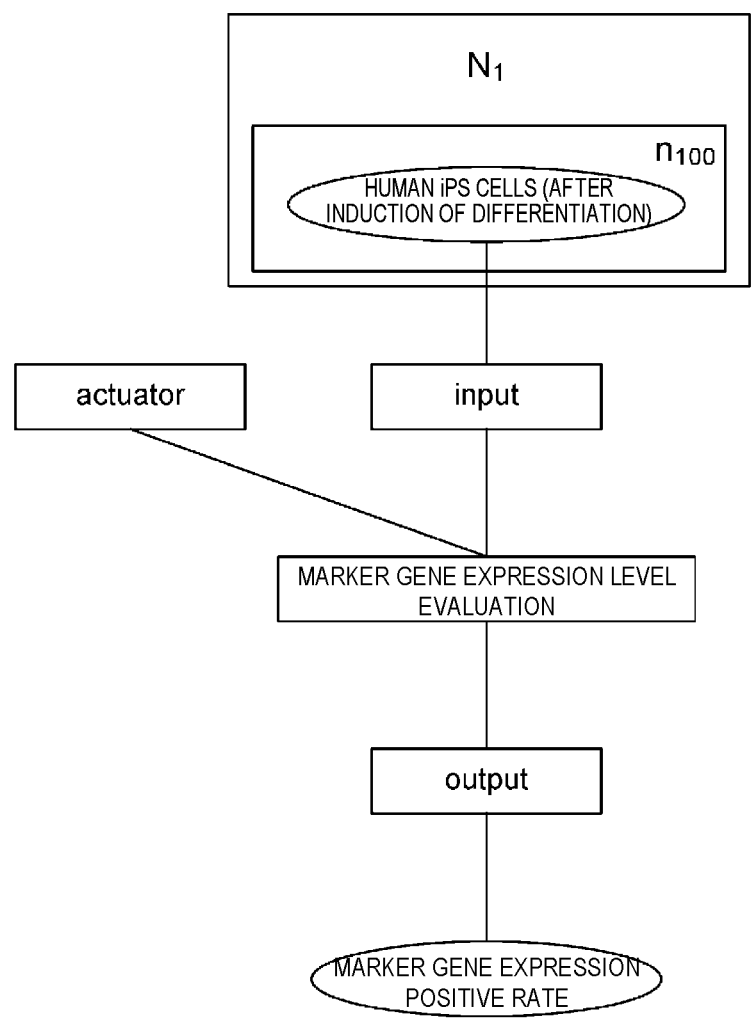
FIG. 42 is a schematic view illustrating a configuration (2) of individual t syntax trees integrated by the execution procedure abstract syntax tree generation processing.

In a next step S4202, the execution procedure abstract syntax tree generation unit 1902 identifies a set $N_1$ of input label nodes having no child, which are included in the individual abstract syntax tree of the "Evaluation process" selected in the previous step S4201, as shown in FIG. 42.

In a next step S4203, the execution procedure abstract syntax tree generation unit 1902 identifies an individual abstract syntax tree of "Cell culture using differentiation-inducing culture medium B", which has an output object node $n_{200}$ having the same label (for example, a node name enabling discrimination of the node) as that of an input object node (here, an input object node with the label of "Human iPS cells (after induction of differentiation)") $n_{100}$ included in the set $N_1$ of FIG. 42 but does not have a parent for the output object node $n_{200}$, as shown in FIG. 41.

Figure 43:
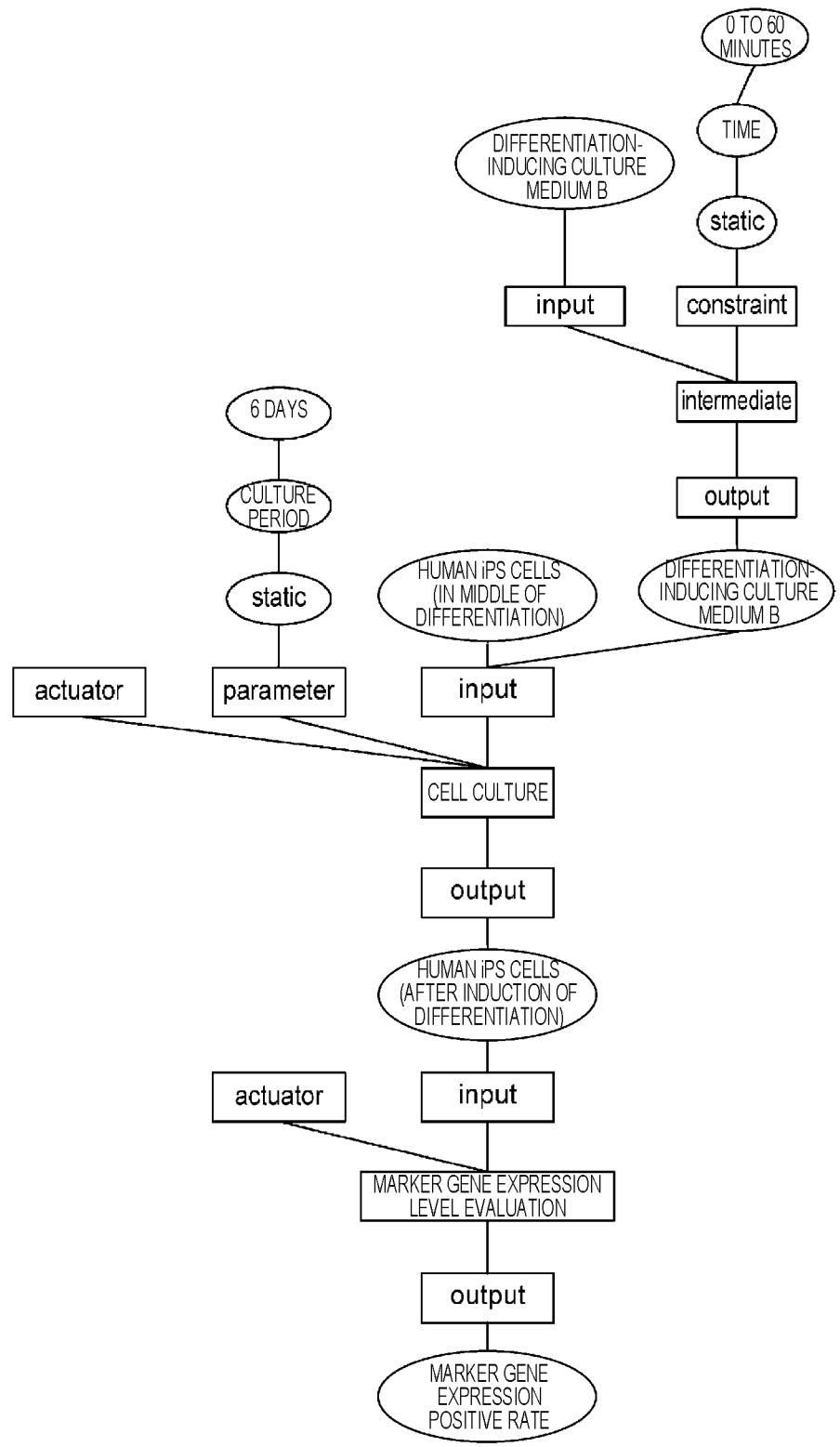
FIG. 43 is a schematic view illustrating a configuration of an intermediate abstract syntax tree in which the individual abstract syntax tree shown in FIG. 41 and the individual abstract syntax tree shown in FIG. 42 are integrated.

In a next step S4204, the execution procedure abstract syntax tree generation unit 1902 replaces the output object node $n_{200}$ of the individual abstract syntax tree of the "Cell culture using differentiation-inducing culture medium B" shown in FIG. 41, which has been identified in the previous step S4203, with an input object node $n_{100}$ included in the set $N_1$ of the individual abstract syntax tree of the "Marker gene expression evaluation" shown in FIG. 42, connects the individual abstract syntax tree in FIG. 42 and the individual abstract syntax tree in FIG. 43, and generates an intermediate abstract syntax tree shown in FIG. 43.

In a next step S4205, the execution procedure abstract syntax tree generation unit 1902 decides whether there is an individual abstract syntax tree or an intermediate abstract syntax tree, which can be connected to an element of the set $N_1$ of the input label nodes having no child, the set $N_1$ being included in the intermediate abstract syntax tree. Here, in a case where there are one or more individual abstract syntax trees or intermediate abstract syntax trees that can be connected to the set $N_1$ of the input label nodes having no child, the input label node being included in the intermediate abstract syntax tree, the execution procedure abstract syntax tree generation unit 1902 proceeds again to the above-mentioned step S4203 and identifies an individual abstract syntax tree that can be connected to a new set $N_1$ included in the intermediate abstract syntax tree. As described above, in a step S4205, the above-mentioned processing is repeated until there is no individual abstract syntax tree or intermediate abstract syntax tree that can be connected to an element of the set $N_1$ of input label nodes having no child, the set $N_1$ being included in the intermediate abstract syntax tree.

On the other hand, in the step S4205, in a case where there is no individual abstract syntax tree or intermediate abstract syntax tree that can be connected to an element of the set $N_1$ of input label nodes having no child, the set $N_1$ being included in the intermediate abstract syntax tree, in a next step S4207, the execution procedure abstract syntax tree generation unit 1902 outputs the intermediate abstract syntax tree as the final execution procedure abstract syntax tree t' (FIG. 8 and FIG. 9) and ends the above-mentioned execution procedure abstract syntax tree generation processing procedure.

(1-4-4) Extended Abstract Syntax Tree Generation Processing

Figure 44:
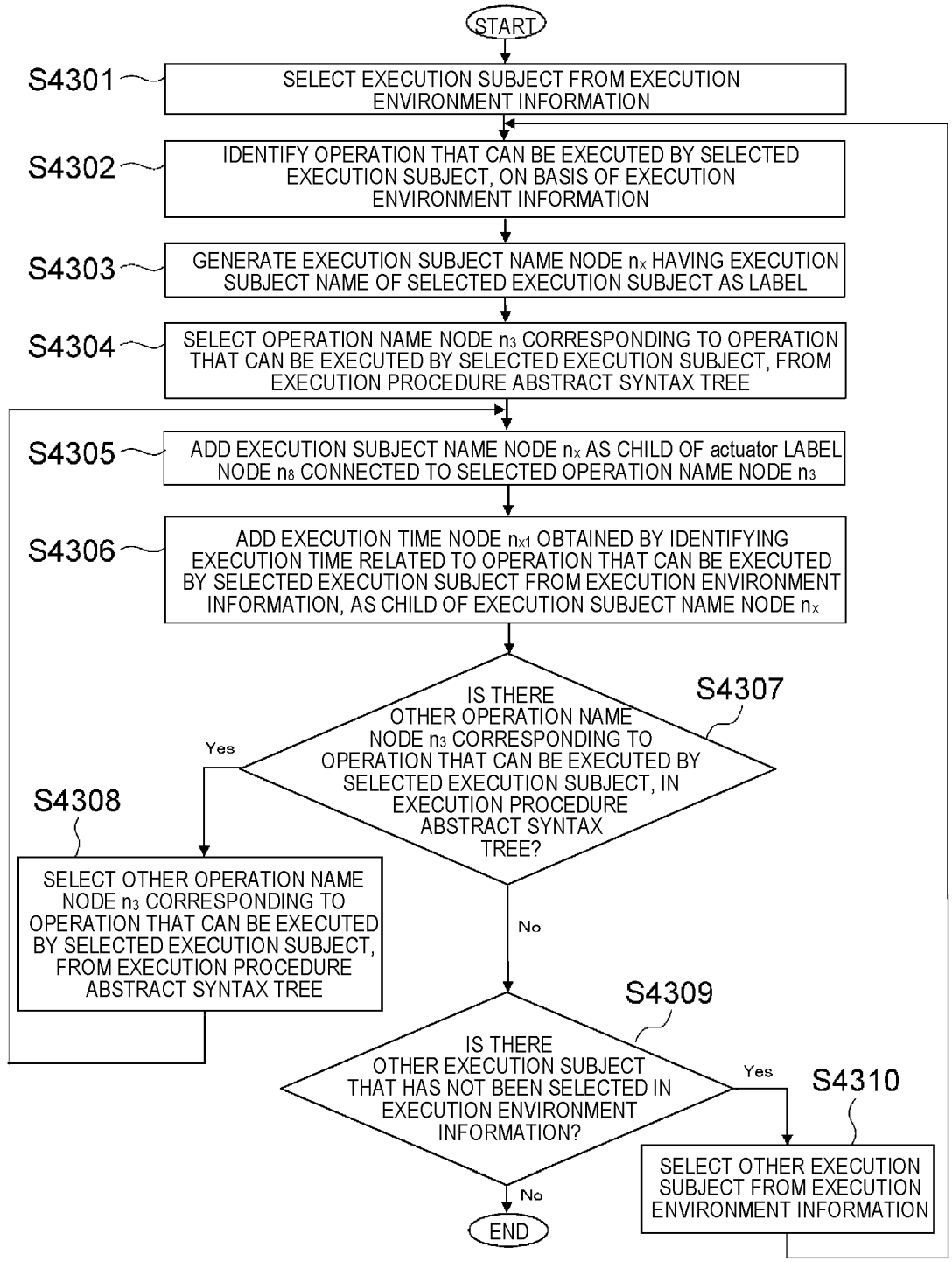
FIG. 44 is a flow chart illustrating an extended abstract syntax tree generation processing procedure.

Next, the above-mentioned extended abstract syntax tree generation processing procedure will be described. FIG. 44 is a flowchart illustrating an example of the extended abstract syntax tree generation processing procedure. Here, an example of generating an extended abstract syntax tree t' (FIG. 12, FIG. 13, and FIG. 14) on the basis of the execution environment information E shown in FIG. 10A and the execution procedure abstract syntax tree t shown in FIG. 8, FIG. 9A, and FIG. 9B will be described.

As shown in FIG. 44, the extended abstract syntax tree generation unit 1903 starts the extended abstract syntax tree generation processing procedure from a start step, and in a next step S4301, selects a predetermined execution subject from the execution environment information E in FIG. 10A. Here, in order to simplify the description, an example of selecting, for example, the "Culture medium mixing device P" as the execution subject will be described. In a next step S4302, the extended abstract syntax tree generation unit 1903 identifies an operation that can be executed by the execution subject "Culture medium mixing device P" selected in the previous step S4301, from the information of the execution environment information E.

For example, with regard to the execution environment information E shown in FIG. 10A, it is identified that in the case of the culture medium mixing device P that can be the execution subject, only the operations of adjustment of the culture medium A and adjustment of the culture medium B can be executed; in the case of the cell culture devices X and Y that can be the execution subjects, only the operation of culturing cells can be executed; and in the case of the flow cytometer Q that can be the execution subject, only the operation of expression evaluation of a marker gene can be executed.

In a next step S4303, the extended abstract syntax tree generation unit 1903 generates an execution subject name node $n_x$ of "Culture medium mixing device P" in which the execution subject selected in the previous step S4301 is used as a label (for example, an execution subject name enabling discrimination of the execution subject). More specifically, for example, in the case of the culture medium mixing device P, the execution subject name node $n_x$ is an execution subject name node $n_x$ that uses the "Culture medium mixing device P", which enables discrimination of the culture medium mixing device P, as a label, and in the case of the cell culture device X, the execution subject name node $n_x$ is an execution subject name node $n_x$ that uses the "Cell culture device X", which enables discrimination of the cell culture device X, as a label.

In a next step S4304, the extended abstract syntax tree generation unit 1903 selects the operation name node $n_3$ corresponding to the operation that can be executed by the "Culture medium mixing device P" that is the execution subject selected in the previous step S4301 (that is, "Adjustment of culture medium") from the execution procedure abstract syntax tree t. In the step S4301, in a case where the "Culture medium mixing device P" for which "Adjustment of culture medium" is an executable operation is selected, the operation name node $n_3$ is shown by using FIG. 12 showing the extended abstract syntax tree t', and the operation name node $n_3$ of "Adjustment of culture medium" (that is, "Adjustment of culture medium" in FIG. 9A) is selected from the execution procedure abstract syntax tree t.

In a next step S4305, the extended abstract syntax tree generation unit 1903 adds the execution subject name node $n_x$ of the "Culture medium mixing device P" as a child of the actuator label node $n_8$ connected to the operation name node $n_3$ of the "Adjustment of culture medium" selected in the previous step S4304, through an edge.

In a next step S4306, the extended abstract syntax tree generation unit 1903 identifies an execution time related to the operation of "Adjustment of culture medium" that can be executed by the "Culture medium mixing device P" selected in the previous step S4301 from the execution environment information E, and as shown in FIG. 12, adds an execution time node $n_{x1}$ indicating this execution time (here, "30 minutes") as a child of the execution subject name node $n_x$ of the "Culture medium mixing device P" through an edge.

In a next step S4307, the extended abstract syntax tree generation unit 1903 decides whether there is another operation name node $n_3$ corresponding to another operation that can be executed by the "Culture medium mixing device P" selected in the previous step S4301, in the execution procedure abstract syntax tree t.

For example, in a case where the "Culture medium mixing device P" is selected, the operation of "Adjustment of culture medium" as the other operation that can be executed by the "Culture medium mixing device P" is also present in FIG. 9B. Therefore, in this case, in a next step S4308, the extended abstract syntax tree generation unit 1903 selects the operation name node $n_3$ of the "Adjustment of culture medium" corresponding to the operation that can be executed by the "Culture medium mixing device P" selected in the previous step S4301, from the execution procedure abstract syntax tree t, returns again to the step S4305, and repeats the above-mentioned processing.

On the other hand, in a case where a negative result is obtained in the step S4307, this indicates that the execution subject name node $n_x$ or the execution time node $n_{x1}$ of the "Culture medium mixing device P" is added to all of the operation name nodes $n_3$ (as shown in FIG. 13 and FIG. 14, the operation name node $n_3$ of "Adjustment of culture medium") that can be executed by the "Culture medium mixing device P" in the execution procedure abstract syntax tree t, and in this case, the extended abstract syntax tree generation unit 1903 proceeds to a next step S4309.

In the step S4309, the extended abstract syntax tree generation unit 1903 decides whether there is another execution subject (for example, the cell culture device X or Y, or the flow cytometer Q) that is not selected in the execution environment information E, and in a case where there is no other execution subject, this indicates that the extended abstract syntax tree t' in which all the execution subjects in the execution environment information E are specified as nodes in the execution procedure abstract syntax tree t, is generated, and the above-mentioned extended abstract syntax tree generation processing procedure is ended.

On the other hand, in the step S4309, in a case where there is another execution subject (for example, the cell culture device X or Y, or the flow cytometer Q) that is not selected in the execution environment information E, in a next step S4310, the extended abstract syntax tree generation unit 1903 selects another execution subject in the execution environment information E, returns again to the step S4302, and repeats the above-described processing until a negative result is obtained in the step S4309.

(1-4-5) Partial Order Generation Processing

Next, the processing procedure for generating the above-mentioned partial order will be described. In this case, the partial order generation unit 1905 generates the partial order shown in FIG. 10B from the extended abstract syntax tree. The partial order generation unit 1905 extracts the respective operation name nodes $n_3$ of the "Adjustment of differentiation-inducing culture medium A" and "Adjustment of differentiation-inducing culture medium B" having no operation name node $n_3$ for descendants, among the operation name nodes $n_3$ of the extended abstract syntax tree t', as shown in "step 1" of FIG. 45.

Figure 45:
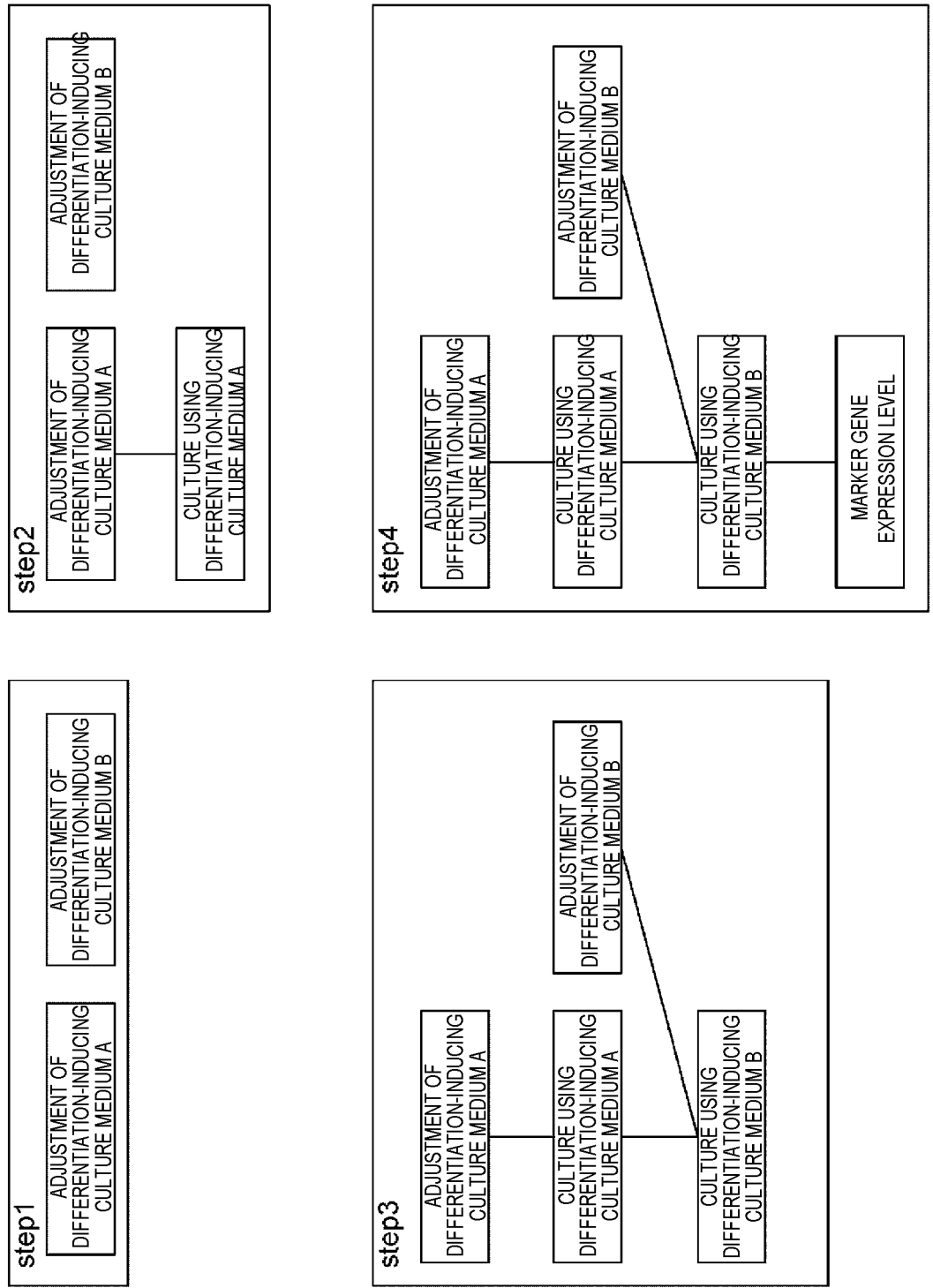
FIG. 45 is a schematic view for describing an outline of a partial order.

The partial order generation unit 1905 extracts an operation name node $n_3$ of "Culture using differentiation-inducing culture medium A" (in the extended abstract syntax tree t', simply described as "Cell culture") having only the operation name node $n_3$ of "Adjustment of differentiation-inducing culture medium A" that has no operation name node $n_3$ for the descendants, as a child among the operation name nodes $n_3$ of the extended abstract syntax tree t', and adds the operation name node $n_3$ of "Adjustment of differentiation-inducing culture medium A" as a child of the operation name node $n_3$ of "Culture using differentiation-inducing culture medium A" through an edge, as shown in "step 2" of FIG. 45. With regard to the extended abstract syntax tree t', since the operation name node $n_3$ of "Culture using differentiation-inducing culture medium B" (in the extended abstract syntax tree t', simply described as "Cell culture") has not only the operation name node $n_3$ of "Adjustment of differentiation-inducing culture medium B" but also the operation name node $n_3$ of "Culture using differentiation-inducing culture medium A" as children, there is no operation name node having only the operation name node $n_3$ of "Adjustment of differentiation-inducing culture medium B" as a child. Therefore, no other operation name node $n_3$ is added to the operation name node $n_3$ of "Adjustment of differentiation-inducing culture medium B".

Subsequently, as shown in "step 3", the operation name node $n_3$ of "Culture using differentiation-inducing culture medium B" having the operation name nodes $n_3$ of "Culture using differentiation-inducing culture medium A" and "Adjustment of differentiation-inducing culture medium B", which have no operation name node $n_3$ for descendants, as children, is extracted, and the respective operation name nodes $n_3$ of "Culture using differentiation-inducing culture medium A" and "Adjustment of differentiation-inducing culture medium B" are added as children of the operation name node $n_3$ of "Culture using differentiation-inducing culture medium B" through edges.

The partial order generation unit 1905 similarly extracts the operation name node $n_3$ of "Marker gene expression evaluation" having the operation name node $n_3$ of "Culture using differentiation-inducing culture medium B" as a child, on the basis of the extended abstract syntax tree t' as shown in "step 4" of FIG. 45, adds the operation name node $n_3$ of "Culture using differentiation-inducing culture medium B" as a child of the operation name node $n_3$ of "Marker gene expression evaluation" through an edge, and obtains a partial order, which is the final processing result.

(1-5) Execution Instruction Information Generation Processing

Figure 46:
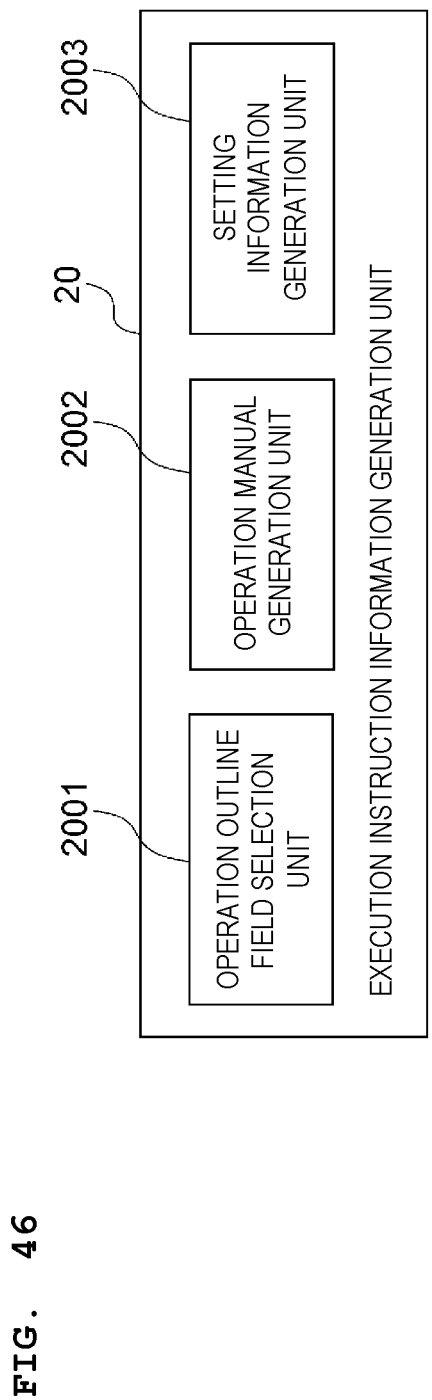
FIG. 46 is a block diagram illustrating a configuration of an execution instruction information generation unit.
Figure 47:
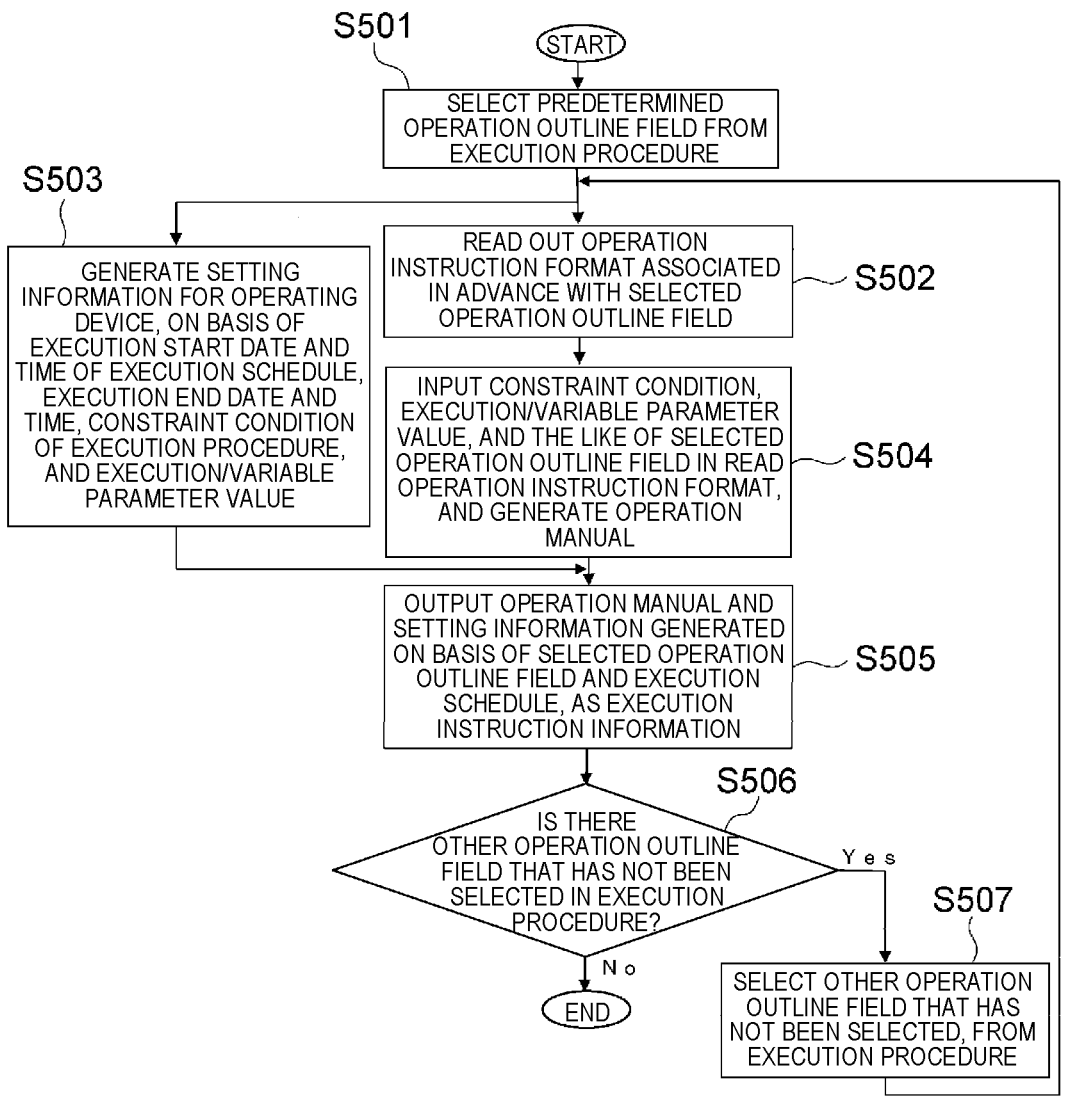
FIG. 47 is a flow chart illustrating an execution instruction information generation processing procedure.

Next, the above-mentioned execution instruction information generation processing procedure will be described. FIG. 46 is a block diagram illustrating the configuration of the execution instruction information generation unit 20. In addition, FIG. 47 is a flowchart illustrating the execution instruction information generation processing procedure. As shown in FIG. 46, the execution instruction information generation unit 20 includes an operation outline field selection unit 2001, an operation manual generation unit 2002, and a setting information generation unit 2003.

In the present embodiment, the operation manual and setting information that will be described below as the execution instruction information are set as the execution instruction information; however, the invention is not limited to this, and for example, only the operation manual may be set as the execution instruction information, or only the setting information may be used as the execution instruction information.

In this case, as illustrated in FIG. 47, the execution instruction information generation unit 20 starts the execution instruction information generation processing procedure from a start step. In a step S501, for example, the operation outline field selection unit 2001 selects a predetermined operation outline field C1 from the execution procedure shown in FIG. 6 and proceeds to next step S502 and step S503.

In the next step S502, the operation manual generation unit 2002 reads out an operation instruction format that has been associated in advance with the operation outline field C1 selected in the step S501, from the database 8.

For example, the operation instruction format is commands or the like in a format set in advance by a natural language that can be read out by the culture medium mixing device P or the like, and is presented such that the contents of the execution procedure or the contents of an execution schedule generated on the basis of the execution procedure can be discriminated by the culture medium mixing device P or the like, which is an execution subject, by using a predetermined language. Alternatively, in a case where the execution subject such as the culture medium mixing device P is operated by a man, the operation instruction format is sentences in a format set in advance by a natural language, and may be any format as long as the contents of the execution procedure or the contents of an execution schedule generated on the basis of the execution procedure can be presented so as to be understood by the man by the natural language.

In a next step S504, the operation manual generation unit 2002 reads out the constraint information, the execution parameter value, the variable parameter value, and the like of the operation outline field C1 selected in the step S501, as well as the hour information and the like of the execution schedule, inputs the read contents to the respective regions determined in advance in the operation instruction format, and generates the operation manual.

The operation manual may be in various formats as long as the contents of the execution procedure or the contents of the execution schedule generated on the basis of the execution procedure can be created such that men can understand the contents by a natural language. An operation manual created in a natural language does not have to be outputted in a case where a man does not lie between devices such as the culture medium mixing device P, which are execution subjects.

On the other hand, in the step S503, the setting information generation unit 2003 generates, for example, setting information such as a program for operating the culture medium mixing device P, which is the execution subject of the operation outline field C1 selected in the step S501, on the basis of an execution start date and time at which an execution subject starts the execution of an operation, the execution end date and time at which the execution subject ends the execution of the operation, and the constraint conditions, the execution parameter values, and the variable parameter values of the execution procedure, which are determined in the execution schedule.

In a step S505, the execution instruction information generation unit 20 outputs the operation manual and the setting information generated on the basis of the operation outline field C1 selected in the step S501 and the execution schedule, as execution instruction information.

In a next step S506, the execution instruction information generation unit 20 decides whether there is an outline field that is not selected in the operation execution procedure, and in a case where there is an operation outline field (Yes), in a step S507, the operation outline field selection unit 2001 selects the operation outline field C2 or the like that is not selected in the step S501 and returns again to the above-described step S502.

As described above, the execution instruction information generation unit 20 can generate execution instruction information for each of all the operation outline fields C1, C2, C3, C4, and C5 in the execution procedure by repeating the above-described processing until a negative result (No) is obtained in the step S506.

(1-6) Modification Example

In the above-described sections (1-1) to (1-5), a case of applying a culture-related process consisting of a culture medium adjustment process and a cell culture process, for example, as in the case of the operation outline fields C1 to C4 in the execution procedure 1 of FIG. 6, has been described. However, the culture-related process may be a culture-related process including at least any one of a culture medium adjustment process including operations related to the adjustment of culture media (operation outline fields C1 and C3) as the operations, and a cell culture process including operations related to cell culture using culture media (operation outline fields C2 and C4). That is, in the above-described embodiment, for example, only one of the operation outline fields C1 to C4 may be applied as the culture-related process.

For instance, in a case where there is only the operation outline field C1 of FIG. 6 in the execution procedure, the culture-related process optimization device 2 generates a template execution procedure, an execution procedure, and the like for allowing the culture medium mixing device P to execute only the "Adjustment of differentiation-inducing culture medium A" (operation of operation outline field C1). More specifically, for example, when a user inputs a command for executing only the operation of the operation outline field C1 through the operation unit 10, the culture-related process optimization device 2 generates a plurality of execution procedures having different variable parameter values from the operation outline field C1, transmits the plurality of execution procedures to the culture medium mixing device P, and at the same time, allows the culture medium mixing device P to repeatedly execute the "Adjustment of differentiation-inducing culture medium A" according to each execution procedure.

Here, the variable parameter values of the operation outline field C1 may be determined on the basis of previous execution performance results as described above, or may be set in advance by the user through the operation unit 10. As a result, a plurality of culture media A adjusted on the basis of a plurality of combinations of variable parameter values are generated. Then, a predetermined evaluation process is executed for each of the generated culture media A to obtain an evaluation result for each culture medium A, and the execution results and evaluation results thereof are accumulated in the culture-related process optimization device 2. The culture-related process optimization device 2 records the obtained execution procedures, variable parameter values, execution results, and evaluation results in association with each other, in the database 8.

(1-7) Functions and Effects

With regard to the above-described configurations, in the culture-related process optimization method according to the present embodiment, a starting point execution procedure that serves as a starting point for search, in which a plurality of operations sequentially performed in the culture-related process related to cell culture are each specified as an operation item, and information related to the operations is specified, is acquired (acquisition step). In the culture-related process optimization method, one or a plurality of variable parameter items for which variable parameter values can be set in the starting point execution procedure are identified (variable parameter item identification step), and an execution procedure is generated by setting the variable parameter values for the variable parameter items identified in the variable parameter item identification step on the basis of previous execution performance results and evaluation performance results thereof (execution procedure generation step).

In addition, in the culture-related process optimization method, an execution result when the execution subject executes the execution according to this execution procedure in the execution environment is acquired (execution result acquisition step), and an evaluation result with respect to the execution result is acquired (evaluation result acquisition step). In the culture-related process optimization method, the execution procedure, variable parameter values, the execution performance result, and the evaluation result are recorded in association with each other (storage step).

As a result, the culture-related process optimization method can be utilized as a clue for an execution subject to actually execute the culture-related process in the execution environment 100 on the basis of the execution procedure, variable parameter values, the execution result, and the evaluation result, and to search for an execution procedure under an optimal production condition in which a gain as large as possible is obtained, and an optimal production condition (condition for adjusting a culture medium, condition for culturing cells, or the like) with a large gain can be sought by experiments at a number of times as minimal as possible. Furthermore, in the culture-related process optimization method, since an optimal production condition with a large gain can be sought by experiments at a number of times as minimal as possible, reduction of the total cost and efforts needed for searching for the production condition can be promoted, and at the same time, an optimal culture-related process with a large gain can be sought.

(2) Culture-Related Process Optimization Method According to Second Embodiment

Next, a culture-related process optimization method according to a second embodiment will be described. In the culture-related process optimization method according to the second embodiment, when a variable parameter item to be set for the template execution procedure is selected, an item selection simulation is executed, and a variable parameter item is selected from the starting point execution procedure on the basis of the result of the item selection simulation.

In addition, in the culture-related process optimization method according to the second embodiment, when variable parameter values are selected from within a search range set for a variable parameter item of the template execution procedure, a variable parameter value selection simulation is executed, and variable parameter values are selected from within a search range for each variable parameter item on the basis of the result of the variable parameter value selection simulation.

In the culture-related process optimization method according to the second embodiment, when an execution procedure to be executed in the execution environment 100 is optimized by sequential optimization, the number of times of condition examination in the execution environment 100 can be cut down by narrowing in advance the range of the types of variable parameter items by an item selection simulation before the execution procedure is actually executed in the execution environment 100 and optimization is performed in sequence, or the number of times of condition examination in the execution environment 100 can be cut down by utilizing a simulation analysis result obtained on the basis of the variable parameter value selection simulation in advance to limit the range of the variable parameter value in advance.

When optimization of the execution procedure to be executed in a certain execution environment 100 is performed, in a case where the number of variables that can be optimization targets is large, or in a case where a categorical variable (for example, the type of a reagent to be added) is included in the variables, a huge number of experiments are required to perform the search by using simple sequential optimization. Since many of the culture-related processes that are executed in the execution environment 100 usually require high temporal and financial cost to execute one execution procedure, it is not realistic to allow an execution subject to perform an execution procedure a huge number of times for the optimization according to an execution procedure generated by the culture-related process optimization system 1.

In the culture-related process optimization method according to the second embodiment, the execution subject actually executes the execution procedure in the execution environment 100 by using the simulation analysis result, and limits the variable parameter item or the range of the variable parameter value to be optimized. By performing narrowing-down according to the culture-related process optimization method, the number of times of the execution procedure that is actually performed in the execution environment 100 can be cut down to a large extent.

Particularly, in the case of a system such as a bioplant, in which the execution environment 100 is a complicated system and there are many hidden variables, since a prediction accuracy of the behavior of the system by a simulation is poor (+it is also difficult to align the dimension), and there are many cases where a prediction value of the optimal condition based on the simulation is not directly with the optimal production condition of the real world, while on the other hand, a relationship in the responsiveness of an objective function with respect to the type of the variable of the condition to be changed may be common between the simulation and the real world to some extent. In such a case, even when the execution environment 100 is a complicated system, by globally fluctuating the experiment condition (variable parameter item or variable parameter value) by a simulation, for example, a variable for changing the value of the objective function and a variable that does not change the value can be broadly classified, or the response characteristics of the objective variable with respect to the explanatory variable can be broadly grasped. With reference to such information, a search range (a variable parameter item or a variable parameter value) is set among the variables that are predicted to contribute to the value of the objective function, or the shape of the regression model to be used is determined, and thereby a search for the variable parameter item or the variable parameter value can be efficiently carried out.

Here, the culture-related process optimization method according to the second embodiment will be described by using a bioplant with particularly many hidden variables as an example. More specifically, for example, a culture-related process in which there is *Escherichia coli* X to which a plasmid for expressing an enzyme P that produces a certain compound A has been introduced, this *Escherichia coli* X is cultured in a culture medium M, and the compound (hereinafter, also referred to as objective substance) A is produced by inducing expression of the enzyme P, is assumed, and hereinafter, the item selection simulation and the variable parameter value selection simulation will be sequentially described.

(2-1) Template Execution Procedure Generation Processing Using Item Selection Simulation First, with regard to the culture-related process optimization method, a case of generating a template execution procedure in which several types of optimal raw materials for composing a culture medium M that maximizes the yield [g/L] of the objective substance A are identified as a variable parameter item by using an item selection simulation, will be described.

Here, for example, in a case where there are several hundred types of candidate raw materials for composing the culture medium M, in order to obtain a culture medium M that can maximize the yield of the objective substance A in the culture-related process, there is a great burden when an execution subject is allowed to actually execute the execution procedure in the execution environment 100 and identify the issues of which is an optimal raw material to be selected from among these several hundred types of candidate raw materials, which are optimal raw materials to be combined, or which is an optimal formulation for mixing each raw material, from the obtained execution results and evaluation results.

Thus, in the second embodiment, when the template execution procedure is generated, narrowing-down of the raw materials for composing the culture medium M that may possibly maximize the yield of the objective substance A, from among several hundred types of candidate raw materials for composing the culture medium M, is performed in advance by executing the item selection simulation, and the number of times of the execution procedure actually performed in the execution environment 100 is drastically cut down.

Figure 48:
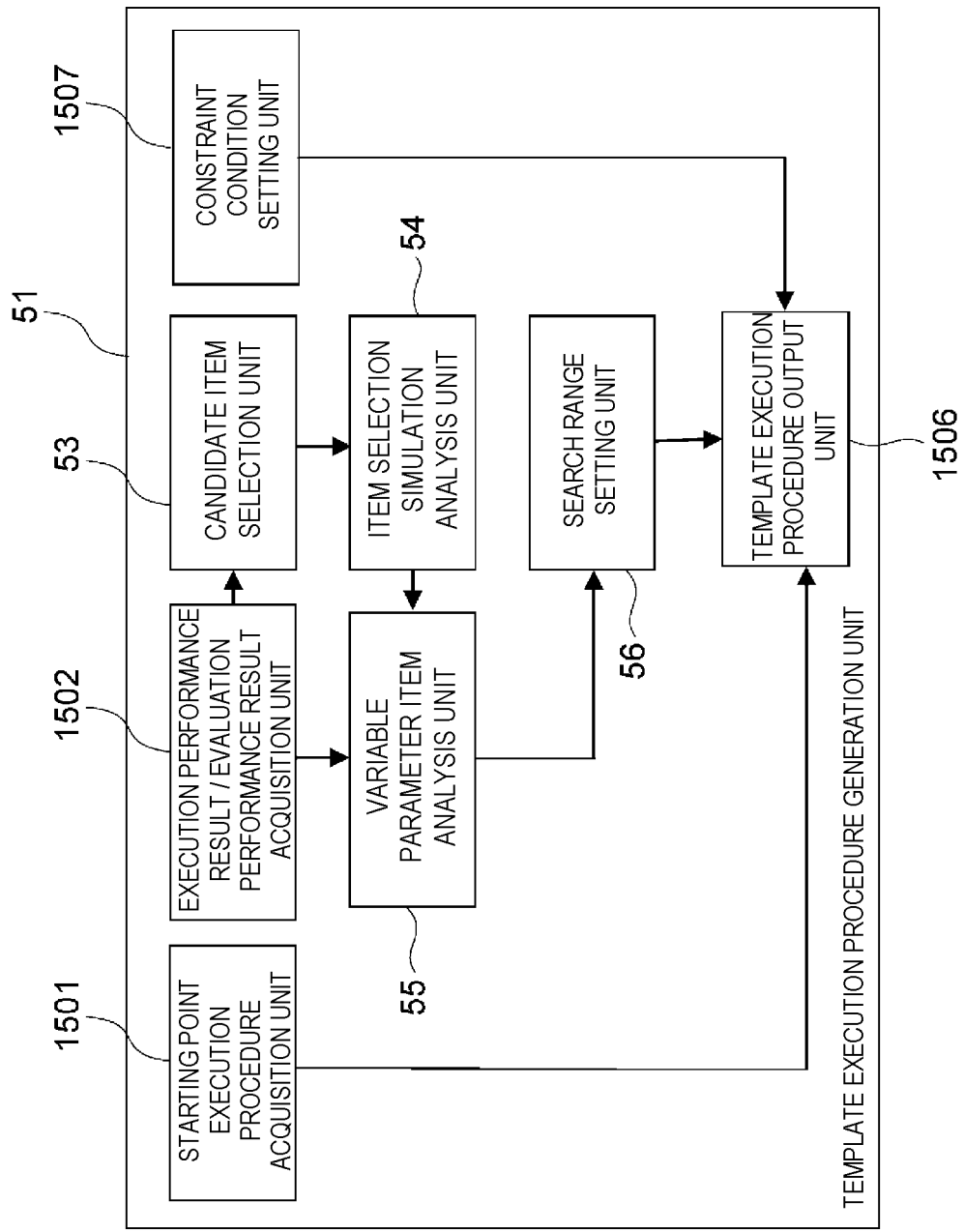
FIG. 48 is a block diagram illustrating a configuration of a template execution procedure generation unit according to a second embodiment.
Figure 49:
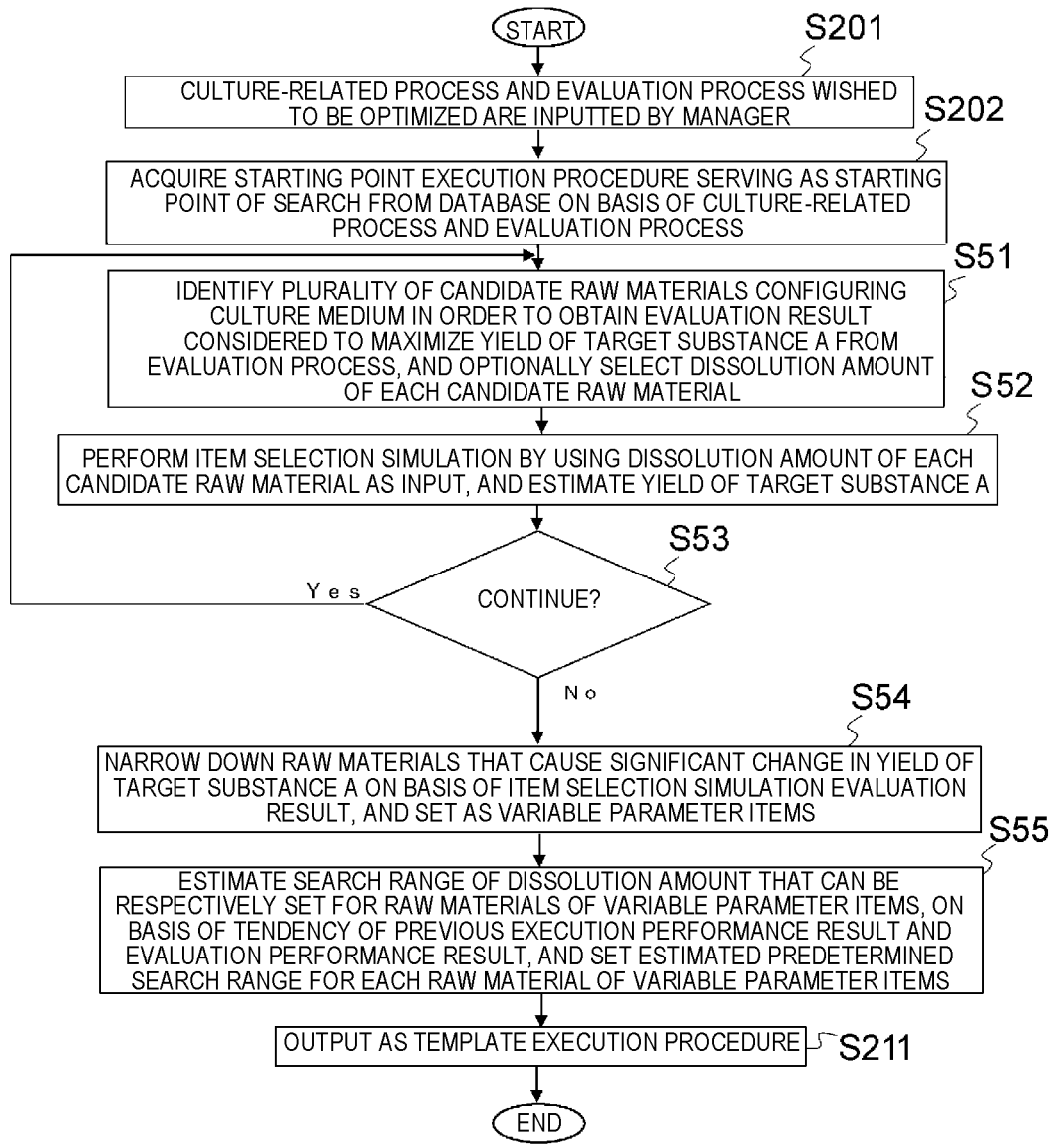
FIG. 49 is a flow chart illustrating a template execution procedure generation processing procedure according to the second embodiment.

Here, FIG. 48 is a block diagram illustrating the configuration of a template execution procedure generation unit 51 according to the second embodiment. In addition, FIG. 49 is a flowchart illustrating the template execution procedure generation processing procedure according to the second embodiment. As shown in FIG. 48, the template execution procedure generation unit 51 includes a starting point execution procedure acquisition unit 1501, an execution performance result/evaluation performance result acquisition unit 1502, a candidate item selection unit 53, an item selection simulation analysis unit 54, a variable parameter item analysis unit 55, a search range setting unit 56, a template execution procedure output unit 1506, and a constraint condition setting unit 1507.

As shown in FIG. 49, the culture-related process optimization device 2 starts the template execution procedure generation processing procedure from a start step, and in a next step S201, the culture related process and evaluation process wished to be optimized are inputted by the manager.

In a next step S202, the starting point execution procedure acquisition unit 1501 acquires a starting point execution procedure that serves as a starting point of the search from the database 8, on the basis of the culture-related process and the evaluation process. In a step S51, the candidate item selection unit 53 identifies a plurality of candidate raw materials for composing the culture medium M (also referred to as a candidate variable parameter item), for obtaining an evaluation result of maximizing the yield of the objective substance A by an evaluation process, and a predetermined dissolution amount as a parameter value for item selection of each candidate raw material is arbitrarily selected. The number of candidate variable parameter items (candidate raw materials) is not particularly limited, and here, the number is set to two or more (a plurality), such as 9 or 10; however, the number may be one. In addition, the candidate variable parameter item (candidate raw material) may be identified by the manager, or may be identified on the basis of a previously obtained item selection simulation evaluation result, which will be described below, and the method for identification thereof is not particularly limited.

For example, in a case where m kinds of candidate raw materials for composing the culture medium M are identified from a metabolic network, previous execution performance results and evaluation performance results related to the culture medium M may be acquired by the execution performance result/evaluation performance result acquisition unit 1502 from the database 8, and for example, m kinds of candidate raw materials may be identified from among the raw materials of the culture medium M used in this execution performance result and the like, or m kinds of candidate raw materials may be identified from within a predetermined region of the metabolic network with a focus on the raw materials of the culture medium M used in the execution performance result and the like.

The metabolic network is data indicating the route of chain chemical reactions occurring in cells in biochemistry, and in this case, the metabolic network is stored in advance in the database 8. The candidate item selection unit 53 acquires the metabolic network from the database 8 and selects m kinds of candidate raw materials for composing the culture medium M on the basis of the metabolic network.

In a step S52, the item selection simulation analysis unit 54 performs an item selection simulation by using the dissolution amount of m kinds of candidate raw materials identified in the step S51 as input, and obtains an output result estimating the level of the yield of the objective substance A as an item selection simulation evaluation result.

Here, since the raw materials for composing the culture medium M are described as an example, the parameter value for item selection is the dissolution amount; however, it is obvious that in other culture-related processes, the parameter value for item selection may be, for example, concentration, mixing amount, temperature, or time.

Here, in the item selection simulation, for example, when it is assumed that a cell simulation of E-cells or the like, a biochemical reaction system that is operated under a non-ideal condition molecular congestion or localization, or the like is modelized in advance, and by using this model, for example, *Escherichia coli* X is cultured in the culture medium M composed of m kinds of selected raw materials to induce expression of the enzyme P, it is possible to virtually simulate how much yield of the objective substance A is predicted.

As the item selection simulation evaluation result, the item selection simulation analysis unit 54 sets, for example, the time when a predetermined time T has elapsed from the start of the item selection simulation as a start hour, and calculates an integral value of the yield of the objective substance A from the start hour T to the hour (T+Δt) as the item selection simulation evaluation result on the basis of the item selection simulation result.

In a next step S53, the candidate item selection unit 53 newly selects a parameter value for item selection (that is, the dissolution amount of a candidate raw material) of the candidate variable parameter item (candidate raw material), and decides whether to continue the processing of performing the item selection simulation. Whether to continuously execute the item selection simulation may be, for example, determined by the manager, whether the item selection simulation is executed a predetermined number of times may be decided by the candidate item selection unit 53, and whether a desired item selection simulation evaluation result (here, a raw material having a large yield change of the target substance A) is obtained may be decided by the candidate item selection unit 53.

In a step S53, when the candidate item selection unit 53 decides to continue the item selection simulation (Yes), that is, when the manager decides to continue the item selection simulation, or the candidate item selection unit 53 decides that the item selection simulation has not been executed a predetermined number of times, or the candidate item selection unit 53 decides that a desired item selection simulation evaluation result group has not been obtained, the candidate item selection unit 53 returns again to the step S51, selects a new dissolution amount (parameter value for item selection) for the candidate raw material, and in a next step S52, performs the item selection simulation by using the newly selected dissolution amount as input.

As described above, a plurality of candidate raw materials having different dissolution amounts are generated, the item selection simulation is performed for each of the candidate raw materials, and an integral value of the yield of the objective substance A is calculated as an item selection simulation evaluation result for each combination of candidate raw materials with different dissolution amounts.

On the other hand, in a step S53, when the candidate item selection unit 53 decides not to continue the item selection simulation (No), that is, when the manager decides not to continue the item selection simulation, or when the candidate item selection unit 53 decides that the item selection simulation has been executed a predetermined number of times, or when the candidate item selection unit 53 decides that a desired item selection simulation evaluation result group has been obtained, the candidate item selection unit 53 proceeds to a next step S54.

In the step S54, the variable parameter item analysis unit 55 can identify whether a candidate raw material is a raw material having great influence on a yield change or a yield increase of the objective substance A from the yield change (or yield increase), which occurs due to a change in the dissolution amount of the candidate raw material, on the basis of the obtained item selection simulation evaluation result, and on the basis of this, the variable parameter item analysis unit 55 limits the raw material that is the variable parameter item.

In a next step S55, the search range setting unit 56 estimates the search range of the dissolution amount that can be set for each of the raw materials of the variable parameter item narrowed in the step S54, which are considered to affect the yield change (or yield increase) of the objective substance A, on the basis of the tendency of previous actual execution performance results and evaluation performance results, and sets the estimated predetermined search range for each raw material of the variable parameter item.

In a step S211, the template execution procedure output unit 1506 sets the search range sought by the search range setting unit 56 for a starting point execution procedure, generates a template execution procedure on the basis of the starting point execution procedure, outputs the template execution procedure, and ends the above-mentioned template execution procedure generation processing procedure.

In the above-described embodiment, a case has been described in which the type and the number (m kinds) of candidate raw materials are fixed, the dissolution amount of each candidate raw material of the fixed combination is varied, and an item selection simulation is repeatedly performed, and for example, it is obvious that the item selection simulation may be repeatedly performed by suitably varying the type and the number of candidate raw materials to be combined.

(2-2) Template Execution Procedure Generation Processing Using Variable Parameter Value Selection Simulation Next, a variable parameter value selection simulation will be described. In this case, in the culture-related process optimization method, when the variable parameter value is selected within the search range of the template execution procedure, the range of each dissolution amount (mol/L) in 1 (L) that maximizes the yield [g/L] of the objective substance A with respect to a plurality of (for example, m1 kinds) raw materials for composing the culture medium M is narrowed by using the variable parameter value selection simulation, and on the basis of this, a variable parameter value is selected.

Figure 50:
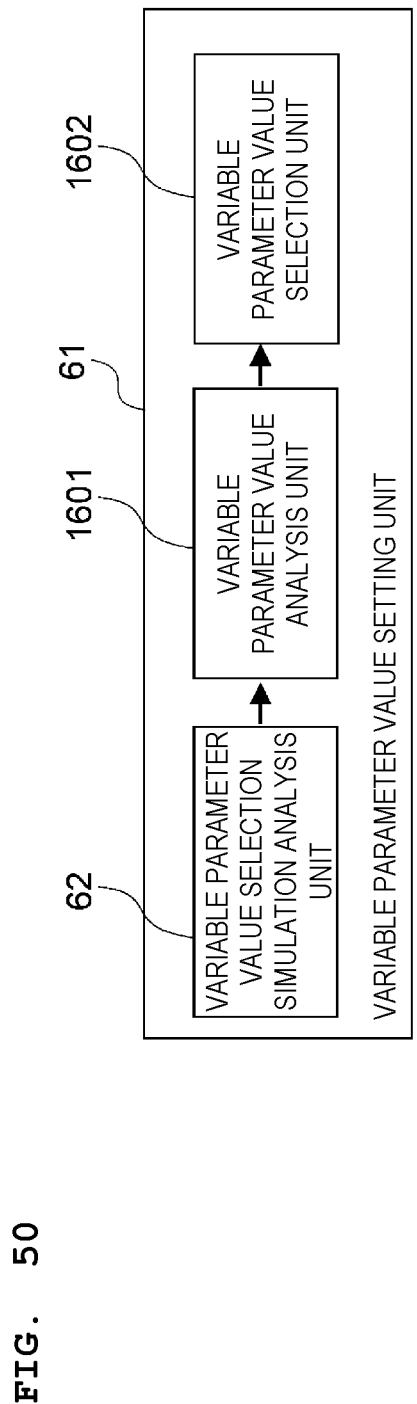
FIG. 50 is a block diagram illustrating a configuration of a variable parameter value setting unit according to the second embodiment.
Figure 51:
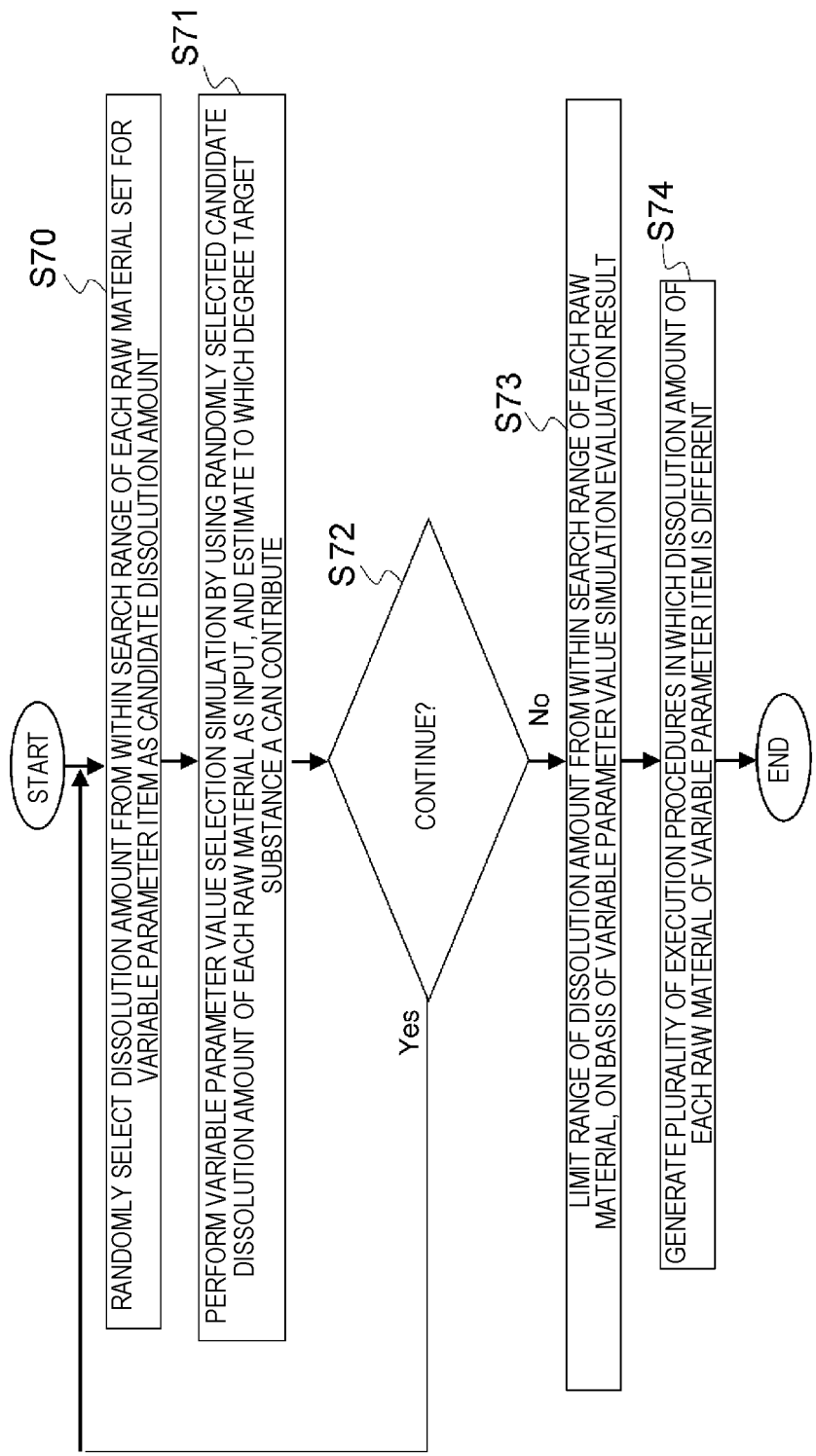
FIG. 51 is a flow chart illustrating a variable parameter value setting processing procedure according to the second embodiment.

Here, FIG. 50 is a block diagram illustrating the configuration of a variable parameter value setting unit 61 according to the second embodiment. In addition, FIG. 51 is a flowchart illustrating a variable parameter value setting processing procedure according to the second embodiment. As shown in FIG. 50, the variable parameter value setting unit 61 includes a variable parameter value selection simulation analysis unit 62, a variable parameter value analysis unit 1601, and a variable parameter value selection unit 1602.

As shown in FIG. 51, the variable parameter value selection simulation analysis unit 62 starts the variable parameter value setting processing procedure from a start step, and in a next step S70, randomly selects each predetermined dissolution amount (for example, a dissolution amount $L_1$ of a raw material $m_1$, a dissolution amount $L_2$ of a raw material $m_2$, a dissolution amount $L_3$ of a raw material $m_3$, and the like in 1 (L)) as a candidate variable parameter value (hereinafter, also referred to as a candidate dissolution amount) from within the search range of each raw material set for the variable parameter item.

In a next step S71, the variable parameter value selection simulation analysis unit 62 performs a variable parameter value selection simulation by using the candidate dissolution amount of each raw material randomly selected in the step S70 as input, and obtains information related to how the yield of the objective substance A is distributed when different concentrations of the culture medium are inputted, as a variable parameter value selection simulation evaluation result.

Here, in the variable parameter value selection simulation, for example, a biochemical reaction system that is operated under a non-ideal condition such as molecular congestion or localization, or the like is modelized in advance by using a cell simulation of E-cells or the like, and when it is assumed that, for example, *Escherichia coli* X is cultured in the culture medium M composed of m kinds of raw materials in predetermined dissolution amounts (for example, a dissolution amount $L_1$ for a raw material $m_1$, a dissolution amount $L_2$ for a raw material $m_2$, a dissolution amount $L_3$ for a raw material $m_3$, or the like), and expression of the enzyme P is induced, it is possible to virtually simulate how much yield of the objective substance A can be expected.

As the item selection simulation evaluation result, the variable parameter value selection simulation analysis unit 62 sets, for example, the time when a predetermined time T has elapsed from the start of the item selection simulation as a start hour T, and calculates an integral value of the yield of the objective substance A from the start hour T to the hour (T+Δt) as the item selection simulation evaluation result on the basis of the item selection simulation result.

In a next step S72, the variable parameter value selection simulation analysis unit 62 newly selects a candidate dissolution amount from within the search range and decides whether to continue the processing of performing a variable parameter value selection simulation. In the step S72, when the variable parameter value selection simulation analysis unit 62 decides to continue the variable parameter value selection simulation (Yes), that is, when the manager decides to continue the variable parameter value selection simulation, or the variable parameter value selection simulation analysis unit 62 decides that the variable parameter value selection simulation has not been executed a predetermined number of times, or the variable parameter value selection simulation analysis unit 62 decides that a desired variable parameter value selection simulation evaluation result group has not been obtained, the variable parameter value selection simulation analysis unit 62 returns to the above-described step S70, randomly selects the candidate dissolution amount from within the search range, and performs the variable parameter value selection simulation again.

As described above, a plurality of combination candidates are generated in which the dissolution amounts of m kinds of raw materials are different from each other, a variable parameter value selection simulation is performed for each combination candidate, and an integral value of the yield of the objective substance A is calculated for each combination candidate as a variable parameter value selection simulation evaluation result.

On the other hand, in the step S72, when the variable parameter value selection simulation analysis unit 62 decides not to continue the variable parameter value selection simulation (No), that is, when the manager decides not to continue the variable parameter value selection simulation, or the variable parameter value selection simulation analysis unit 62 decides that the variable parameter value selection simulation has been executed a predetermined number of times, or the variable parameter value selection simulation analysis unit 62 decides that a desired variable parameter value selection simulation evaluation result group has been obtained, the variable parameter value selection simulation analysis 62 proceeds to a next step S73.

In the step S73, for example, the variable parameter value analysis unit 1601 obtains a distribution tendency of the candidate variable parameter values and the variable parameter value selection simulation evaluation results on the basis of the variable parameter value selection simulation evaluation result, and limits the range of the dissolution amount in the search range of each raw material from this distribution tendency. In a next step S74, the variable parameter value selection unit 1602 selects the variable parameter value (dissolution amount) of each raw material from the range of the variable parameter value limited on the basis of the distribution tendency of the variable parameter values and the variable parameter value selection simulation evaluation results, generates a plurality of execution procedures with different dissolution amounts of each raw material of the variable parameter item, and ends the above-mentioned variable parameter value setting processing procedure.

A method for limiting the range of the variable parameter value from the result of a variable parameter value selection simulation and selecting the variable parameter value from within the limited range is not particularly limited; however, it is desirable to analyze the variable parameter value selection simulation evaluation result and the like, and to select a variable parameter value with which it can be expected to obtain an optimal evaluation result.

Here, 63A in FIG. 52 illustrates, in order to simplify the description, a schematic view of imaging the distribution tendency of the candidate variable parameter values and the variable parameter value selection simulation evaluation results when a variable parameter value selection simulation is performed by using two types of variable parameter items (raw materials) and changing the candidate variable parameter value (candidate dissolution amount) for each variable parameter item, and a result assuming how much yield of the objective substance A can be expected as each variable parameter selection simulation evaluation result.

Here, 63A in FIG. 52 is an example in which, for example, a candidate dissolution amount of a first raw material a1 in the variable parameter value selection simulation is represented on a horizontal axis, a candidate dissolution amount of a second candidate raw material b1 is represented on a vertical axis, and each obtained variable parameter value selection simulation evaluation result is color-coded. From the distribution tendency of such a variable parameter value selection simulation evaluation result, the range of the variable parameter value that is estimated to be optimal is narrowed, and from the narrowed range of the variable parameter value, the variable parameter value (dissolution amount) of each raw material specified in the execution procedure is selected.

Here, the variable parameter value analysis unit 1601 may generate a regression model by setting the candidate dissolution amount of each raw material used for the variable parameter value selection simulation as an explanatory variable and setting the variable parameter value selection simulation evaluation result as an objective variable, may limit the optimal range of the dissolution amount of the raw material on the basis of an analysis result of this regression model, and may select the variable parameter value from within the limited range.

In this case, the variable parameter value analysis unit 1601 may generate a regression model by, for example, using previous execution performance results and execution results (dissolution amount) stored in the database 8 as an explanatory variable, in addition to setting the candidate dissolution amount of each raw material used in the variable parameter value selection simulation as an explanatory variable, and setting the evaluation performance result or the evaluation result (yield) of the execution performance result and the variable parameter value selection simulation evaluation result as objective variables, may limit the optimal range of the dissolution amount of the raw material on the basis of an analysis result of this regression model, and may select the variable parameter value from the limited range.

Here, a variable parameter value selection simulation is executed, the range of the variable parameter value (dissolution amount) of the raw material in which the yield change of the objective substance A increases is limited, and on the basis of this, the variable parameter value of the raw material is selected; however, the invention is not limited to this.

As another embodiment, for example, a machine learning model (regression model) such as a neural network may be learned by using the input and output of the variable parameter value selection simulation as learning data, a learned regression model capable of differentiating the output with the input may be obtained, it may be arranged to obtain an analysis result approximating the variable parameter value selection simulation even with the learned regression model, and the optimal range of the variable parameter value may be limited by the regression model a.

In this case, it is desirable that such a learned regression model a is stored in advance in the database 8. As a result, when the dissolution amount of each raw material in which the yield change of the objective substance A increases is limited, the variable parameter value analysis unit 1601 can limit the optimal range of the dissolution amount of the raw material by using the learned regression model a, without executing the variable parameter value selection simulation.

In the case of using the learned regression model a, the burden of the arithmetic processing can also be reduced as compared to the variable parameter value selection simulation, an analysis result approximating the variable parameter value selection simulation evaluation result can be obtained in a shorter period of time than the variable parameter value selection simulation, and the search for the dissolution amount set as the variable parameter value can be performed efficiently by using the simulation.

When the regression model a is learned, the machine learning model (regression model a) may be learned by using not only the input and output of the variable parameter value selection simulation but also the execution performance result, evaluation performance result, and the like recorded in the database 8 as the learning data.

As still another embodiment, the range of the variable parameter value may be limited by using a regression model b as described below. For example, a learned regression model a for extracting a characteristic hyper parameter value, which is obtained by converting the variable parameter value (dissolution amount of the raw material), as a feature amount, is generated by using the input and the output of the variable parameter value selection simulation as learning data.

Next, a final regression model b may be generated by setting previous execution performance results (raw materials of a previously used culture medium M) or previous evaluation performance results (yield of the objective substance A at that time) as an explanatory variable and the evaluation performance results as an objective variable, with reference to the feature amount such as a hyper parameter value extracted from this learned regression model a.

Generating the final regression model b with reference to the feature amount such as a hyper parameter value extracted from the learned regression model a is, for example, as follows.

1. Here, in a regression model f (x/w), a d-dimensional vector x is taken as input. In addition, it is considered that there are k units (integer of 1≤k) of a weight variable w.
2. When the regression model of the above-described section 1 performs regression with respect to data, it is implied that i units (integer of 1≤i≤k) among k units of the weight variable w are updated such that the output of the regression model fits the data (for example, the weight of the regression model approximating the input and the output of the variable parameter value selection simulation is sought).
3. As a method for transitioning the feature amount of the regression model a obtained in the above-described section 2 into the other regression model b (in a case of transplanting the knowledge of the regression model a learned to approximate the input and the output of the variable parameter value selection simulation, into the final regression model b used to actually select the variable parameter value, or the like), there are broadly the following two patterns (1) and (2). For example, in a case where the regression model a and the final regression model b are applied in the same function form,
   (1) some or all of k units of the weight variable of the regression model a after learning are substituted for the corresponding weight variable of the final regression model b; and
   (2) one or more relational expressions or inequations such as c(w)=0 or c(w)>0, which are established between k units of the weight variable of the regression model a, are extracted (or created by the manager), and it is arranged such that the weight variable w of the final regression model b also similarly satisfies the relationship (during learning).

In addition, in a case where the regression model a and the final regression model b are not applied in the same function form, it is possible to transition the feature amount of the regression model a into the other regression model b by a method of training the final regression model b so as to approximate the input and the output of the regression model a.

The variable parameter value analysis unit 1601 can limit the range of the dissolution amount of the raw material in which the yield change of the objective substance A increases, by using the final regression model obtained as described above.

Here, a simpler example of the case of generating the final regression model b with reference to the feature amount extracted from the above-mentioned learned regression model a will be described below by using 63B, 63C, 63D, 63E in FIG. 52.

63B, 63C, and 63D in FIG. 63 are schematic views in which, for example, two raw materials are specified as variable parameter items, a search range ER1 of each variable parameter value specified in the template execution procedure is imaged, and the feature amount extracted from the learned regression model a by utilizing the variable parameter value selection simulation evaluation result is imaged as regions ER2, ER3, and ER4. In this case, by explicitly describing the constraint condition (there is neither an unknown nor a degree of freedom), the search range ER1 can be limited similarly to the regions ER2, ER3, and ER4, and this can be extracted as a feature amount.

For example, 63E in FIG. 52 is a schematic view showing that the search range is not limited to a region that can be explicitly written down as 63D, and one or more unknowns or degrees of freedom may be provided. In 63D, the narrowed search range is uniquely identified; however, in 63E, the search range itself is characterized by an unknown c. When search is actually performed, for example, the search range characterized by this unknown c is described in the regression model b for generating the variable parameter value to be actually executed, and consequently there is an effect of limiting the search range.

(2-3) Functions and Effects

In the configuration described above, even in the culture-related process optimization method according to the second embodiment, as with the first embodiment, execution procedures of the culture-related process and the evaluation process thereof, execution schedules that are data indicating at what timing each execution subject should collaboratively perform each operation in the execution procedure, and execution instruction information that instructs the execution subject in the execution environment 100 to execute each corresponding operation in accordance with the execution schedule, are generated by the culture-related process optimization processing. Therefore, in the culture-related process optimization method according to the second embodiment as well, the same effects as those of the first embodiment can be obtained.

Furthermore, in the culture-related process optimization method according to the second embodiment, a parameter value for item selection (dissolution amount) of a candidate variable parameter item (candidate raw material) that can be a variable parameter item assumed to obtain a predetermined evaluation result is selected, an item selection simulation in which the parameter value for item selection of the selected candidate raw material is set as input and the evaluation result (yield change of the objective substance) is set as output is executed by arithmetic processing, and the variable parameter item is limited in advance on the basis of the result of the item selection simulation (variable parameter item identification step). As a result, in the second embodiment, since narrowing of the raw materials for composing a culture medium M that can maximize the yield of the objective substance A, from among several hundred types of candidate raw materials for composing the culture medium M, can be performed in advance, the number of times of the execution procedure to be actually performed in the execution environment 100 can be drastically cut down.

In the culture-related process optimization method according to the second embodiment, a candidate variable parameter value (candidate raw material) assumed to obtain a predetermined evaluation result is selected, a variable parameter value selection simulation in which the selected candidate variable parameter value is set as input and the evaluation result (yield change of the objective substance) is set as output is executed by arithmetic processing, and the range of the variable parameter value is limited in advance on the basis of the result of the variable parameter value selection simulation (variable parameter value identification step). As a result, in the second embodiment, since narrowing of the range of the dissolution amount of a raw material that is considered to maximize the yield of the objective substance A, for the raw materials for composing the culture medium M, can be performed in advance, the number of times of the execution procedure to be actually performed in the execution environment 100 can be drastically cut down.

As an example of the variable parameter value identification step, a learned regression model capable of differentiating the output with the input may be generated by using the input and the output of the variable parameter value selection simulation as learning data, and the range of the variable parameter value may be limited on the basis of this learned regression model. As a result, an analysis result approximating the variable parameter value selection simulation evaluation result is obtained in a shorter time than the variable parameter value selection simulation, and the search of the variable parameter value can be performed efficiently.

Furthermore, as an example of the variable parameter value identification step, a learned regression model for extracting the feature amount according to a change in the candidate variable parameter value may be generated by using the input and the output of the variable parameter value selection simulation as learning data, a final regression model using the feature amount extracted from this learned regression model may be generated, and the range of the variable parameter value may be limited on the basis of this final regression model.

As described above, in the culture-related process optimization method, since the variable parameter item of the template execution procedure or the variable parameter value of the execution procedure can be limited to some extent by the item selection simulation and the variable parameter value selection simulation, the number of times of the execution procedure to be actually performed in the execution environment 100 can be drastically cut down.

Particularly, in the culture-related process in which there are many hidden variables and the execution environment 100 is a complicated system, as with a bioplant, it is effective to reduce the number of times of search for the execution subject to search for an optimal production condition by the execution procedure in the execution environment 100, by using the item selection simulation and the variable parameter value selection simulation.

In the culture-related process optimization method according to the second embodiment, a culture-related process for producing a compound A by culturing *Escherichia coli* X in a culture medium M to induce expression of an enzyme P has been described as an example, and it is obvious that the culture-related process optimization method can be applied to other cell culture-related processes according to the above-mentioned embodiment.

(3) Regarding Search in Relevant Execution Procedure

Subsequently, a culture-related process optimization method related to a third embodiment will be described. In the above-described embodiments, an execution performance result and an evaluation performance result of a relevant execution procedure are searched and acquired from the database 8 on the basis of the terms specified in the operation item 26*a* in the starting point execution procedure; however, in the present embodiment, a broader search is executed. For example, the execution performance result and the evaluation performance result of a relevant execution procedure may be searched and acquired from the database 8 on the basis of the terms specified for an operation item 26*a* in a starting point execution procedure as well as for any one of an input item 26*b*, an output item 26*c*, an execution parameter item 26*d*, and a constraint condition item 26*e*.

In addition to a search according to simple identity of terms, for example, matters relevant to the type, property, identification, component, composition, breed variety, gene, homology, production conditions, and the like may be set in advance with respect to: (i) a technical treatment/processing method such as a culturing method, a heating method, a cooling method, a molding method, a compressing method, or a sorting method; (ii) the processing target of an operation, such as a basal culture medium or a raw material; (iii) an outcome obtained by an operation, such as a differentiation-inducing culture medium (adjusted), an objective substance, or a molded article; and (iv) an evaluation method such as qualitative quantitative evaluation, appearance evaluation, moldability evaluation, or quality evaluation, as specified for at least the operation item 26*a*, the input item 26*b*, the output item 26*c*, the execution parameter item 26*d*, and the constraint condition item 26*e* in the starting point execution procedure, and on the basis of these matters set in advance, the execution performance result and the evaluation performance result of the relevant execution procedures may be searched and acquired from the database 8.

For example, when the starting point execution procedure of the "Cell using differentiation-inducing culture medium B" shown in FIG. 2 is taken as an example, (i) an execution performance result and an evaluation performance result of a culture medium similar in terms of a component or a type to a differentiation-inducing culture medium B specified for the input item 26*b* of the starting point execution procedure, a culture medium similar in terms of a component to the differentiation-inducing culture medium B, or the like; (ii) an execution performance result and an evaluation performance result similar to the result of the marker gene expression evaluation specified for the output item 26*c* in the evaluation process of the starting point execution procedure; (iii) an execution performance result and an evaluation performance result of a culturing method similar to the culturing method specified for the execution parameter item 26*d* of the starting point execution procedure, an approximate culturing temperature, a culturing time, an approximate evaluation index, or the like; and (iv) an execution performance result and an evaluation performance result in a predetermined range such as the time constraint, the execution condition constraint, or the like specified for the constraint condition item 26*e* of the starting point execution procedure, may be searched and acquired from the database 8 as the execution performance result and the evaluation performance result of the relevant execution procedure.

In addition, an execution performance result and an evaluation performance result in which the same terms as the culture medium, the composition, the gene, the strain, the culturing method, the culturing procedure, the culture temperature, and the culture time, specified for the operation item 26a, the input item 26b, the output item 26c, the execution parameter item 26d, or the constraint condition item 26e of the starting point execution procedure are included, are searched and acquired from the database 8 as the execution performance result and the evaluation performance result of the relevant execution procedure. In addition to the search according to the simple identity of terms, these matters and matters relevant to the composition, breed variety, gene, homology, production conditions, and the like may be set in advance, and on the basis of these matters set in advance, the execution performance result and the evaluation performance result of the relevant execution procedure may be searched from the database 8.

(4) Culture-Related Process Optimization Method Related to Fourth Embodiment

Figure 53:
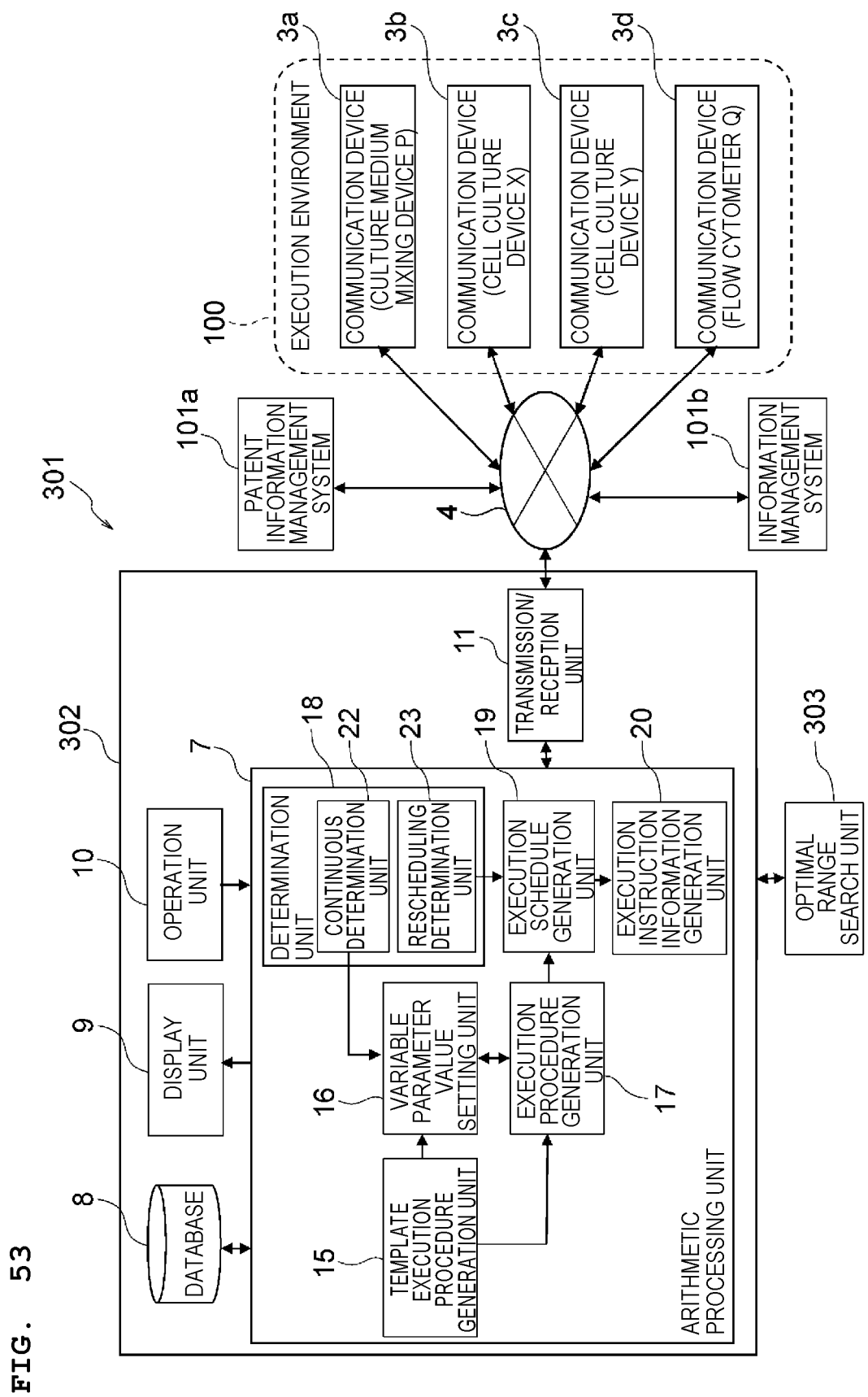
FIG. 53 is a block diagram illustrating an overall configuration of a culture-related process optimization system according to a fourth embodiment.

(4-1) Outline of Culture-Related Process Optimization Method Related to Fourth Embodiment Next, a culture-related process optimization method according to a fourth embodiment will be described. FIG. 53 is a block diagram illustrating the overall configuration of a culture-related process optimization system 301 that executes the culture-related process optimization method according to the fourth embodiment. As shown in FIG. 53, this culture-related process optimization system 301 is different from the above-described first embodiment from the viewpoint that the culture-related process optimization device 302 is provided with an optimal range search unit 303, and that a patent information management system 101a and an information management system 101b are connected to the culture-related process optimization device 302 through a network 4. In order to avoid repetition of explanation, the description on the same configuration as the first embodiment will not be repeated, and the description will be focused on the differences from the first embodiment.

To the culture-related process optimization device 302, for example, a patent information management system 101a and an information management system 101b such as patent information platforms (J-PlatPat (registered trademark)), foreign patent information services (FOPISER), Espacenet (registered trademark), and PATENTSCOPE (registered trademark), in which patent publications (publications showing the contents of patent applications granted rights after examination by Patent Offices), publication of patent applications (publications showing the contents of patent applications before being granted rights), and the like are stored, are connected through a network 4. In this case, when the culture-related process optimization device 302 receives a predetermined patent information acquisition command from the manager (user) through an operation unit 10 in order to acquire predetermined patent publication or publication of patent applications, the patent acquisition command is transmitted from a transmission/reception unit 11 to a patent information management system 101a through the network 4.

As a result, the patent information management system 101a reads out a predetermined patent publication or publication of patent application from the database in accordance with the patent information acquisition command, and transmits this as patent publication data to the culture-related process optimization system 301 through the network 4. The culture-related process optimization system 301 receives the patent publication data transmitted from the patent information management system 101a in accordance with the patent information acquisition command, through the transmission/reception unit 11 and stores the patent publication data in the database 8. The culture-related process optimization device 302 displays the acquired patent publication data on a display unit 9 and allows the manager to visually recognize the contents of the patent publication or publication of patent application on the basis of the patent publication data.

In addition, the culture-related process optimization device 302 can acquire various culture-related technical information such as, for example, a culture medium, cells cultured in the culture medium, a culture medium adjustment process showing a method for adjusting the culture medium, and a cell culture process showing a method for culturing cells, as necessary, from the information management system 101b connected through the network 4 in accordance with an operation command from the operation unit 10. In this way, the culture-related process optimization device 302 can acquire patent publication data and other various technical information as an existing condition through the network 4.

Here, the technical information other than the patent publication data, which can be acquired by the culture-related process optimization device 302 as an existing condition, include known technical information as well as unknown technical information. Specifically, as the technical information, for example, academic articles, textbooks, experimental notes, product specifications, technical information listed on websites, and technical information collected and created by specific people can be applied. In the present embodiment, for example, a case in which patent publication data, which is a patent publication recognized as rights after examination by the Patent Office, is acquired as an existing condition, will be mainly described.

In this case, when the culture-related process optimization device 302 acquires the patent publication data as the existing condition, the culture-related process optimization device 302 allows the optimal range search unit 303 to search for an optimal range of a variable parameter value that can generate an execution procedure that avoids the existing condition. Specifically, the optimal range search unit 303 searches for an optimal range of a variable parameter value that can generate an execution procedure that is outside the range of the existing condition, the execution procedure not satisfying at least one or more constituent features among a plurality of constituent features included in the existing condition, from within the search range of the variable parameter value specified on the basis of the starting point execution procedure, previous execution performance results and evaluation performance results, and the like.

For example, with regard to a patent publication, technical matters for which the scope of rights is specified by the contents of the claims described in the patent claims in the patent publication, and a plurality of constituent features described in the claims are all satisfied, fall in principle under patent infringement.

In the culture-related process optimization device 302 according to the fourth embodiment, an optimal range of a variable parameter value that can generate a template execution procedure that is outside the scope of patent rights, the template execution procedure not satisfying at least one or more constituent features among a plurality of constituent features specified in the claims of a patent publication, is identified by executing the optimal range search processing, and an execution procedure which obtains an optimal evaluation result having a gain as large as possible for the culture-related process and avoids existing conditions, is sought by trial and error. Particularly, in a case where a patent publication is selected as an existing condition as described above, an execution procedure which obtains an optimal evaluation result having a gain as large as possible for the culture-related process and does not infringe on patent rights, can be sought, and on the other hand, in a case where the manager selects a known/unknown culture-related process that is wished to be avoided, as an existing condition, a new execution procedure which obtains an optimal evaluation result having a gain as large as possible for the culture-related process and avoids the known/unknown culture-related process, can be sought.

(4-2) Optimal Range Search Processing

Figure 54:
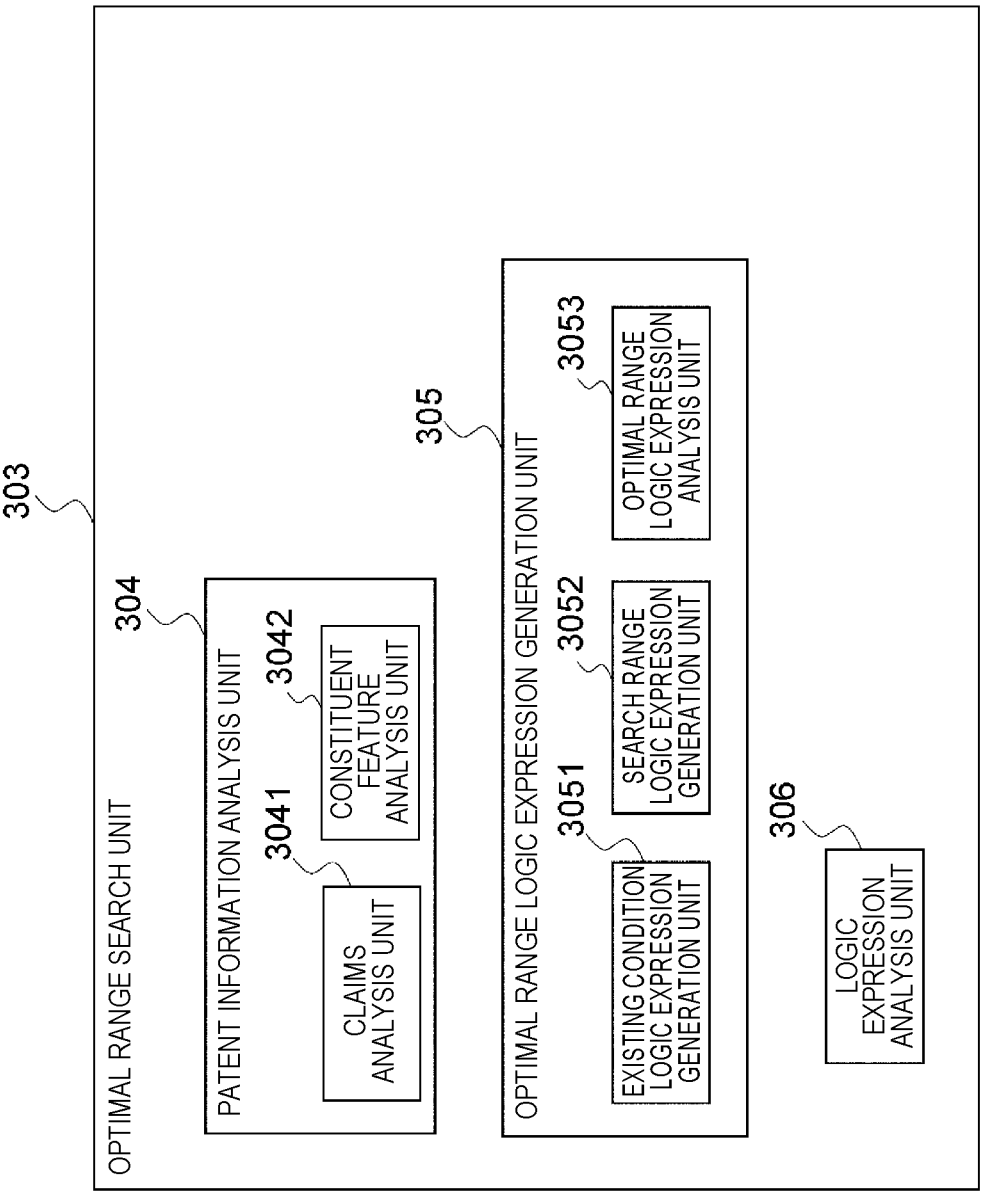
FIG. 54 is a block diagram illustrating a configuration of an optimal range search unit.
Figure 55:
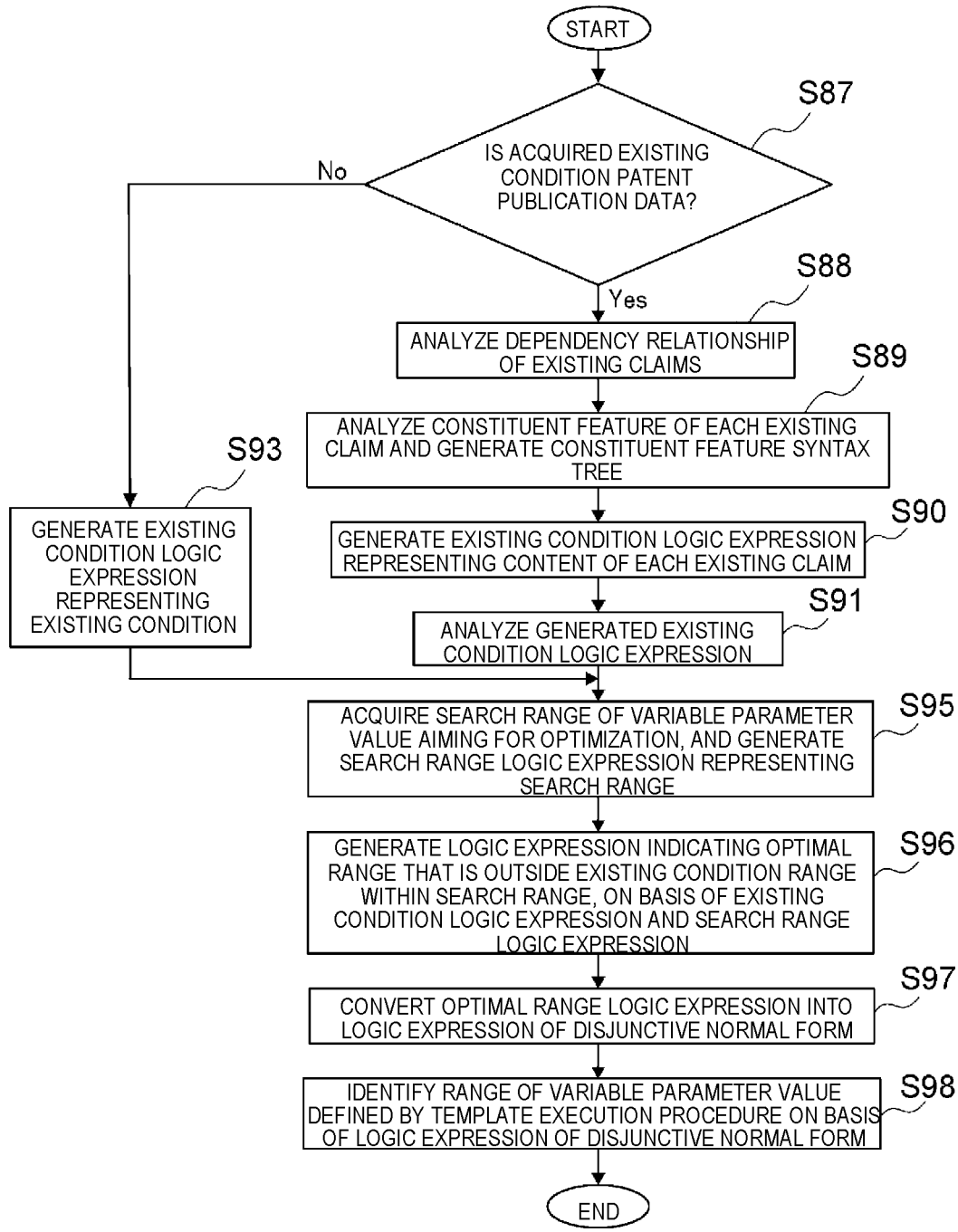
FIG. 55 is a flow chart illustrating an optimal range search processing procedure.

Next, the above-mentioned optimal range search processing will be described. FIG. 54 is a block diagram illustrating the configuration of the optimal range search unit 303. In addition, FIG. 55 is a flowchart illustrating an optimal range search processing procedure that is executed by the culture-related process optimization device 302. As shown in FIG. 54, the optimal range search unit 303 includes a patent information analysis unit 304, an optimal range logic expression generation unit 305, and a logic expression analysis unit 306. Furthermore, the patent information analysis unit 304 includes a claims analysis unit 3041 and a constituent feature analysis unit 3042, and the optimal range logic expression generation unit 305 includes an existing condition logic expression generation unit 3051, a search range logic expression generation unit 3052, and an optimal range logic expression analysis unit 3053.

In this when the culture-related process optimization device 302 acquires an existing condition from an external system or the like through the network 4, as shown in FIG. 55, the culture-related process optimization device 302 starts an optimal range search processing procedure from a start step and proceeds to a next step S87. In the step 87, the optimal range search unit 303 decides whether the acquired existing condition is patent publication data. Whether the acquired existing condition is patent publication data may be decided, for example, on the basis of whether the acquisition source of the acquired existing condition is the patent information management system 101a, or may be decided on the basis of whether the characters "patent publication" or "publication of patent application" are included in the existing condition, and furthermore, the decision result that the existing condition is patent publication data may be decided by inputted by the manager through the operation unit 10.

Here, when an affirmative result is obtained in the step S87, this indicates that the acquired existing condition is patent information data, and in this case, the patent information analysis unit 403 of the optimal range search unit 303 allows the claims analysis unit 3041 to analyze the dependency relationships of the claims that are included in the patent publication data and are to be analyzed (hereinafter, referred to as existing claims), in a next step S88. Here, a case of applying a patent publication after patent prosecution, in which the contents of the existing claims are as follows, will be described as an example of the patent publication data.

"Existing Claim 1

A culture medium for mesenchymal stem cells, comprising:
bone morphogenetic protein-4 (hereinafter, referred to as BMP4) at a concentration of less than 5 μM;
vascular endothelial growth factor (hereinafter, referred to as VEGF) at a concentration of less than 5 μM; and/or
stem cell growth factor (hereinafter, referred to as SCF (Stem Cell Factor) at a concentration of 5 μM or greater and less than 10 μM."

"Existing Claim 2

The culture medium for mesenchymal stem cells according to the existing claim 1, further comprising a saccharide at a concentration of less than 5 μM."

"Existing Claim 3

The culture medium for mesenchymal stem cells according to the existing claim 1 or 2, further comprising substance K."

"Existing Claim 4

The culture medium for mesenchymal stem cells according to the existing claim 3, wherein the substance K is included at a concentration of less than 5 μM."

In this case, in the claims analysis unit 3041, for example, information on the format specified in advance by the Patent Office for patent application documents consisting of the patent claims, the specification, and the like, the dependency relationship analysis information on general formats and terms used when indicating the dependency relationships of the existing claims in the patent claims, and the like are stored in advance. The claims analysis unit 3041 extracts the information of the patent claims from the patent publication data, analyzes the stated contents of Existing Claims 1 to 4 by using the dependency relationship analysis information and known natural language processing technologies (for example, Cited Reference 1: Sheremetyeva, S., Nirenburg, S., & Nirenburg, I. (1996). Generating patent claims from interactive input. In Eighth International Natural Language Generation Workshop (https://www.researchgate.net/publication/2480091_Generating_Patent_Claims_From_Interactive_Input), Cited Reference 2: Sheremetyeva, S. (2003 July). Natural language analysis of patent claims. In Proceedings of the ACL-2003 workshop on Patent corpus processing (pp. 66-73). (https://aclanthology.org/W03-2008.pdf)), and identifies the dependency relationships among the existing claims 1 to 4, such as whether each of the existing claims 1 to 4 is an independent claim that is independent with no statement of dependency, or to which claim a dependent claim is subordinate. The claims analysis unit 3041 generates a claim syntax tree in which the dependency relationships of the existing claims 1 to 4 are structured, such as a tree structure in which an existing claim on the side that is subordinate to another claim is a parent while an existing claim to which another claim is subordinate is a child, and a directed acyclic graph (DAG).

Figure 56:
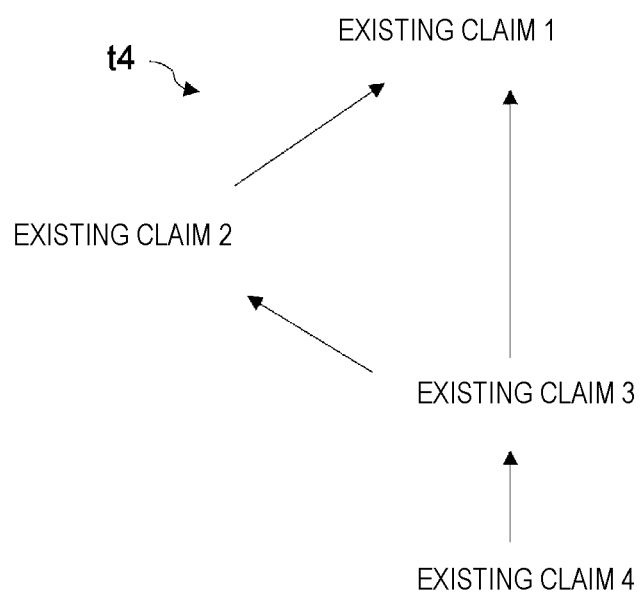
FIG. 56 is a schematic view illustrating an example of a claim syntax tree generated based on existing claims 1 to 4.

FIG. 56 shows an example of the claim syntax tree generated by the claims analysis unit 3041 on the basis of existing claims 1 to 4. In this example, existing claim 1 is specified as a parent on the basis of the description of the claims, existing claim 2 is specified as a child of the existing claim 1, existing claim 3 is specified as a child of these existing claims 1 and 2, and existing claim 4 is specified as a child of the existing claim 3.

As described above, when the dependency relationships are analyzed for the existing claims 1 to 4, in a next step S89, the constituent feature analysis unit 3042 divides the stated contents into a plurality of constituent features for each of the existing claims 1 to 4, and analyzes the relevancy between the constituent features on the basis of, for example, terms such as", (punctuation mark)", "and", and "or" in the text. For example, the constituent feature analysis unit 3042 defines in advance the terms expressing the relevancy between the constituent features, analyzes the stated contents of each of the existing claims 1 to 4 by using this definition information and known natural language processing technologies (for example, Cited Reference 3: Shinmori, A., Okumura, M., Marukawa, Y., & Iwayama, M. (2003 July), Patent claim processing for readability-structure analysis and term explanation. In Proceedings of the ACL-2003 workshop on Patent corpus processing (pp. 56-65). (https://aclanthology.org/W03-2007.pdf)), and generates a constituent feature syntax tree representing the relevance between the constituent features in a tree structure or the like for each of individual existing claims 1 to 4.

Figure 57:
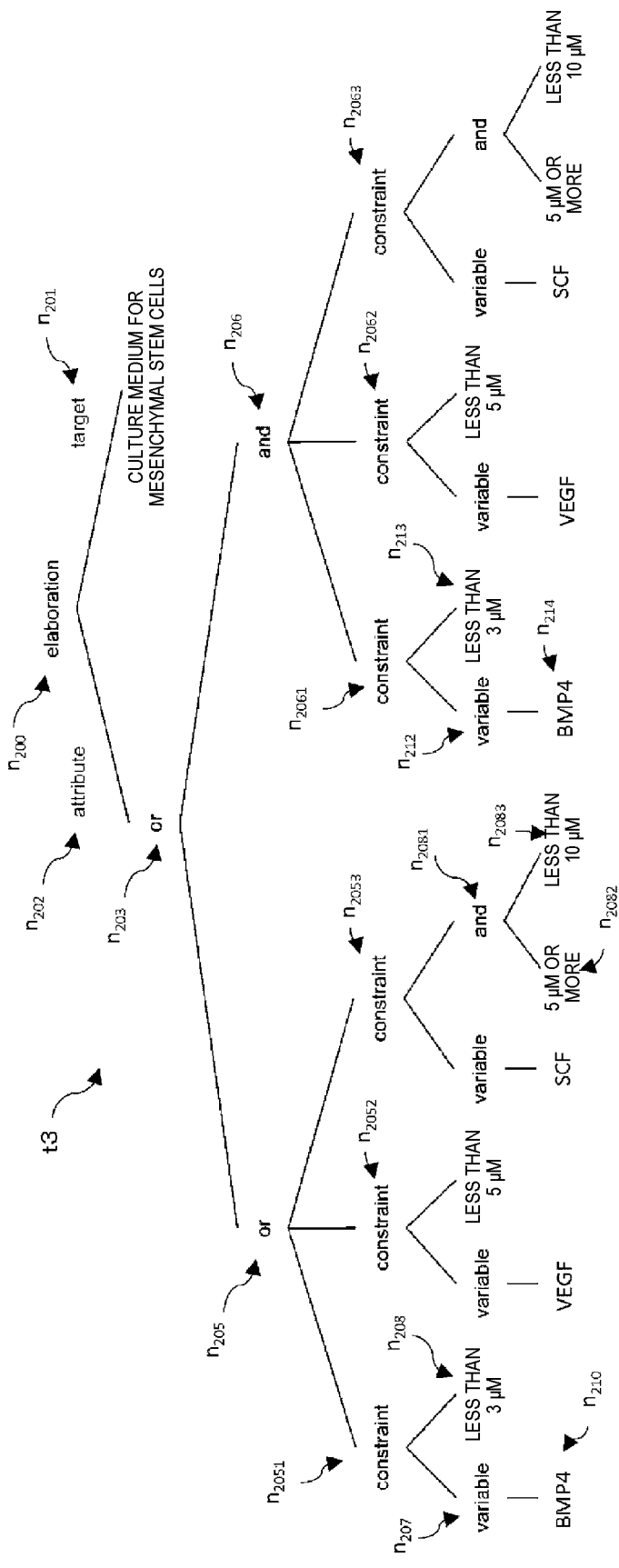
FIG. 57 is a schematic view illustrating an example of a constituent feature syntax tree generated on the basis of contents of the existing claim 1.

Here, FIG. 57 is a schematic view illustrating the configuration of a constituent feature syntax tree generated from the existing claim 1 by the constituent feature analysis unit 3042. Here, the existing claim 1 can be divided into a constituent feature of "including BMP4 at a concentration of less than 3 µM", a constituent feature of "including VEGF at a concentration of less than 5 µM", a constituent feature of "including SCF at a concentration of 5 µM or greater and less than 10 µM", and a constituent feature of "a culture medium for mesenchymal stem cells", from the terms such as ", (punctuation mark)" and "and/or" in the text.

Furthermore, from the terms such as ", (punctuation mark)" and "and/or" in the text of the existing claim 1, the scope of rights of the existing claim 1 covers the following four forms of "culture medium for mesenchymal stem cells".

(i) "Culture medium for mesenchymal stem cells, including BMP4 at a concentration of less than 3 µM"
(ii) "Culture medium for mesenchymal stem cells, including VEGF at a concentration of less than 5 µM"
(iii) "Culture medium for mesenchymal stem cells, including SCF at a concentration of 5 µM or greater and less than 10 µM"
(iv) "Culture medium for mesenchymal stem cells including all of BMP4 at a concentration of less than 3 µM, VEGF at a concentration of less than 5 µM, and SCF at a concentration of 5 µM or greater and less than 10 µM"

The constituent feature of an existing claim in the present specification indicate requirements represented by terms such as nouns, numerical values, and units, as with the substances, synthesis method, site, position, direction, time, quantity, concentration, temperature, pressure, and the like specified in the existing claim, and also indicate requirements represented by sentences in which a plurality of these terms are linked to have one meaning. For example, in a case where the above-described existing claim 1 is taken as an example, the constituent features consisting of terms include terms such as "culture medium for mesenchymal stem cells", "BMP4", "less than 3 µM", "VEGF", "less than 5 µM", "SCF", "5 µM or greater", "less than 10 µM". In addition, the constituent features consisting of a sentence having one meaning include sentences such as "includes BMP4 at a concentration of less than 3 µM", "includes VEGF at a concentration of less than 5 µM", "includes SCF at a concentration of 5 µM or greater and less than 10 µM", and "includes all of BMP4 at a concentration of less than 3 µM, VEGF at a concentration of less than 5 µM, and SCF at a concentration of 5 µM or greater and less than 10 µM".

The constituent feature analysis unit 3042 analyzes the constituent features of the existing claim 1 and the relevancy between each of the constituent features on the basis of the definition information of terms such as ", (punctuation mark)" and "and/or" in the text of the existing claim 1, or terms representing the relevancy between the constituent features, and known natural language processing technologies, identifies the constituent features on a term-by-term basis or a sentence-by-sentence basis such as described above, and generates a constituent feature syntax tree (FIG. 57) representing the relevancy between these constituent features.

In this case, the constituent feature analysis unit 3042 provides an elaboration node $n_{200}$ that serves as a starting point, provides a target node $n_{201}$ and an attribute node $n_{202}$ as children of the elaboration node $n_{200}$, and links each of the target node $n_{201}$ and the attribute node $n_{202}$ to the elaboration node $n_{200}$ through an edge. The constituent feature analysis unit 3042 extracts the noun "culture medium for mesenchymal stem cells", which is the "Title of Invention" at the end of line of the existing claim 1, associates the noun with the target node $n_{201}$, analyzes "/" in "and/or" that divides the existing claim 1 into the above-described four forms, and associates "or", which indicates that it is sufficient to satisfy any one of the constraints specified by the children, with the attribute node $n_{202}$.

As a child of the attribute node $n_{203}$ of "or" representing the relevancy between "and" and "or" of "and/or" in the existing claim 1, the constituent feature analysis unit 3042 provides a node $n_{205}$ of "or" representing "or", which implies that it is sufficient to satisfy any one of the constraints specified by the children, and a node $n_{206}$ of "and" representing "and", which implies that it is necessary to satisfy all of the constraints specified by the children, in the term "and/or" indicating the relevancy between constituent features on a sentence-by-sentence basis, and links these to the attribute node $n_{203}$ through edges.

The constituent feature analysis unit 3042 provides a plurality of constraint nodes $n_{2051}$, $n_{2052}$, and $n_{2053}$ respectively representing the contents of the constituent features divided by "or", as children of the node $n_{205}$ representing "or", which implies that it is necessary to satisfy any one of the constraints, and links these to the node $n_{205}$ through edges. Furthermore, the constituent feature analysis unit 3042 provides a variable node $n_{207}$ and a parameter node $n_{208}$ as children to each of the constraint nodes $n_{2051}$, $n_{2052}$, and $n_{2053}$, and links these to each of the constraint nodes $n_{2051}$, $n_{2052}$, and $n_{2053}$ through edges.

With regard to the constraint node $n_{2051}$ according to the present embodiment, a label of "BMP4" is linked to the variable node $n_{207}$ through an edge, a parameter such as "less than 3 µM" is associated with the parameter node $n_{208}$, and the constituent feature of "includes BMP4 at a concentration of 3 µM" of the existing claim 1 shown in the above-described section (i) is specified. With regard to the constraint node $n_{2052}$, a label of "VEGF" is linked to the variable node $n_{207}$ through an edge, a parameter such as "less than 5 µM" associated with the parameter node $n_{208}$, and the is constituent feature such as "including VEGF at a concentration of less than 5 µM" of the existing claim 1 shown in the above-described section (ii) is specified.

Furthermore, with regard to the constraint node $n_{2053}$, a label of "SCF" is linked to the variable node $n_{207}$ through an edge, and the parameter node $n_{208}$ is provided with a node $n_{2081}$ representing a logical product of "and". The node$_{2081}$ representing a logical product is provided with a lower limit value node $n_{2082}$ and an upper limit value node $n_{2083}$ as children, and these are linked by edges. The lower limit value node $n_{2082}$ is associated with a label of the lower limit value "5 µM or greater" of the parameter limited in the existing claim 1 for the "SCF" specified by the parent constraint node $n_{2053}$, and the upper limit value node $n_{2083}$ is associated with a label of the upper limit value "less than 10 µM" of the parameter limited in the existing claim 1 for the "SCF" specified by the same parent constraint node $n_{2053}$.

Similarly to the node $n_{205}$ representing "or", the other node $n_{206}$ representing "and", which is provided as a child of the attribute node $n_{203}$, is provided with the constraint nodes $n_{2061}$, $n_{2062}$, and $n_{2063}$ that needs to satisfy all the constraints, and these are linked through edges as children of the node $n_{206}$ representing "and". Here, the constraint nodes $n_{2061}$, $n_{2062}$, and $n_{2063}$ have the same contents as the constraint nodes $n_{2051}$, $n_{2052}$, and $n_{2053}$ specified by the above-mentioned node $n_{205}$ representing "or", and therefore, further description thereof will not be repeated.

The constituent feature analysis unit 3042 generates a constituent feature syntax tree also for the remaining existing claims 2 to 4, similarly to the existing claim 1. As described above, the constituent feature analysis unit 3042 analyzes the mutual relevancy of a plurality of constituent features respectively specified in each of the existing claims 1 to 4, and generates constituent feature syntax trees representing the mutual relevancy of the constituent features of the existing claims 1 to 4.

For the processing for generating a constituent feature syntax tree for each of these existing claims 1 to 4, for example, "Patent claim processing for readability: Structure analysis and term explanation (https://www.researchgate.net/publication/228569678_Patent_claim_processing_for_readability_Structure_analysis_and_term_explanation)", which is a known technology, can be applied.

In the present embodiment, a constituent feature syntax tree is separately generated for each of the existing claims 1 to 4, and as an example among them, the constituent feature syntax tree of the existing claim 1 has been described by using FIG. 57. However, the invention is not limited to this, and for example, the constituent feature syntax tree of the existing claim 2 or the like subordinate to the existing claim 1 may be integrated with the constituent feature syntax tree of the existing claim 1 such that the existing claims 1 to 4 are presented in one constituent feature syntax tree.

Next, in a step S90, the existing condition logic expression generation unit 3051 generates each existing condition logic expression representing the contents of each of the existing claims 1 to 4 on the basis of the constituent feature syntax trees generated for each of the existing claims 1 to 4. That is, the existing condition logic expression generation unit 3051 generates an existing condition logic expression representing a constituent feature syntax tree by using logical symbols used to represent logical representations in logic (for example, $\forall$, $\exists$, $\neg$, $\wedge$, $\vee$, $\rightarrow$, $\leftarrow$, and $\leftrightarrow$). Hereinafter, in order to simplify the description, the description will be focused on the existing claims 1 and 2, and the description on the existing claims 3 and 4 will not be repeated here. The existing condition logic expression of the existing claim 1 is the following Expression (1), and the existing condition logic expression of the existing claim 2 is the following Expression (2) (V is logical sum (or), and $\wedge$ is logical product (and)).

$$(BMP4<3 \, \mu M) \vee (VEGF<5 \, \mu M) \wedge (5 \, \mu M \leq SCF<10 \, \mu M) \wedge ((BMP4<3 \, \mu M) \wedge (VEGF<5 \, \mu M) \wedge (5 \, \mu M \leq SCF<10 \, \mu M)) \quad (1)$$

$$Saccharide<5 \, \mu M \quad (2)$$

Next, the constituent feature analysis unit 3042 proceeds to a step S91, analyzes the existing condition logic expression generated in the step S90, and generates an existing condition logic expression by converting the terms that are included in the existing condition logic expression into terms that are in the relationship of more specific concepts (here, also referred to as ontology). For example, in Expression (2) that is the existing condition logic expression of the existing claim 2, a new existing condition logic expression represented by the following Expression (3) is generated, in which the term "Saccharide" is converted into "Glucose" and "Trehalose" that are in the relationship of more specific concepts.

$$(Glucose<5 \, mM) \vee (Trehalose<5 \, \mu M) \quad (3)$$

Regarding the conversion into terms that are in such a relationship of more specific concepts, a substance that is in the relationship of more specific concepts of "Saccharide" may be identified by using definition information that defines in advance the relationship of more generic and more specific concepts, or a substance specified as a more specific concept of "Saccharide" may be searched and identified from the stated contents of the specification included in the patent publication data that is subjected to analysis. Here, a case in which terms specified in existing claims are converted into terms that are in the relationship of more specific concepts has been described; however, the invention is not limited to this, and the terms specified in existing claims may be converted into terms that are in the relationship of more generic concepts.

In addition to this, in the step S91, the existing condition logic expression generation unit 3051 analyzes each of the existing condition logic expressions of the existing claims 1 to 4, and associates dependency relationship to the existing condition logic expressions generated for each of the existing claims 1 to 4 on the basis of the dependency relationship of the existing claims 1 to 4 analyzed in the step S88. FIG. 58 illustrates an example f structured data in which the dependency relationship is associated with the existing condition logic expressions of the existing claims 1 to 4.

In this case, in the existing condition logic expression generation unit 3051, for example, since the existing claim 2 is subordinate to the existing claim 1 (existing claim 1$\wedge$existing claim 2 (in FIG. 58, described as "1$\wedge$2")), the existing condition logic expression of the existing claim 2, which is a dependent claim of the existing claim 1, is disposed adjacent to the existing condition logic expression of the existing claim 1 to which the existing claim 2 is subordinate. Furthermore, in the existing condition logic expression generation unit 3051, for example, since the existing claim 3 is respectively subordinate to the existing claim 2 that is a dependent claim of the existing claim 1, and to the existing claim 1 (existing claim 1$\wedge$existing claim 2$\wedge$existing claim 3 (in FIG. 58, described as "1$\wedge$2$\wedge$3"), and existing claim 1$\wedge$existing claim 3 (in FIG. 58, described as "1$\wedge$3")), also for the existing claim 3 which is a dependent claim of the existing claim 1 or 2, the existing condition logic expression of the existing claim 3 is disposed adjacent to the existing condition logic expressions of the existing claims 1 and 2 that make the existing claim 3 to be subordinate to each of the existing claim 1 and the existing claim 2.

As described above, the existing condition logic expression generation unit 3051 generates structured data showing a dependency pattern of each existing claim for each line with respect to the existing claims 1 to 4. The existing condition logic expression generation unit 3051 generates an existing condition logic expression (hereinafter, simply referred to as expression logic P) associating dependency relationships to the individual existing condition logic expressions of the existing claims 1 to 4, on the basis of the structured data as shown in the following Expression (4).

Logic expression $P$=existing condition logic expression of existing claim 1$\vee$ (existing condition logic expression of existing claim 1∧existing condition logic expression of existing claim 2)∨

(existing condition logic expression of existing claim 1∧existing condition logic expression of existing claim 2∧existing condition logic expression of exiting claim 3)∨

(existing condition logic expression of existing claim 1∧existing condition logic expression of existing claim 2∧existing condition logic expression of exiting claim 3∧existing condition logic expression of existing claim 4)∨

(existing condition logic expression of existing claim 1∧existing condition logic expression of exiting claim 3)∨

(existing condition logic expression of existing claim 1∧existing condition logic expression of existing claim 3∧existing condition logic expression of exiting claim 4)    (4)

Here, since the logic expression P taking all the existing claims 1 to 4 into consideration is complicated, in order to simplify the description, hereinafter, an example in which a logic expression P' obtained by using the existing claim 1 and the existing claim 2 is applied will be described. In this case, the logic expression P' is represented by the following Expression (5).

Logic expression $P'$=existing claim 1∨(existing claim 1∧existing claim 2)=

(Bmp 4<3 μM)∨(VEGF<5 μM)∨(5 μM≤SCF<10 μM)∨((BMP4<3 μM)∧(VEGF<5 μM)∧(5 μM≤SCF<10 μM))∨((BMP4<3 μM)∨(VEGF<5 μM)∨(5 μM≤SCF<10 μM)∨((BMP4<3 μM)∧(VEGF<5 μM)∧(5 μM≤SCF<10 μM))∧((Glucose<5 μM)∨(Trehalose<5 μM))    (5)

Next, proceeding to a step S95, the search range logic expression generation unit 3052 acquires a search range of a variable parameter value that is to be optimized, which has been generated in the template execution procedure generation unit 15 of the arithmetic processing unit 7, and generates a search range logic expression Q representing the search range by using the logical symbols used for presenting logical representations in logic.

When a negative result is obtained in the above-mentioned step S87, this indicates that the acquired existing condition is not patent information data, that is, neither a patent publication nor a publication of patent application, and that the existing condition is acquired from technical information such as books and academic articles, and in this case, the optimal range search unit 303 proceeds to a next step S93. In the step S93, the existing condition logic expression generation unit 3051 analyzes the acquired technical information to extract an existing condition to be analyzed from the technical information, generates an existing condition logic expression representing the existing condition, and proceeds to a next step S95. At this time, the technique for generating the existing condition logic expression representing the existing condition is not particularly limited, and for example, the manager may generate the existing condition logic expression, or an existing condition may be automatically extracted from the technical information by using a known natural language processing technology, and the existing condition logic expression may be generated.

Here, a case in which a patent publication after patent prosecution with the following contents of the existing claims is acquired (a case in which an affirmative result is obtained in the step S87) will be mainly described below. Furthermore, a case in which as the search range of the variable parameter value to be optimized, it is specified that BMP4 is 0 μM or greater and less than 10 μM, SCF is 0 μM or greater and 15 μM or less, and glucose is 10 μM or greater and 15 μM or less, will be described below as an example.

In this case, the search range logic expression generation unit 3052 generates the following Expression (6) as the search range logic expression Q on the basis of the above-described search range of the variable parameter value.

Search range logic expression $Q$=(0 μM≤BMP4≤10 μM)∧(0 μM≤SCF≤15 μM)∧(10 μM≤glucose≤15 μM)    (6)

Next, proceeding to a step S96, the optimal range logic expression analysis unit 3053 generates an optimal range logic expression R representing an optimal range that is within the search range of the variable parameter value and is outside the range of the existing condition, on the basis of the logic expression P' obtained in the step S91 and the search range logic expression Q obtained in the step S95. In the present embodiment, the following Expression (7) is determined from a logical symbol "¬" representing negation and a logical symbol "∧" representing a logical product, on the basis of the above-described logical expression P' (in order to simplify the description, converted to logical expression P, and here, logical expression P' is used) and the search range logic expression Q.

Optimal range logic expression $R$=¬$P'$∧$Q$=

¬((BMP4<3 μM)∨(VEGF<5 μM)∨(5 μM≤SCF<10 μM)∨((BMP4<3 μM)∧(VEGF<5 μM)∧(5 μM≤SCF<10 μM))∨(((BMP4<3 μM)∨(VEGF<5 μM)∨(5 μM≤SCF<10 μM)∨((BMP4<3 μM)∧(VEGF<5 μM)∧(5 μM≤SCF<10 μM))∧((glucose<5 μM)∨(trehalose<5M))))∧((0 μM≤BMP4≤10)∧(0 μM≤SCF≤15 μM)∧(10 μM≤glucose≤15 μM))    (7)

Next, in a step S97, the optimal range logic expression analysis unit 3053 converts the logic expression R obtained in the step S96 into, for example, an optimal range logic expression of disjunctive normal form. The optimal range logic expression of disjunctive normal form is a logic expression that is represented by R1∧R2∧ . . . ∧Rn (Ri=R'1∨ . . . ∨R'm), and a combination of parameters in which Ri (1≤i≤n) is true is not included in the scope of rights, and determines whether the combination of parameters is parameters within the search range of the variable parameter value.

Here, ¬P' can be represented by the following Expression (8).

¬$P'$=(¬$Ps$∧¬$Pp$∧¬$Pglt$)∨(¬$Ps$∧¬$Pp$∧¬$Pglt$∧¬$Pglc$∧¬$Pt$)

provided that $Ps$:BMP4<3 μM $Pp$:VEGF<5 μM $Pglt$:5 μM≤SCF<10 μM $Pglc$:glucose<5 μM $Pt$:trehalose<5 μM    (8)

The search range logic expression Q can be represented by the following Expression (9).

$Q$=$Qs$∧$Qglt$∧$Qglc$ provided that $Qs$: 0 μM≤BMP4≤10 μM $Qglt$: 0 μM≤SCF≤15 μM $Qglc$: 3 μM≤glucose≤15 μM         (9)

Expression (10) can be determined from the Expression (8) and the Expression (9).

$\neg P' \wedge Q = ((\neg Ps \wedge \neg Pp \wedge \neg Pglt) \vee (\neg Ps \wedge \neg Pp \wedge \neg Pglt \wedge \neg Pglc \wedge \neg Pt)) \wedge$ $(Qs \wedge Qglt \wedge Qglc) = R1 \vee R2$ provided that $R1=$
$(\neg Ps \wedge \neg Pp \wedge \neg Pglt \wedge Qs \wedge Qglt \wedge Qglc)$ $R2=$
$(\neg Ps \wedge \neg Pp \wedge \neg Pglt \wedge \neg Pglc \wedge \neg Pt \wedge Qs \wedge Qglt \wedge Qglc)$         (10)

As described above, when converted to the optimal range logic expression of disjunctive normal form (R1∨ ... ∨Rn; in the present embodiment, R1∨R2) in the step S97, the logic expression analysis unit 306 proceeds to a next step S98, extracts the range of the variable parameter value defined in the template execution procedure on the basis of the obtained optimal range logic expression of disjunctive normal form, and ends the optimal range search processing procedure.

In this case, in the step S98, in the logic expression analysis unit 306, the condition related to the parameter that is outside the search range of the variable parameter value (in this example, for example, Pp: VEGF<5 μM) in the optimal range logic expression of disjunctive normal form, is converted to be true. Furthermore, in each of R1 and R2 of the optimal range logic expressions of disjunctive normal form, the logic expression analysis unit 306 identifies a common part where the conditions of the range related to the parameters are common, and generates an optimal range logic expression excluding the identified common part. The following Expression (11) indicates an optimal range logic expression excluding the common part in R1 of the optimal range logic expression of disjunctive normal form, and the following Expression (12) indicates an optimal range logic expression excluding the common part in R2 of the optimal range logic expression of disjunctive normal form.

$R1 = (\neg Ps \wedge \neg Pp \wedge \neg Pglt \wedge Qs \wedge Qglt \wedge Qglc) \rightarrow (3$ μM≤BMP4≤10 μM)∧((0 μM≤SCF≤5 μM)∨(10 μM≤SCF≤15 μM))∧(3 μM≤glucose≤15 μM)         (11)

$R2=$
$(\neg Ps \wedge \neg Pp \wedge \neg Pglt \wedge \neg Pglc \wedge \neg Pt \wedge Qs \wedge Qglt \wedge Qglc)$
→(3 μM≤BMP4≤10 μM)∧((0 μM≤SCF≤5 μM)∨(10 μM≤SCF≤15 μM))∧(5 μM≤glucose≤15 μM)         (12)

In the logic expression analysis unit 306, the condition related to the parameter that is outside the search range of the variable parameter value in R1 of the optimal range logic expression of disjunctive normal form is converted to be true, and on the basis of the above-described Expression (11) excluding the common part, ranges of three parameters as shown in the following Expression (13) are obtained.

3 μM≤BMP4≤10 μM, (0 μM≤SCF≤5 μM)∨(10 μM≤SCF≤15 μM),

3 μM≤glucose≤15 μM         (13)

In the logic expression analysis unit 306, the condition related to the parameter that is outside the search range of the variable parameter value in R2 of the optimal range logic expression of disjunctive normal form is converted to be true, and on the basis of the above-described Expression (12) excluding the common part, ranges of three parameters as shown in the following Expression (14) are obtained.

3 μM≤BMP4≤10 μM (0 μM≤SCF≤5 μM)∨(10 μM≤SCF≤15 μM)

5 μM≤glucose≤15 μM         (14)

The logic expression analysis unit 306 compares the condition of the above-described Expression (13) determined from R1 of the optimal range logic expression of disjunctive normal form with the condition of the above-described Expression (14) determined from R2 of the optimal range logic expression of disjunctive normal form, and extracts the final range of the variable parameter value, in which the range of parameters included in the condition of the above-described Expression (13) and the condition of the above-described Expression (14) is defined by a template execution procedure.

In the present embodiment, since the condition of Expression (13) includes the condition of the Expression (14), the range of the parameter indicated by the condition of the Expression (13) is extracted as the final range of the variable parameter value defined by the template execution procedure.

In the culture-related process optimization device 302, the template execution procedure generation unit 15 receives the range of the variable parameter value sought by the optimal range search unit 303, and the template execution procedure generation unit 15 sets the range of the variable parameter value sought by the optimal range search unit 303 as a new search range for the variable parameter item of the execution template. Specifically, in the template execution procedure shown in FIG. 5, for example, the range of the variable parameter value sought by the optimal range search range 303 is set as a new search range for the variable parameter item 26g, such as that "3 μM≤BMP4 concentration ≤10 μM" is set as the variable parameter value of the "BMP4 concentration" for the variable parameter item 26g in the operation outline field C1.

As a result, the variable parameter value setting unit 16 can determine which variable parameter value within the set search range will be used to execute the execution procedure in the execution environment 100, on the basis of previous execution performance results and evaluation performance results in the same manner as in the above-described embodiments, and transmit a plurality of variable parameter values selected from within the search range to the execution procedure generation unit 17.

Furthermore, the execution procedure generation unit 17 can write the variable parameter values selected by the variable parameter value setting unit 16 respectively for the variable parameter item 26g of the template execution procedure in the same manner as in the above-described embodiments, and generate a plurality of execution procedures having different variable parameter values. In this way, the execution procedure generation unit 17 can generate a list of a plurality of execution procedures having different variable parameter values.

(4-3) Functions and Effects

In the above-described configuration, the culture-related process optimization device 302 acquires an existing condition related to the culture-related process as an existing condition acquisition unit through the transmission/reception unit 11 (existing condition acquisition step). The culture-related process optimization device 302 allows the optimal range search unit 303 to search for an optimal range of the variable parameter value that can generate an execution procedure outside the range of the existing condition, the optimal range not satisfying at least one or more constituent features among a plurality of constituent features included in the existing condition, within the search range of the variable parameter value set in advance (optimal range search step).

In this way, the culture-related process optimization device 302 sets the variable parameter value from within the optimal range of the variable parameter value searched in the optimal range search step, and generates an execution procedure, in the execution procedure generation step.

As a result, in the culture-related process optimization device 302, in addition to providing effects similar to those obtained in the above-described embodiment, a culture process with new conditions that have never existed in the past and avoids existing conditions, can be sought.

In the above-described embodiment, a case in which an optimal range logic expression of disjunctive normal form that generates an optimal range logic expression in the form of disjunction (or) of a conjunctive clause (and) is applied as the standard type optimal range logical expression, has been described; however, the invention is not limited to this, and for example, other various standard type optimal range logic expressions such as an optimal range logic expression of conjunctive normal form that generates an optimal range logic expression in the form of conjunction of a disjunctive clause, may also be applied. In addition, a case in which a standard type optimal range logic expression is obtained as an analysis result of the optimal range logic expression made by the logic expression analysis unit, has been described; however, the invention is not limited to this, and for example, conditions satisfying $P' \wedge Q$ may be induced, and an optimal range logic expression indicating an optimal range that is within the search range of the variable parameter value and is outside the range of the existing condition, may be obtained, or other various solutions may be applied.

Furthermore, in the above-described embodiment, a case in which a transmission/reception unit 11 connected to a network 4 is applied as the existing condition acquisition unit has been described; however, the invention is not limited to this, and an interface that can be connected to an external instrument may be applied as the existing condition acquisition unit, and the existing condition may be directly acquired from the external instrument without involving the network 4.

In the above-described embodiment, as an example of the existing condition, a case in which one patent publication after patent prosecution or one publication of patent application before patent prosecution is applied as the patent publication data, has been described; however, the invention is not limited to this. As the existing condition, for example, patent publication data integrating a plurality of patent publications after patent prosecution, published unexamined patent data integrating a plurality of publication of patent applications before patent prosecution, or patent publication data integrating one or more patent publications after patent prosecution and one or more publication of patent applications before patent prosecution, may be applied.

In the case of using a plurality of patent publications or publication of patent applications as the patent publication data as described above, logic expressions P1, P2, ..., PN representing the scope of existing claims of the patent publications and/or publication of patent applications are respectively generated, and by obtaining the following Expression (15), which is a logical product of the negation of these logic expressions and the search range logic expression Q, processing similar to that in the above-described embodiment can be executed, and an optimal range of the variable parameter value can be determined.

$$(\neg P1 \wedge \neg P2 \wedge \ldots \wedge \neg PN) \wedge Q \qquad (15)$$

In addition, as other embodiments, a culture medium-related process optimization system combining the configuration of the second embodiment and the configuration of the fourth embodiment as described above, or a culture medium-related process optimization system combining the configuration of the third embodiment and the configuration of the fourth embodiment as described above may also be adopted.

REFERENCE SIGNS LIST

1, 301: culture-related process optimization system
2, 302: culture-related process optimization device
3*a*, 3*b*, 3*c*, 3*d*: communication device
8: database
11: transmission/reception unit (execution result acquisition unit, evaluation n result acquisition unit, existing condition acquisition unit)
15: template execution procedure generation unit
16: variable parameter value setting unit
17: execution procedure generation unit
19: execution schedule generation unit
20: execution instruction information generation unit
303: optimal range search unit
1501: starting point execution procedure acquisition unit
1504: variable parameter item identification unit
t: execution procedure abstract syntax tree (syntax tree)
t': extended abstract syntax tree (syntax tree)

The invention claimed is:

1. A culture-related process optimization method in a culture-related process optimization system comprising a culture-related process optimization device, the culture-related process optimization method comprising:

an acquisition step of acquiring, by a computer of the culture-related process optimization device, an initial execution procedure table that serves as a starting point of a search, wherein the initial execution procedure table defines one or a plurality of operations to be performed in a culture-related process relevant to culture of cells, and defines contents related to the operations;

a variable parameter item identification step of identifying, by the computer, one or a plurality of variable parameter items for which a variable parameter value is set in the initial execution procedure table;

a search range determining step of determining, by the computer, a search range indicating a range of the variable parameter value to be set in each of the variable parameter items;

a template execution procedure generation step of generating, by the computer, a template execution procedure in which the search range is set by rewriting the initial execution procedure table;

an execution procedure generation step of selecting, by the computer, the variable parameter value in the search range and setting the selected variable parameter value for the variable parameter item identified in the variable parameter item identification step on the basis of a previous execution performance result and an evaluation performance result thereof and thereby generating an execution procedure of the culture-related process;

an execution result acquisition step of acquiring, by the computer, an execution result obtained in response to an execution subject actually executing the execution procedure in an execution environment;

an evaluation result acquisition step of acquiring, by the computer, an evaluation result with respect to the execution result, wherein the evaluation result is at least one of cost, yield, quality, and execution time related to the execution procedure, variations in the cost, the yield, the quality, and the execution time, and deviations from given target values of the cost, the yield, the quality, and the execution time;

a storage step of recording, in a storage of the culture-related process optimization device, the execution procedure, the selected variable parameter value, the execution result, and the evaluation result in association with each other in a database; and a determination step of determining, by the computer, whether the evaluation result is a predetermined evaluation result, wherein in the determination step,
  upon determining that the evaluation result is not the predetermined evaluation result, changing the variable parameter value within the search range set in the template execution procedure to generate a new execution procedure, and
  upon determining that the evaluation result is the predetermined evaluation result, terminating the culture-related process optimization method.

2. The culture-related process optimization method according to claim 1,
  wherein the culture-related process includes at least any one of an operation related to adjustment of a culture medium and an operation related to cell culture using the culture medium, as the operation.

3. The culture-related process optimization method according to claim 1,
  wherein the culture-related process is a culture medium adjustment process of adjusting a culture medium and/or a cell culture process of culturing cells.

4. The culture-related process optimization method according to claim 1,
  wherein in the variable parameter item identification step, one or a plurality of the variable parameter items for which the variable parameter value is set in the initial execution procedure table are identified, on the basis of the execution performance result obtained in response to the execution subject executing a previous execution procedure that is identical or relevant to the initial execution procedure table in the execution environment.

5. The culture-related process optimization method according to claim 1,
  wherein in the execution procedure generation step, the variable parameter value is determined on the basis of the execution performance result obtained in response to the execution subject executing a previous execution procedure that is identical or relevant to the initial execution procedure table in the execution environment.

6. The culture-related process optimization method according to claim 1,
  wherein in the execution procedure generation step, a regression model is generated on the basis of the execution performance result, and the variable parameter value to be set for the variable parameter item is determined by using the regression model.

7. The culture-related process optimization method according to claim 1,
  further comprising an execution schedule generation step of generating an execution schedule indicating how the plurality of operations specified by the execution procedure are collaboratively executed in a time series by the respective corresponding execution subjects in the execution environment.

8. The culture-related process optimization method according to claim 1,
  wherein in the execution procedure generation step, a constraint condition used by the execution subject executing the execution procedure in the execution environment is set for a constraint condition item of the execution procedure.

9. The culture-related process optimization method according to claim 1,
  wherein in the variable parameter item identification step, an item selection simulation of selecting a parameter value for item selection with respect to a candidate variable parameter item that becomes the variable parameter item, which is assumed to allow a predetermined evaluation result to be obtained, and using the selected parameter value for item selection as input and the evaluation result as output, is executed by arithmetic processing, and the variable parameter item is selected on the basis of a result of the item selection simulation.

10. The culture-related process optimization method according to claim 1,
  wherein in the execution procedure generation step, a variable parameter value selection simulation of selecting a candidate variable parameter value that becomes the variable parameter value, which is assumed to allow a predetermined evaluation result to be obtained, and using the selected candidate variable parameter value as input and the evaluation result as output, is executed by arithmetic processing, and a range of the variable parameter value is limited on the basis of a result of the variable parameter value selection simulation.

11. The culture-related process optimization method according to claim 1, further comprising,
  before the execution procedure generation step,
  an existing condition acquisition step of acquiring an existing condition related to the culture-related process; and
  an optimal range search step of searching for an optimal range of the variable parameter value capable of generating the execution procedure outside the range of the existing condition, the optimal range not satisfying at least one or more constituent features among a plurality of constituent features included in the existing condition within a search range of the variable parameter value specified in advance,
  wherein in the execution procedure generation step, the variable parameter value is set in an optimal range of the variable parameter value searched in the optimal range search step, and then the execution procedure is generated.

12. The culture-related process optimization method according to claim 11, wherein the optimal range search step includes
- an optimal range logic expression generation step of generating an optimal range logic expression that expresses an optimal range of the variable parameter value as a logic expression, on the basis of an existing condition logic expression expressing the existing condition as a logic expression and of a search range logic expression expressing a search range of the variable parameter value that has been set in advance as a logic expression; and
- an analysis step of analyzing the optimal range logic expression and identifying an optimal range of the variable parameter value capable of generating a different execution procedure, the optimal range being outside the range of the existing condition, for each of the variable parameter items.

13. The culture-related process optimization method according to claim 11,
- wherein the existing condition is a patent publication or a publication of patent application, in the existing condition acquisition step,
- an existing claim described in the patent publication or the publication of patent application is acquired as the existing condition, and
- the optimal range search step includes:
  - a patent information analysis step of analyzing dependency relationships among a plurality of existing claims and analyzing mutual relationships among a plurality of constituent features respectively specified within the existing claims for each of the existing claims.

14. A culture-related process optimization system comprising:
- a culture-related process optimization device that comprises:
  - a computer that:
    - acquires an initial execution procedure table that serves as a starting point of a search, wherein the initial execution procedure table defines one or a plurality of operations to be performed in a culture-related process relevant to culture of cells, and defines contents related to the operations,
    - identifies one or a plurality of variable parameter items for which a variable parameter value is set in the initial execution procedure table,
    - determines a search range indicating a range of the variable parameter value to be set in each of the variable parameter items,
    - generates a template execution procedure in which the search range is set by rewriting the initial execution procedure table,
    - selects the variable parameter value in the search range and sets the selected variable parameter value for the identified variable parameter item on the basis of a previous execution performance result and an evaluation performance result thereof and thereby generates an execution procedure of the culture-related process,
    - acquires an execution result obtained in response to an execution subject actually executing the execution procedure in an execution environment,
    - acquires an evaluation result with respect to the execution result, wherein the evaluation result is at least one of cost, yield, quality, and execution time related to the execution procedure, variations in the cost, the yield, the quality, and the execution time, and deviations from given target values of the cost, the yield, the quality, and the execution time, and
    - determines whether the evaluation result is a predetermined evaluation result; and
  - a storage that stores a database recording the execution procedure, the selected variable parameter value, the execution result, and the evaluation result in association with each other, wherein
- the computer further:
  - upon determining that the evaluation result is not the predetermined evaluation result, changes the variable parameter value within the search range set in the template execution procedure to generate a new execution procedure, and
  - upon determining that the evaluation result is the predetermined evaluation result, terminates the culture-related process optimization method.

* * * * *